US010323012B2

(12) United States Patent
Zhang

(10) Patent No.: US 10,323,012 B2
(45) Date of Patent: Jun. 18, 2019

(54) MILIUSANES AS ANTIVIRAL AGENTS

(71) Applicant: Hong Kong Baptist University, Hong Kong (HK)

(72) Inventor: Hongjie Zhang, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 0 days.

(21) Appl. No.: 15/802,534

(22) Filed: Nov. 3, 2017

(65) Prior Publication Data

US 2018/0065946 A1    Mar. 8, 2018

Related U.S. Application Data

(63) Continuation-in-part of application No. 15/610,926, filed on Jun. 1, 2017, now Pat. No. 9,822,071, which is a continuation-in-part of application No. 14/927,485, filed on Oct. 30, 2015, now Pat. No. 9,695,141, which is a continuation-in-part of application No. 13/831,997, filed on Mar. 15, 2013, now Pat. No. 9,211,333.

(60) Provisional application No. 61/655,990, filed on Jun. 5, 2012.

(51) Int. Cl.
| | |
|---|---|
| *A61K 31/343* | (2006.01) |
| *A61K 31/403* | (2006.01) |
| *C07D 307/94* | (2006.01) |
| *C07D 209/54* | (2006.01) |
| *A61K 31/365* | (2006.01) |
| *A61K 31/4025* | (2006.01) |

(52) U.S. Cl.
CPC .......... *C07D 307/94* (2013.01); *A61K 31/343* (2013.01); *A61K 31/365* (2013.01); *A61K 31/403* (2013.01); *A61K 31/4025* (2013.01); *C07D 209/54* (2013.01)

(58) Field of Classification Search
CPC .. C07D 307/94; C07D 209/54; A61K 31/343; A61K 31/365; A61K 31/4025; A61K 31/403; A61K 45/06
USPC ......................................................... 514/409
See application file for complete search history.

(56) References Cited

FOREIGN PATENT DOCUMENTS

| WO | WO-2010148197 A1 * | 12/2010 | ........... A61K 31/506 |
|---|---|---|---|
| WO | WO-2013057320 A1 * | 4/2013 | ........... C07D 309/04 |

OTHER PUBLICATIONS

CDC (Centers for Disease Control and Prevention, US); Pneumocystis, pneumonia—Los Angeles; Morbidity and Mortality Weekly Report (MMWR); Jun. 5, 1981; vol. 30, Issue 21; pp. 250-252.
WHO (World Health Organization); Global Health Observatory (GHO) data: HIV/AIDS. http://www.who.int/gho/hiv/en/; retrieved on Oct. 11, 2017.
MSCID (Monthly Statistics of China Infectious Diseases); http://www.nhfpc.gov.cn/jkj/s3578/201709/d30e75fc9d2e4d09ab01279662b16b96.shtml; retrieved on Oct. 11, 2017.
NHFPC (National Health and Family Planning Commission of the People's Republic of China); China Health Statistics Yearbook 2014, 22-14; http://www.stats.gov.cn/tjsj/ndsj/2014/indexch.htm, retrieved on Oct. 11, 2017.
UNAIDS; UNAIDS Data 2017; ittp://www.unaids.org/sites/default/files/media_asset/20170720_Data_book_2017_en.pdf.
WHO (World Health Organization), CDC (Centers for Disease Control and Prevention) and The Global Fund; HIV drug resistance report 2017.
WHO 2017; Cumulative number of confirmed human cases for avian influenza A (H5N1) reported to WHO, 2003-2017; http://www.who.int/influenza/human_animal_interface/EN_GIP_20130705CumulativeNumberH5N1cases_2.pdf.
Russell et al.; The genesis of a pandemic influenza virus; Cell; Nov. 4, 2005;vol. 123, Issue 3; pp. 368-371.
Basler et al.; Sequence of the 1918 pandemic influenza virus nonstructural gene (NS) segment and characterization of recombinant viruses bearing the 1918 NS genes; Proceedings of the National Academy of Sciences of the United States of America; Feb. 27, 2001; vol. 98, Issue 5; pp. 2746-2751.
Gibbs et al.; From where did the 2009 'swine-origin' influenza A virus (H1N1) emerge?; Virology Journal; Nov. 24, 2009; vol. 6; 207.
WHO 2013; Number of confirmed human cases for avian influenza A (H7N9) reported to WHO, report 10, data in WHO/HQ as of Oct. 25, 2013; http://www.who.int/influenza/human_animal_interface/influenza_h7n9/10u_ReportWebH7N9Number.pdf.
Fauci; Emerging and re-emerging infectious diseases: influenza as a prototype of the host-pathogen balancing act; Cell; Feb. 24, 2006; vol. 124, Issue 4; pp. 665-670.
Beigel et al.; Avian influenza A (H5N1) infection in humans; The New England Journal of Medicine; Sep. 29, 2005; vol. 353, Issue 13; pp. 1374-1385.
Imai et al.; Experimental adaptation of an influenza H5 HA confers respiratory droplet transmission to a reassortant H5 HA/H1N1 virus in ferrets; Nature; Jun. 21, 2012; vol. 486, Issue 7403; pp. 420-428.
Herfst et al.; Airborne transmission of influenza A/H5N1 virus between ferrets; Science; Jun. 22, 2012; vol. 336, Issue 6088; pp. 1534-1541. Peiriset al.; Surveillance of animal influenza for pandemic preparedness; Science; Mar. 9, 2012; vol. 335, Issue 6073; pp. 1173-1174.
Li et al.; Genesis of a highly pathogenic and potentially pandemic H5N1 influenza virus in eastern Asia; Nature; Jul. 8, 2004; vol. 430, Issue 6996; pp. 209-213.
Govorkova et al.; Antiviral resistance among highly pathogenic influenza A (H5N1) viruses isolated worldwide in 2002-2012 shows need for continued monitoring; Antiviral Research; May 2013; vol. 98, Issue 2; pp. 297-304.

* cited by examiner

Primary Examiner — Kristin A Vajda
(74) Attorney, Agent, or Firm — Spruson & Ferguson (Hong Kong) Limited

(57) ABSTRACT

The present disclosure relates to miliusane and analogs thereof that are useful as anti-virals, such as anti-HIV and anti-influenza virus agents. The present disclosure provides methods for treating viral infections, such as AIDS, HIV, and influenza infections.

19 Claims, No Drawings

MILIUSANES AS ANTIVIRAL AGENTS

CROSS-REFERENCE TO RELATED APPLICATIONS

The present application is a continuation-in-part application of U.S. patent application Ser. No. 15/610,926, filed on Jun. 1, 2017. U.S. patent application Ser. No. 15/610,926 is a continuation-in-part of U.S. patent application Ser. No. 14/927,485, filed on Oct. 30, 2015, now U.S. Pat. No. 9,695,141, which in turn is a continuation-in-part of U.S. patent application Ser. No. 13/831,997, filed on Mar. 15, 2013, now U.S. Pat. No. 9,211,333, which claims priority of U.S. provisional patent application No. 61/655,990, filed Jun. 5, 2012, all of which are incorporated herein by reference in their entirety.

FIELD OF INVENTION

The present disclosure is in the field of pharmaceuticals and chemical industries. More particularly, the present disclosure relates to miliusane and analogs thereof that are useful as anti-viral agents, such as anti-HIV and anti-influenza virus agents. The present disclosure also provides methods for treating viral infections, such as AIDS, HIV, and influenza infections.

BACKGROUND OF INVENTION

Human Immunodeficiency Virus (HIV) was first established as the viral agent that causes acquired immunodeficiency syndrome (AIDS) in humans 36 years ago [CDC (Centers for Disease Control and Prevention, US). Pneumocystis pneumonia-Los Angeles. *Morbidity and Mortality Weekly Report (MMWR)* 1981; 30: 250-252.]. More than 70 million people have been infected with HIV, and about half of them have died since 1981 [WHO (World Health Organization). Global Health Observatory (GHO) data: HIV/AIDS. www.who.int/gho/hiv/en/; retrieved on 11 Oct. 2017]. In China, the number of HIV infections increased more than 39 times from 2008 to August, 2017, and the death rate is more than 30% [ MSCID (Monthly Statistics of China Infectious Diseases); www.nhfpc.gov.cn/jkj/s3578/201709/d30e75fc9d2e4d09ab01279662b16b96.shtml; retrieved on 11 Oct. 2017]. AIDS has been ranked as the leading cause of death among the infectious diseases in China since 2007 [NHFPC (National Health and Family Planning Commission of the People's Republic of China). China Health Statistics Yearbook 2014, 22-14; www.stats.gov.cn/tjsj/ndsj/2014/indexch.htm, retrieved on 11 Oct. 2017]. Although today's anti-HIV drugs have significantly extended the life span of HIV-positive people in wealthy countries [UNAIDS. UNAIDS Data 2017. www.unaids.org/sites/default/files/media_asset/20170720_Data_book_2017_en.pdf], they have side effects and diminishing effectiveness due to the development of viral resistance [WHO (World Health Organization), CDC (Centers for Disease Control and Prevention) and The Global Fund. HIV drug resistance report 2017]. Since there are no drugs capable of curing at present, nor vaccine available to prevent this viral disease, the discovery and development of new anti-HIV drugs are very much needed and the undertaking of such studies are imperative.

Avian flu gained widespread attention in 1997 when cases of human infection from the H5N1 subtype of avian influenza were reported in Hong Kong. Since 2003, human H5N1 infected cases have been reported every year. As of Jul. 25, 2017, a total of 859 human H5N1 infected cases have been confirmed in 16 countries with a mortality rate greater than 50% [WHO 2017. Cumulative number of confirmed human cases for avian influenza A (H5N1) reported to WHO, 2003-2017. www.who.int/influenza/human_animal_interface/EN_GIP_20130705CumulativeNumberH5N1cases_2.pdf].

Historically, pandemics have been caused by the introduction of a wholly avian virus or an avian-human reassortant, to which human populations lack immunity (Russell C J, Webster R G. The genesis of a pandemic influenza virus. Cell. 2005; 123: 368-71). In the 20th century, three major pandemics occurred: in 1918 (Spanish Flu), 1957 (Asian Flu), and 1968 (Hong Kong influenza). The largest and most deadly pandemic in recorded history occurred in 1918 with an estimated death toll of more than 40 million people worldwide, which was caused by an H1N1 subtype influenza A virus [Basler C F, Reid A H, Dybing J K, Janczewski T A, Fanning T G, Zheng H, et al. Sequence of the 1918 pandemic influenza virus nonstructural gene (NS) segment and characterization of recombinant viruses bearing the 1918 NS genes. Proc Natl Acad Sci USA. 2001; 98: 2746-51]. The deadly outbreaks of the H1N1 "swine flu" in 2009 [Gibbs A J, Armstrong J S, Downie J C. From where did the 2009 'swine-origin' influenza A virus (H1N1) emerge? Virol J. 2009; 6: 207] and the H7N9 avian influenza A in 2013 [WHO 2013. Number of confirmed human cases for avian influenza A (H7N9) reported to WHO, report 10, data in WHO/HQ as of 25 Oct. 2013. www.who.int/influenza/human_animal_interface/influenza_h7n9/10u_ReportWebH7N9Number.pdf] have caused alarm worldwide.

Influenza virus H5N1 (a subtype of influenza A virus) is an avian pathogen that originally circulated in wild birds without causing disease. The virus jumped to poultry flocks in Southeast Asia at an unknown time, causing only mild symptoms of disease in birds (Fauci A S. Emerging and re-emerging infectious diseases: influenza as a prototype of the host-pathogen balancing act. Cell. 2006; 124: 665-70). As the virus infected chickens and other domestic poultry, it mutated to its current highly pathogenic form. In general, as avian influenza viruses do not replicate efficiently in humans, direct transmission of avian viruses to humans is probably an extremely rare event [Beigel J H, Farrar J, Han A M, Hayden F G, Hyer R, de Jong M D, et al. Avian influenza A (H5N1) infection in humans. N Engl J Med. 2005; 353: 1374-85]. However, two research groups successfully produced modified H5N1 virus in the separate laboratories in 2012. The genetically modified viruses are capable of acquiring the capacity for airborne transmission among mammals [Imai M, Watanabe T, Hatta M, Das S C, Ozawa M, Shinya K, et al. Experimental adaptation of an influenza H5 HA confers respiratory droplet transmission to a reassortant H5 HA/H1N1 virus in ferrets. Nature. 2012; 486: 420-8; Herfst S, Schrauwen E J A, Linster M, Chutinimitkul S, Wit E, Munster V J, et al. Airborne transmission of influenza A/H5N1 virus between ferrets. Science. 2012; 336: 1534-41]. The studies demonstrated the possibility that naturally occurring H5N1 avian influenza virus may one day mutate to become airborne and transmissible to humans. Thus, there is a need to prepare for potential pandemics caused by future strains influenza viruses.

A pandemic caused by H5N1 is considered more dangerous in comparison with those caused by other types of influenza viruses due to high mortality rates of patients infected by H5N1. An ideal way to combat the avian influenza virus in humans is to block or at least reduce the likelihood of interspecies transfer, and this requires a comprehensive, multifaceted approach (Peiris J S M, Poon L L M, Guan Y. Surveillance of animal influenza for pandemic preparedness. Science. 2012; 335: 1173-4). Antivirals form an important part of this approach. Neuraminidase (NA) inhibitors efficiently blocked the NA activity of the 2004 H5N1 viruses in vitro, indicating their potential effectiveness in influenza chemotherapy and prophylaxis against H5N1 virus infection. However, recent isolation of resistant mutants against these compounds has emphasized the need for careful monitoring to control potential pandemic influenza. For example, most seasonal strains of influenza, including H5N1, now exhibit resistance to amantadine and amantadine. The 2004 H5N1 Vietnam and Thailand isolates were resistant to amantadine, because of mutations in the M2 gene segment (Li K S, Guan Y, Wang J, Smith G J, Xu K M, Duan L, et al. Genesis of a highly pathogenic and potentially pandemic H5N1 influenza virus in eastern Asia. Nature. 2004; 430: 209-13) and this limits the use of amantadine and amantadine derivatives for controlling potential pandemics [Govorkova E A, Baranovich T, Seiler P, Armstrong J, Burnham A, Guan Y, et al. Antiviral resistance among highly pathogenic influenza A (H5N1) viruses isolated worldwide in 2002-2012 shows need for continued monitoring. Antivir. Res. 2013; 98: 297-304]. These events highlight the urgent need for development of new antivirals. Thus, there is a need to identify and develop novel treatment for viral infections, such as HIV, AIDS, and influenza.

SUMMARY OF INVENTION

The present disclosure relates to compounds having antiviral properties, such as anti-HIV and anti-influenza, which are isolated from *Miliusa* (Annonaceae) plants and analogs thereof. More particularly, provided herein are methods of treating viral infections, such as HIV, AIDS, and influenza using miliusanes and analogs thereof.

The present disclosure provides a series of anti-viral, e.g., anti-HIV and anti-influenza virus, compounds belonging to a cluster of molecules, referred herein to as "miliusanes", which were originally isolated from the leaves, twigs and flowers of *Miliusa sinensis* Finet and Gagnep. (Annonaceae) (Zhang H J, Ma C Y, Hung N V, Cuong N M, Tan G T, Santarsiero B D, Mesecar A D, Soejarto D D, Pezzuto J M, Fong H H S. Miliusanes, a class of cytotoxic agents from *Miliusa sinensis*. Journal of Medicinal Chemistry 2006; 49: 693-708). Representative miliusane compounds are shown below:

Miliusol

Miliusate

Miliusane I

Additional miliusane analogs are described in U.S. patent applications U.S. Ser. No. 13/931,997 and U.S. Ser. No. 14/927,485, including N-methyl-2-pyrrolecarboxyl-miliusol, p-dimethylamino-benzoyl-miliusol, 4β-(N-phenyl)miliusate, 4α-(N-phenyl)miliusate, 4β-(N-benzoyl-N-phenyl)miliusate, 4α-(N-benzoyl-N-phenyl)miliusate, hexahydro-miliusate, 3, 4-dihydro-miliusate, 2', 3', 6', 7'-tetrahydro-miliusate, 2-hydroxy-3, 4-dihydro-miliusate, 2-acetoxy-3, 4-dihydro-miliusate, 8'-oxo-miliusate, 8'-hydroxy-miliusate, 10'-hydroxy-8'-oxo-miliusate, 8', 10'-dihydroxy-miliusate, 5β-(p-trimethylammonio-benzoyl)miliusol iodide, and 5β-(p-dimethyl-allyl-ammonio-benzoyl)miliusol bromide having the following structural formula:

N-Methyl-2-pyrrolecarboxyl-miliusol p-Dimethylamino-benzyol-miliusol

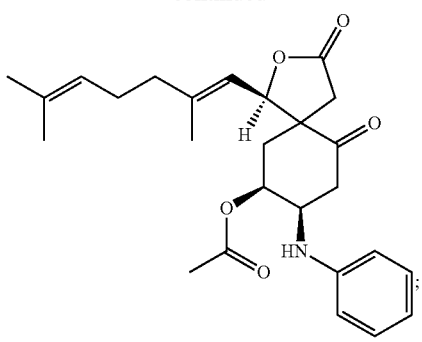
4β-(N-Phenyl)miliusate
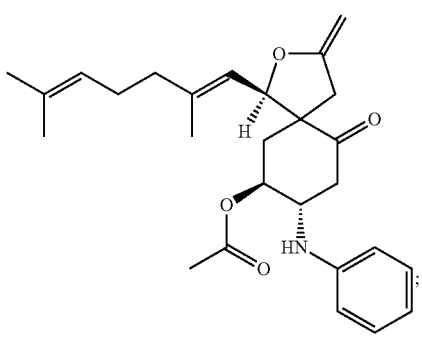
4α-(N-Phenyl)miliusate
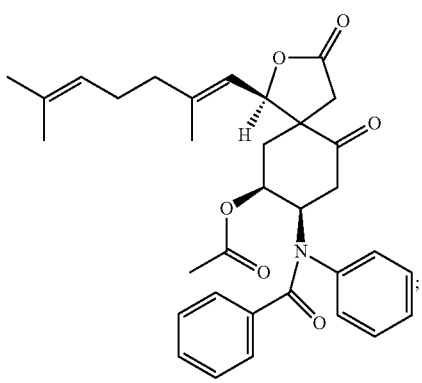
4β-(N-Benzoyl-N-phenyl)miliusate
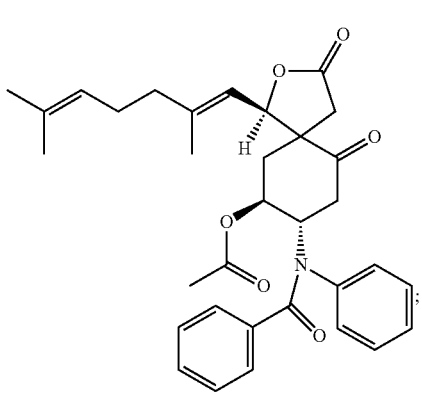
4α-(N-Benzoyl-N-phenyl)miliusate
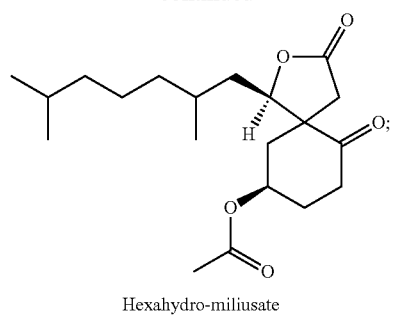
Hexahydro-miliusate
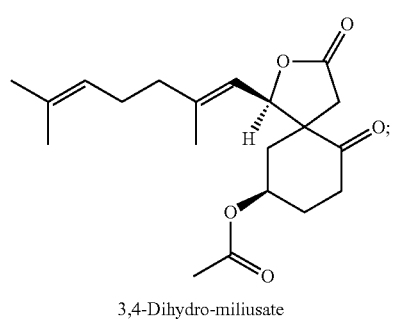
3,4-Dihydro-miliusate
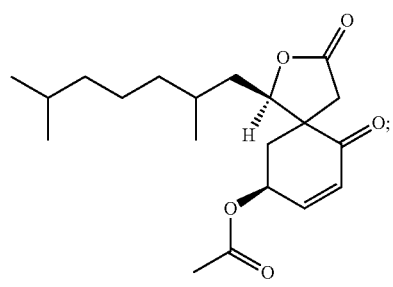
2′,3′,6′,7′-Tetrahydro-miliusate
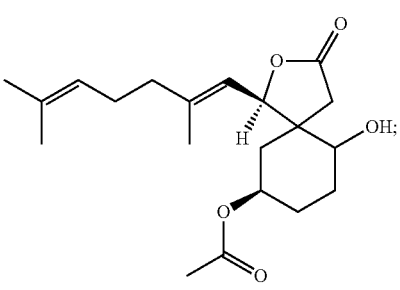
2-Hydroxy-3,4-dihydro-miliusate
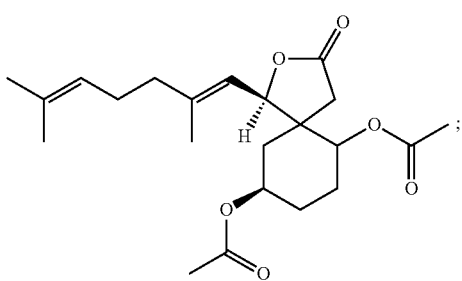
2-Acetoxy-3,4-dihydro-miliusate

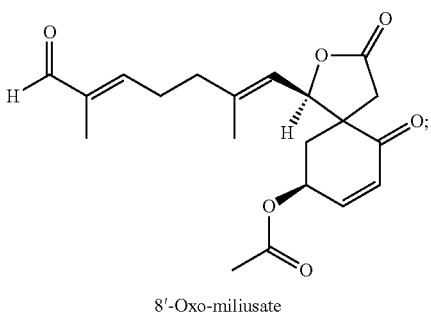

8'-Oxo-miliusate

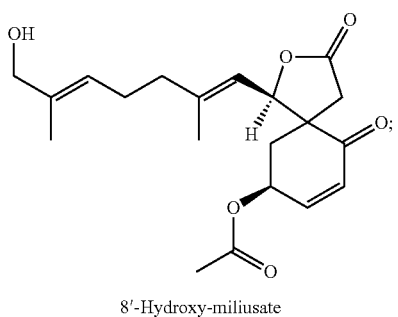

8'-Hydroxy-miliusate

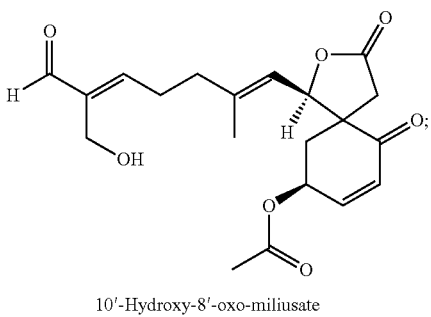

10'-Hydroxy-8'-oxo-miliusate

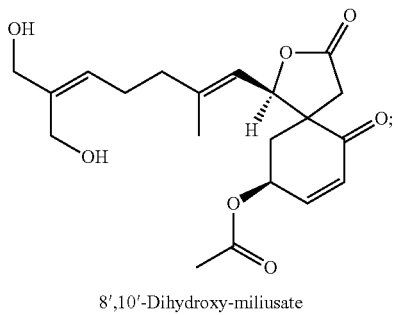

8',10'-Dihydroxy-miliusate

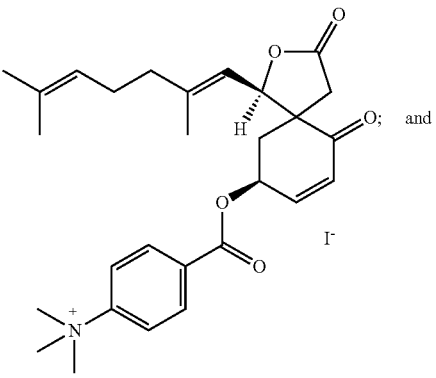

5β-(p-Trimethylammonio-benzoyl)miliusol iodide and

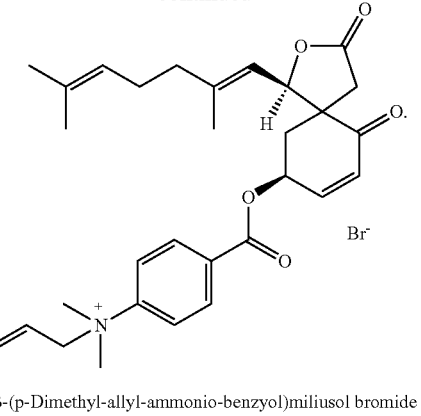

5β-(p-Dimethyl-allyl-ammonio-benzyol)miliusol bromide

In a first aspect of the present disclosure, there is provided a method of treating a viral infection in a subject in need thereof, comprising administering a therapeutically effective amount of a compound of Formula (I) or Formula (II) to said subject, wherein the compound of Formula (I) and compound of Formula (II) are represented by:

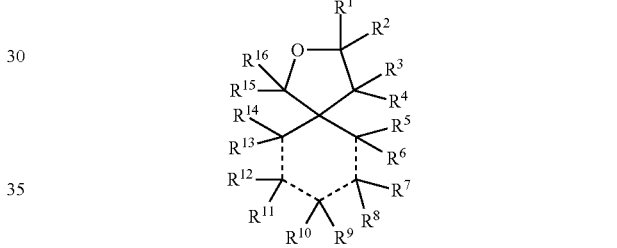

(I)

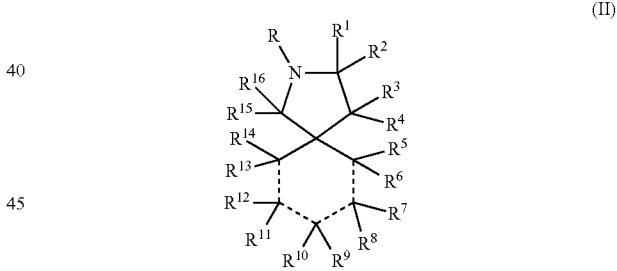

(II)

or a pharmaceutically acceptable salt or prodrug thereof, wherein a
dashed line represents a single or double bond;
$R^1$ and $R^2$ are hydrogen; or taken together with the carbon atoms to which they are attached to form a carboxyl group (C=O);
each of $R^3$ and $R^4$ are independently selected from the group consisting of hydrogen, halogen, and hydroxy; or $R^3$ and $R^4$ taken together with the carbon atoms to which they are attached to form a carboxyl group (C=O);
each of $R^5$ and $R^6$ are independently selected from the group consisting of hydrogen, halogen, and —$OR^{19}$; or $R^5$ and $R^6$ taken together with the carbon atoms to which they are attached to form a carboxyl group (C=O);
each pair of the substituted groups $R^7$ and $R^8$, $R^9$ and $R^{10}$, or $R^{11}$ and $R^{12}$ is independently taken together with the carbon atoms to which they are attached to form one or more carboxyl groups (C=O); or while one substituent of $R^7$ and $R^8$, one substituent of $R^9$ and $R^{10}$, or one substituent of $R^{11}$ and $R^{12}$ is hydrogen or halogen whereas the other substituent of $R^7$ and $R^8$, the other substituent of $R^9$ and $R^{10}$, or the other substituent of $R^{11}$ and $R^{12}$ is selected from —N($R^{17}$)$R^{18}$ or —N($R^{17}$)C(=O)$R^{18}$; or while one substituent of $R^7$ and $R^8$, one substituent of $R^9$ and $R^{10}$, or one substituent of $R^{11}$ and $R^{12}$ is hydrogen or halogen whereas the other substituent of $R^7$ and $R^8$, the other substituent of $R^9$ and $R^{10}$, or the other substituent of $R^{11}$ and $R^{12}$ is selected from hydrogen and —O$R^{19}$;

$R^{13}$ and $R^{14}$ are independently selected from the group consisting of hydrogen and —O$R^{19}$; or $R^{13}$ and $R^{14}$ taken together with the carbon atoms to which they are attached to form a carboxyl group (C=O);

$R^{15}$ and $R^{16}$ are independently selected from the group consisting of hydrogen and hydrocarbyl, wherein said hydrocarbyl has at least five carbons, and may be optionally substituted with one, two, or three substituents independently selected from hydroxy, halogen, aldehyde group (H—C=O), C(=O)OH, $C_{1-6}$ alkyl and $C_{1-6}$ alkoxy;

each instance of $R^{17}$ and $R^{18}$ are independently selected from hydrogen, hydrocarbyl optionally substituted with one, two, three, four or five $R^{20}$, heterocyclyl optionally substituted with one, two, three, four or five $R^{20}$ and —(CH$_2$)$_k$-heterocyclyl optionally substituted with one, two, three, four or five $R^{20}$;

$R^{19}$ is selected from $R^{21}$ and —C(=O)$R^{21}$;

each instance of $R^{20}$ is independently selected from the group consisting of halogen, cyno, nitro, —$R^{22}$, —O$R^{22}$, —C(=O)$R^{23}$, —C(=O)N($R^{22}$)$R^{23}$, —C(=O)O$R^{22}$, —OC(=O)$R^{23}$, —N($R^{22}$)$R^{23}$, —N($R^{22}$)C(=O)$R^{23}$, —N($R^{22}$)($R^{23}$)$R^{24}$, —S$R^{22}$, —S(=O)$R^{23}$, —S(=O)$R^{23}$, —S(O)$_2R^{23}$, —S(O)$_2$N($R^{22}$)$R^{23}$, and —N($R^{22}$)S(O)$_2R^{23}$;

$R^{21}$ is selected from hydrogen, heterocyclyl optionally substituted with one, two, three, four or five $R^{20}$, hydrocarbyl optionally substituted with one, two, three, four or five $R^{20}$, heteroaryl optionally substituted with one, two, three, four or five $R^{20}$, and —(CH$_2$)$_k$— heterocyclyl optionally substituted with one, two, three, four or five $R^{20}$;

each instance of k is independently selected from an integer selected between 1 and 6;

$R^{22}$, $R^{23}$ and $R^{24}$ are each independently selected from hydrogen, or hydrocarbyl and heterocyclyl, either of which is optionally substituted with one, two, three, four or five substituents independently selected from halogen, cyano, amino, hydroxy, $C_{1-6}$ alkyl and $C_{1-6}$ alkoxy; and R is selected from hydrogen and hydrocarbyl.

In a first embodiment of the first aspect of the present disclosure, there is provided a method wherein said compound of Formula (I) has Formula (IA):

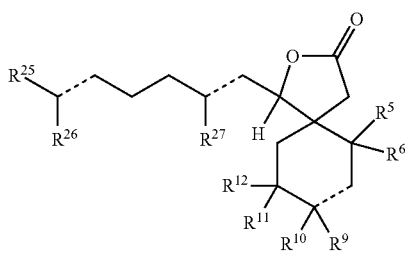

IA or a pharmaceutically acceptable salt or prodrug thereof, wherein a dashed line represents a single or double bond;

$R^5$ and $R^6$ are each independently selected from the group consisting of hydrogen and —O$R^{19}$; or $R^5$ and $R^6$ taken together with the carbon to which they are attached form a carboxyl group (C=O);

while one substituent of $R^9$ and $R^{10}$, or one substituent of $R^{11}$ and $R^{12}$ is hydrogen or halogen whereas the other substituent of $R^9$ and $R^{10}$, or the other substituent of $R^{11}$ and $R^{12}$ is selected from —N($R^{17}$)$R^{18}$ or —N($R^{17}$)C(=O)$R^{18}$; or while one substituent of $R^9$ and $R^{10}$, or one substituent of $R^{11}$ and $R^{12}$ is hydrogen or halogen whereas the other substituent of $R^9$ and $R^{10}$, or the other substituent of $R^{11}$ and $R^{12}$ is selected from hydrogen and —O$R^{19}$;

each of $R^{17}$ and $R^{18}$ is independently selected from hydrogen, heterocyclyl optionally substituted with one to five $R^{20}$, and hydrocarbyl optionally substituted with one to five $R^{20}$;

$R^{19}$ is selected from $R^{21}$ and —C(=O)$R^{21}$;

$R^{20}$ is independently selected from the group consisting of halogen, nitro, —$R^{22}$, —O$R^{22}$, —C(=O)$R^{23}$, —C(=O)N($R^{22}$)$R^{23}$, —OC(=O)$R^{23}$, —N($R^{22}$)$R^{23}$, —N($R^{22}$)C(=O)$R^{23}$, and —N($R^{22}$)($R^{23}$)($R^{24}$);

$R^{21}$ is selected from hydrogen, heterocyclyl optionally substituted with one to five $R^{20}$, and hydrocarbyl optionally substituted with one to five $R^{20}$;

$R^{22}$, $R^{23}$ and $R^{24}$ are each independently selected from hydrogen, hydrocarbyl and heterocyclyl; and each of $R^{25}$, $R^{26}$, and $R^{27}$ is independently selected from the group consisting of methyl, —CH$_2$OH, C(=O)H, and C(=O)OH.

In a second embodiment of the first aspect of the present disclosure, there is provided a method, wherein said compound of Formula (I) has Formula (IB):

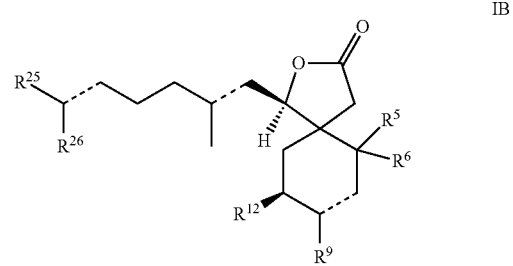

IB or a pharmaceutically acceptable salt or prodrug thereof, wherein a dashed line represents a single or double bond;

$R^5$ and $R^6$ are each independently selected from the group consisting of hydrogen and —O$R^{19}$; or $R^5$ and $R^6$ taken together with the carbon to which they are attached form a carboxyl group (C=O);

$R^9$ is hydrogen, —N($R^{17}$)$R^{18}$, —N($R^{17}$)C(=O)$R^{18}$, or —O$R^{19}$;

$R^{12}$ is hydrogen or —O$R^{19}$;

each of $R^{17}$ and $R^{18}$ is independently selected from hydrogen, heterocyclyl optionally substituted with one to five $R^{20}$, and hydrocarbyl optionally substituted with one to five $R^{20}$;

$R^{19}$ is selected from $R^{21}$ and —C(=O)$R^{21}$;

$R^{20}$ is independently selected from the group consisting of halogen, nitro, —$R^{22}$, —O$R^{22}$, —C(=O)$R^{23}$, —C(=O)

$N(R^{22})R^{23}$, $-OC(=O)R^{23}$, $-N(R^{22})R^{23}$, $-N(R^{22})C(=O)R^{23}$, and $-N(R^{22})(R^{23})R^{24}$;

$R^{21}$ is selected from hydrogen, heterocyclyl optionally substituted with one to five $R^{20}$, and hydrocarbyl optionally substituted with one to five $R^{20}$;

$R^{22}$, $R^{23}$ and $R^{24}$ are each independently selected from hydrogen, hydrocarbyl and heterocyclyl; and each of $R^{25}$ and $R^{26}$ is independently selected from the group consisting of methyl, $-CH_2OH$, $C(=O)H$, and $C(=O)OH$.

In a third embodiment of the first aspect of the present disclosure, there is provided a method, wherein said compound of Formula (I) has Formula (IB); $R^5$ is hydrogen and $R^6$ is hydroxyl or $-OC(=O)$alkyl; or $R^5$ and $R^6$ taken together with the carbon to which they are attached form a carboxyl group (C=O);

$R^9$ is hydrogen, $-N(R^{17})R^{18}$, $-N(R^{17})C(=O)R^{18}$, or $-OR^{19}$;

$R^{12}$ is hydrogen or $-OR^{19}$;

each of $R^{17}$ and $R^{18}$ is independently selected from hydrogen and hydrocarbyl optionally substituted with one to five $R^{20}$;

$R^{19}$ is selected from $R^{21}$ and $-C(=O)R^{21}$;

$R^{20}$ is independently selected from the group consisting of halogen, nitro, $-R^{22}$, $-OR^{22}$, $-N(R^{22})R^{23}$, $-N(R^{22})(R^{23})R^{24}$;

$R^{21}$ is selected from hydrogen and hydrocarbyl optionally substituted with one to five $R^{20}$;

$R^{22}$, $R^{23}$ and $R^{24}$ are each independently selected from hydrogen and alkyl; and each of $R^{25}$ and $R^{26}$ is independently selected from the group consisting of methyl, $-CH_2OH$, $C(=O)H$, and $C(=O)OH$.

In a fourth embodiment of the first aspect of the present disclosure, there is provided a method, wherein said compound of Formula (II) has Formula (IIA):

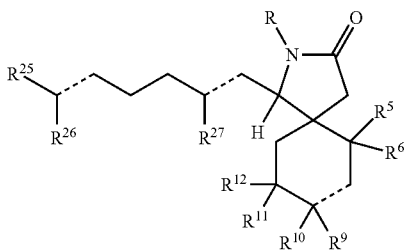

or a pharmaceutically acceptable salt or prodrug thereof, wherein a dashed line represents a single or double bond;

R is hydrogen, alkyl, aryl, or $C_{1-6}$ alkyl substituted by aryl.

$R^5$ and $R^6$ are each independently selected from the group consisting of hydrogen and $-OR^{19}$; or $R^5$ and $R^6$ taken together with the carbon to which they are attached form a carboxyl group (C=O);

while one substituent of $R^9$ and $R^{10}$, or one substituent of $R^{11}$ and $R^{12}$ is hydrogen or halogen whereas the other substituent of $R^9$ and $R^{10}$, or the other substituent of $R^{11}$ and $R^{12}$ is selected from $-N(R^{17})R^{18}$ or $-N(R^{17})C(=O)R^{18}$; or while one substituent of $R^9$ and $R^{10}$, or one substituent of $R^{11}$ and $R^{12}$ is hydrogen or halogen whereas the other substituent of $R^9$ and $R^{10}$, or the other substituent of $R^{11}$ and $R^{12}$ is selected from hydrogen and $-OR^{19}$;

each of $R^{17}$ and $R^{18}$ is independently selected from hydrogen, heterocyclyl optionally substituted with one to five $R^{20}$, and hydrocarbyl optionally substituted with one to five $R^{20}$;

$R^{19}$ is selected from $R^{21}$ and $-C(=O)R^{21}$;

$R^{20}$ is independently selected from the group consisting of halogen, nitro, $-R^{22}$, $-OR^{22}$, $-C(=O)R^{23}$, $-C(=O)N(R^{22})R^{23}$, $-OC(=O)R^{23}$, $-N(R^{22})R^{23}$, $-N(R^{22})C(=O)R^{23}$, and $-N(R^{22})(R^{23})(R^{24})$;

$R^{21}$ is selected from hydrogen, heterocyclyl optionally substituted with one to five $R^{20}$, and hydrocarbyl optionally substituted with one to five $R^{20}$;

$R^{22}$, $R^{23}$ and $R^{24}$ are each independently selected from hydrogen, hydrocarbyl and heterocyclyl;

each of $R^{25}$, $R^{26}$, and $R^{27}$ is independently selected from the group consisting of methyl, $C(=O)H$, and $C(=O)OH$.

In a fifth embodiment of the first aspect of the present disclosure, there is provided a method, wherein said compound of Formula (II) has Formula (IIB):

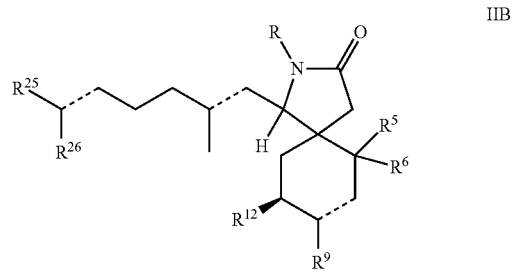

or a pharmaceutically acceptable salt or prodrug thereof, wherein a dashed line represents a single or double bond;

R is hydrogen, alkyl, aryl, or $C_{1-6}$ alkyl substituted by aryl;

$R^5$ and $R^6$ are each independently selected from the group consisting of hydrogen and $-OR^{19}$; or $R^5$ and $R^6$ taken together with the carbon to which they are attached form a carboxyl group (C=O);

$R^9$ is hydrogen, $-N(R^{17})R^{18}$, $-N(R^{17})C(=O)R^{18}$, or $-OR^{19}$;

$R^{12}$ is hydrogen or $-OR^{19}$;

each of $R^{17}$ and $R^{18}$ is independently selected from hydrogen, heterocyclyl optionally substituted with one to five $R^{20}$, and hydrocarbyl optionally substituted with one to five $R^{20}$;

$R^{19}$ is selected from $R^{21}$ and $-C(=O)R^{21}$;

$R^{20}$ is independently selected from the group consisting of halogen, nitro, $-R^{22}$, $-OR^{22}$, $-C(=O)R^{23}$, $-C(=O)N(R^{22})R^{23}$, $-OC(=O)R^{23}$, $-N(R^{22})R^{23}$, $-N(R^{22})C(=O)R^{23}$, and $-N(R^{22})(R^{23})R^{24}$;

$R^{21}$ is selected from hydrogen, heterocyclyl optionally substituted with one to five $R^{20}$, and hydrocarbyl optionally substituted with one to five $R^{20}$;

$R^{22}$, $R^{23}$ and $R^{24}$ are each independently selected from hydrogen, hydrocarbyl and heterocyclyl; and each of $R^{25}$ and $R^{26}$ is independently selected from the group consisting of methyl, $-CH_2OH$, $C(=O)H$, and $C(=O)OH$.

In a sixth embodiment of the first aspect of the present disclosure, there is provided a method, wherein said compound of Formula (II) has Formula (IIC):

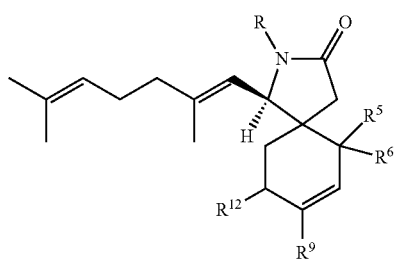

or a pharmaceutically acceptable salt or prodrug thereof, wherein

R is alkyl or aryl;

$R^5$ and $R^6$ taken together with the carbon to which they are attached form a carboxyl group (C=O);

$R^9$ is hydrogen;

$R^{12}$ is hydroxyl, —OC(=O)alkyl, —OC(=O)aryl, or —OC(=O)heteroaryl, wherein —OC(=O)aryl and —OC(=O)heteroaryl are each independently optionally substituted with one to five substituents selected from the group consisting of halogen, hydroxyl, nitro, alkyl, —N($R^{22}$)$R^{23}$, and —N($R^{22}$)($R^{23}$)($R^{24}$); and $R^{22}$, $R^{23}$ and $R^{24}$ are each independently selected from hydrogen and alkyl;

In a seventh embodiment of the first aspect of the present disclosure, there is provided a method, wherein said compound of formula (I) or said compound of formula (II) is selected from the group consisting of miliusane I, 4β-(N-phenyl)miliusate, 4α-(N-phenyl)miliusate, 4β-(N-benzoyl-N-phenyl)miliusate, 4α-(N-benzoyl-N-phenyl)miliusate, hexahydro-miliusate, 3, 4-dihydro-miliusate, 2', 3', 6', 7'-tetrahydro-miliusate, 2-hydroxy-3, 4-dihydro-miliusate, 2-acetoxy-3, 4-dihydro-miliusate, 8'-oxo-miliusate, 8'-hydroxy-miliusate, 10'-hydroxy-8'-oxo-miliusate, 8', 10'-dihydroxy-miliusate, 5β-(p-trimethylammonio-benzoyl)miliusol iodide, 5β-(p-dimethyl-allyl-ammonio-benzoyl)miliusol bromide, N-(n-butyl)-miliusol lactam and N-phenyl-miliusol lactam represented by the following formula:

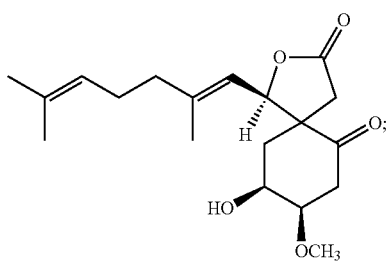

Miliusane I

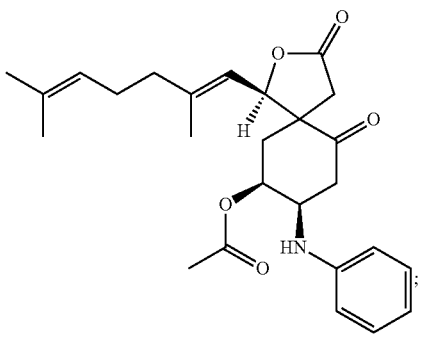

4β-(N-Phenyl)miliusate

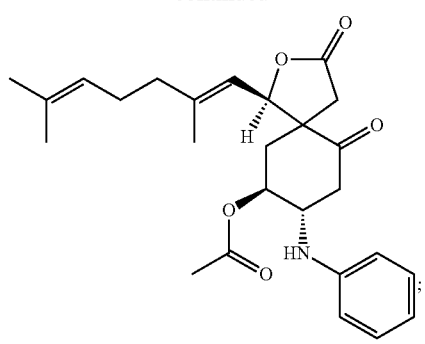

4α-(N-Phenyl)miliusate

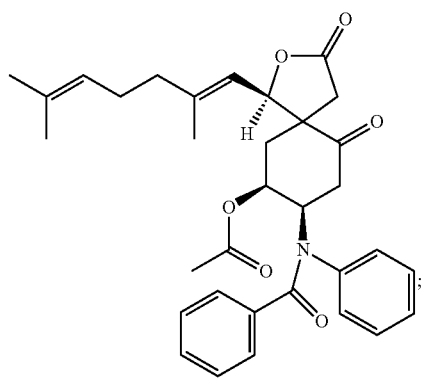

4β-(N-Benzoyl-N-phenyl)miliusate

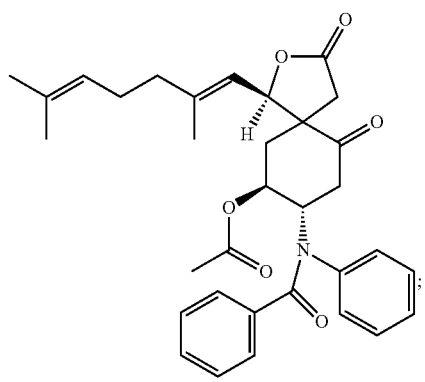

4α-(N-Benzoyl-N-phenyl)miliusate

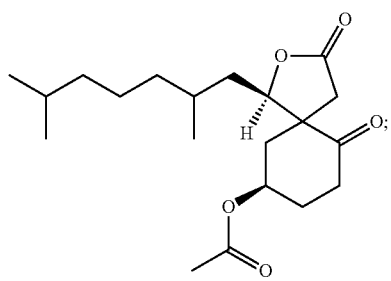

Hexahydro-miliusate

-continued
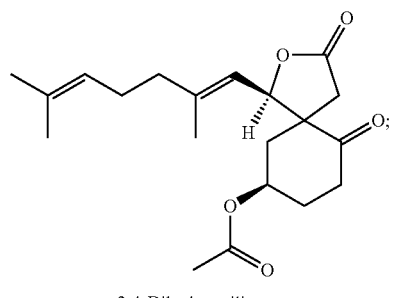
3,4-Dihydro-miliusate
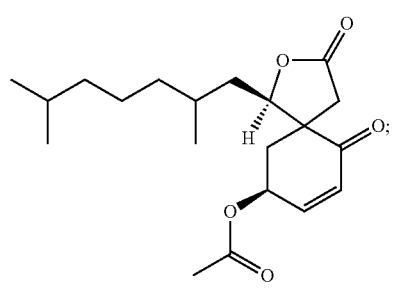
2′,3′,6′,7′-Tetrahydro-miliusate
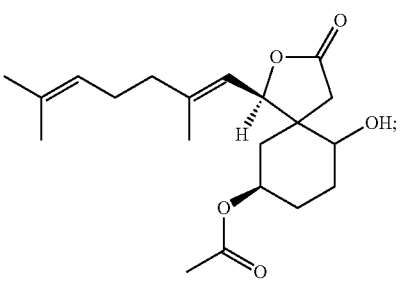
2-Hydroxy-3,4-dihydro-miliusate
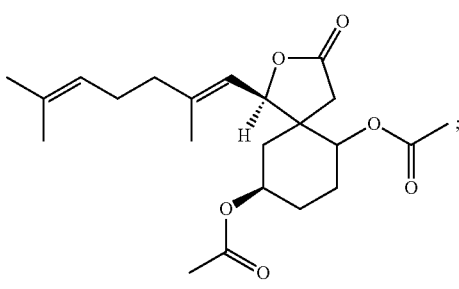
2-Acetoxy-3,4-dihydro-miliusate
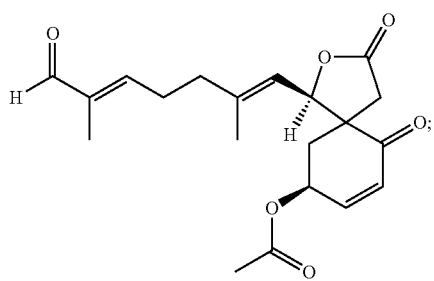
8′-Oxo-miliusate
-continued
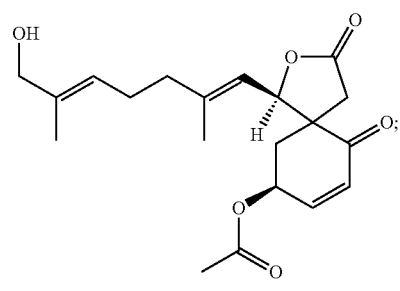
8′-Hydroxy-miliusate
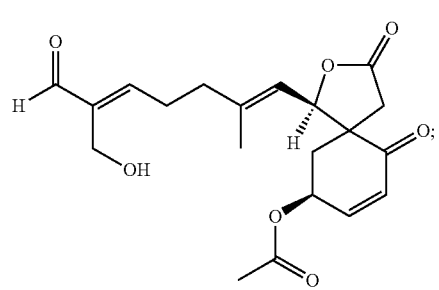
10′-Hydroxy-8′-oxo-miliusate
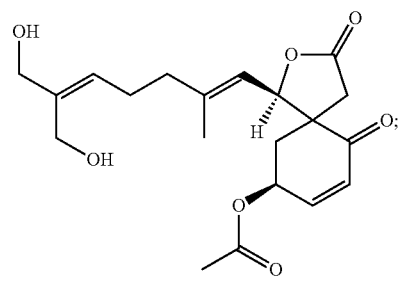
8′,10′-Dihydroxy-miliusate
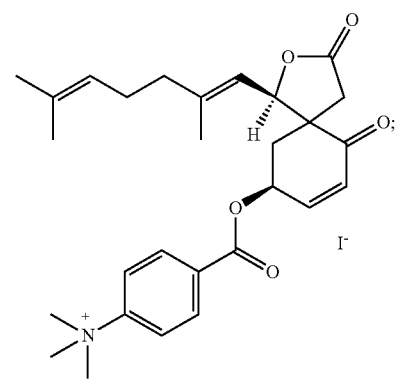
5β-(p-Trimethylammonio-benzyol)miliusol iodide -continued

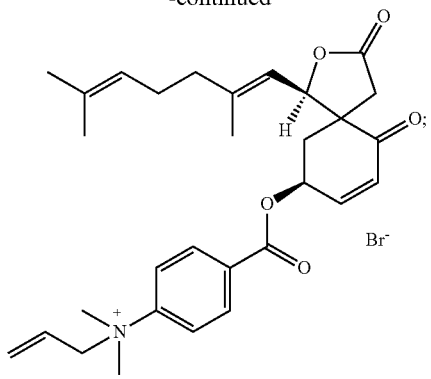

5β-(p-Dimethyl-allyl-ammonio-benzyol)miliusol bromide

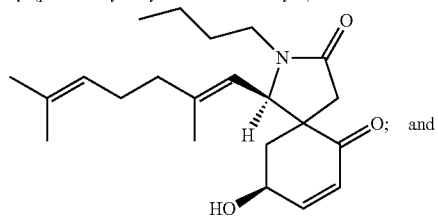

N-(n-Butyl)-miliusol lactam

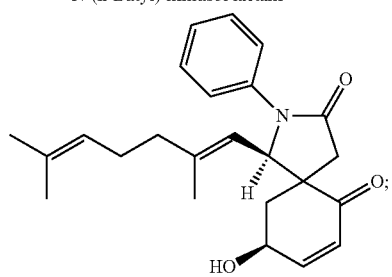

N-Phenyl-miliusol lactam or a pharmaceutically acceptable salt or prodrug thereof.

In an eighth embodiment of the first aspect of the present disclosure, there is provided a method, wherein said viral infection is influenza or HIV.

In a ninth embodiment of the first aspect of the present disclosure, there is provided a method, wherein said viral infection is influenza A.

In a tenth embodiment of the first aspect of the present disclosure, there is provided a method, wherein said viral infection is H5N1.

In an eleventh embodiment of the first aspect of the present disclosure, there is provided a method, wherein said viral infection is influenza A and said compound of Formula (I) inhibits the viral entry of influenza A to a host cell.

In a twelfth embodiment of the first aspect of the present disclosure, there is provided a method, wherein said viral infection is influenza A, said compound of Formula (I) inhibits the viral entry of influenza A to a host cell, and said compound of Formula (I) is miliusane I.

In a thirteenth embodiment of the first aspect of the present disclosure, there is provided a method, wherein said viral infection is HIV and said compound of Formula (I) inhibits the viral replication of the HIV virus.

In a fourteenth embodiment of the first aspect of the present disclosure, there is provided a method, wherein said viral infection is HIV and said compound of Formula (I) has Formula (IC):

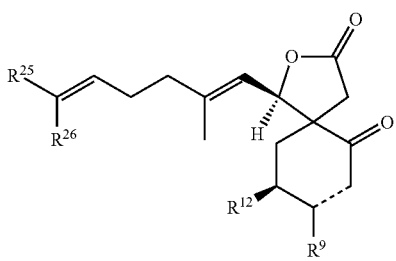

or a pharmaceutically acceptable salt or prodrug thereof, wherein a dashed line represents a single or double bond;

$R^9$ is hydrogen or —N($R^{17}$)$R^{18}$;

$R^{12}$ is hydroxyl, —O(C═O)alkyl;

$R^{17}$ is hydrogen;

$R^{18}$ is aryl optionally substituted with one or two $R^{20}$;

$R^{20}$ is independently selected from the group consisting of halogen, nitro, hydroxyl and alkyl; and each of $R^{25}$ and $R^{26}$ is independently selected from the group consisting of methyl, —CH$_2$OH, and C(═O)H.

In a fifteenth embodiment of the first aspect of the present disclosure, there is provided a method, wherein said compound of Formula (IC) is selected from the group consisting of:

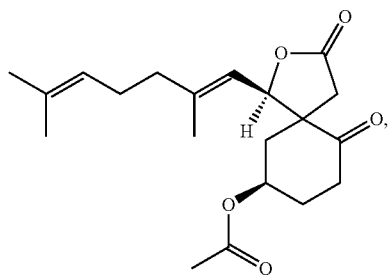

3,4-Dihydro-miliusate

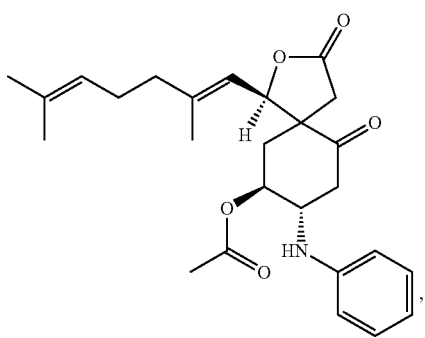

4α-(N-Phenyl)miliusate

-continued

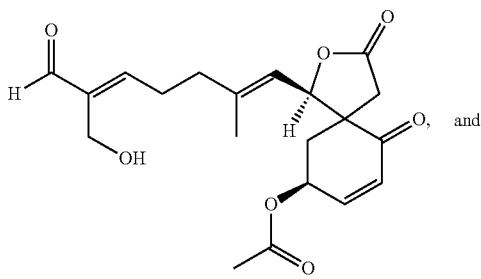

10′-Hydroxy-8′-oxo-miliusate

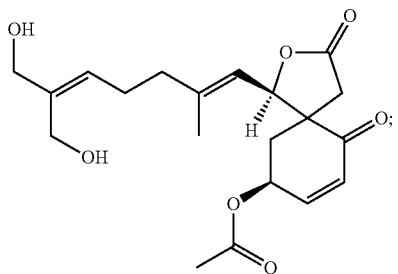

8′,10′-Dihydroxy-miliusate or a pharmaceutically acceptable salt or prodrug thereof.

In a sixteenth embodiment of the first aspect of the present disclosure, there is provided a method, wherein said subject is human.

In a seventeenth embodiment of the first aspect of the present disclosure, there is provided a method, wherein said subject is human and the viral infection is HIV and the compound of Formula (I) is selected from the group consisting of:

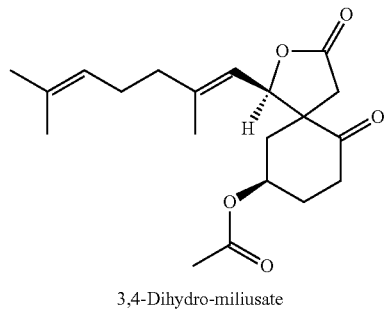

3,4-Dihydro-miliusate

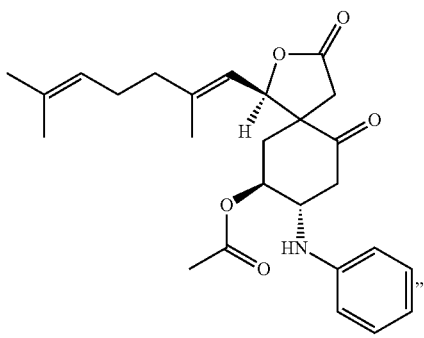

4α-(N-Phenyl)miliusate

-continued

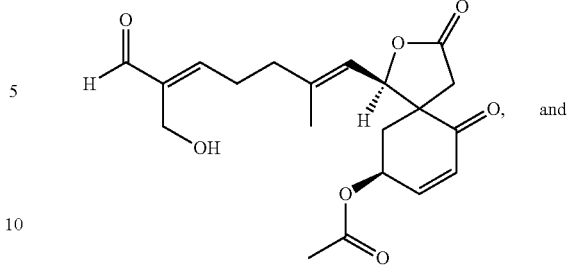

10′-Hydroxy-8′-oxo-miliusate

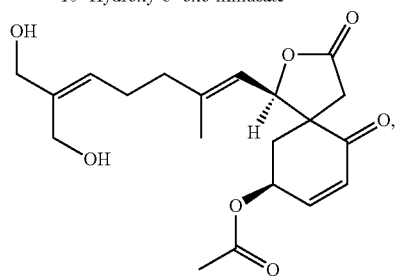

8′,10′-Dihydroxy-miliusate wherein the compound is administered at a dosage of 3.2 mg per kilogram of body weight of the human.

In an eighteenth embodiment of the first aspect of the present disclosure, there is provided a method, wherein said subject is human, the viral infection is HIV, and the compound of Formula (I) is 4α-(N-phenyl)miliusate.

Compounds of the present invention may exist in different forms, such as free acids, free bases, substantially enantiomerically pure form, racemic mixtures, diastereomeric mixtures, esters and prodrugs, salts, and tautomers, and the disclosure includes all variant forms of these compounds.

Features, integers, characteristics, compounds, chemical moieties or groups described in conjunction with a particular aspect, embodiment or example of the present invention are to be understood to be applicable to any other aspect, embodiment or example described herein unless incompatible therewith.

Those skilled in the art will appreciate that the methods and compositions described herein are susceptible to variations and modifications other than those specifically described.

The present disclosure includes all such variations and modifications. The present disclosure also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the present invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the present disclosure and apply throughout. Unless otherwise defined, all other technical terms used herein have the same meaning as commonly understood to one of ordinary skill in the art to which the present disclosure belongs.

Other aspects and advantages of the present invention will be apparent to those skilled in the art from a review of the ensuing description.

DETAILED DESCRIPTION OF INVENTION

The present disclosure is not to be limited in scope by any of the specific embodiments described herein. The following embodiments are presented for exemplification only.

DEFINITIONS

Miliusane and Core Structures

The term "miliusane" as used herein includes reference to a compound comprising the basic structure shown as below:

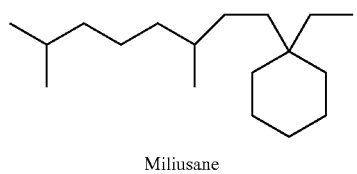 [SMILES: CCC1(CCC(C)CCCC(C)C)CCCCC1]

Miliusane

The carbon numbering of miliusane molecule as used herein includes reference to a compound comprising numbering system shown as below:

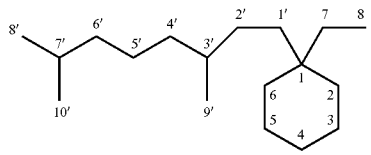

The term "the core structure of miliusane" as used herein includes reference to a compound comprising the basic structure shown as below:

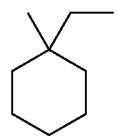

The core structure of miliusane

In one class of the core structures of miliusane compounds, the methyl group and the ethyl group form a tetrahydrofuran ring (1-oxa-spiro [4.5] decane and 2-oxa-spiro [4.5] decane).

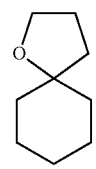 

1-Oxa-spiro[4.5]decane    2-Oxa-spiro[4.5]decane

In the second class of the core structures of miliusane compounds, the methyl group and the ethyl group form a tetrahydro-thiophene ring (1-thia-spiro [4.5] decane and 2-thia-spiro [4.5] decane).

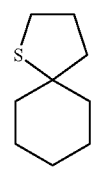 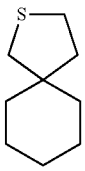

1-Thia-spiro[4.5]decane    2-Thia-spiro[4.5]decane

In the third class of the cores structure of miliusane compounds, the methyl group and the ethyl group form a pyrrolidine ring (1-aza-spiro [4.5] decane, 2-aza-spiro [4.5] decane, 1-aza-spiro [4.5] dec-1-ene, 2-aza-spiro [4.5] dec-1-ene and 2-aza-spiro [4.5] dec-2-ene).

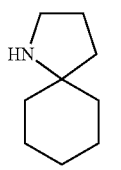 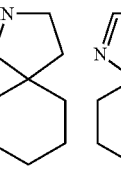 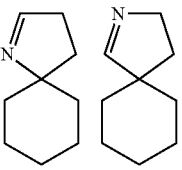  

| 1-Aza-spiro [4.5]decane | 2-Aza-spiro [4.5]decane | 1-Aza-spiro[4.5] dec-1-ene | 2-Aza-spiro[4.5] dec-1-ene | 2-Aza-spiro[4.5] dec-2-ene |

Hydrocarbyl

The term "hydrocarbyl" as used herein includes reference to a moiety consisting of hydrogen and carbon atoms; such a moiety may comprise an aliphatic and/or an aromatic moiety. The moiety may comprise 1, 2, 3, 4, 5, 6, 7, 8, 9, 10, 11, 12, 13, 14, 15, 16, 17, 18, 19 or 20 carbon atoms. Examples of hydrocarbyl groups include $C_{1-6}$ alkyl (e.g., $C_1$, $C_2$, $C_3$ or $C_4$ alkyl, for example methyl, ethyl, propyl, isopropyl, n-butyl, sec-butyl or tert-butyl); $C_{1-6}$ alkyl substituted by aryl (e.g., benzyl); cycloalkyl (e.g., cyclopropylmethyl); cycloalkyl (e.g., cyclopropyl, cyclobutyl, cyclopentyl or cyclohexyl); aryl (e.g., phenyl, naphthyl or fluorenyl) or by alkenyl groups (e.g., $C_2$-$C_{10}$ alkenyl, $C_4$-$C_{10}$ alkenyl, or $C_6$-$C_{10}$ alkenyl) and the like. In certain embodiments, hydrocarbyl includes reference to the following moieties:

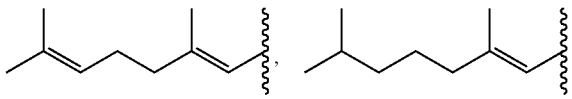

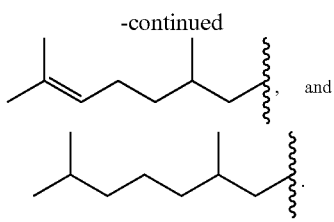

Alkyl

The terms "alkyl" and "$C_{1-9}$ alkyl" as used herein include reference to a straight or branched chain alkyl moiety having 1, 2, 3, 4, 5, 6, 7, 8, or 9 carbon atoms. This term includes reference to groups, such as methyl, ethyl, propyl (n-propyl or isopropyl), butyl (n-butyl, sec-butyl or tert-butyl), pentyl, hexyl and the like. In particular, the alkyl moiety may have 1, 2, 3 or 4 carbon atoms.

Alkenyl

The terms "alkenyl" and "$C_{2-10}$ alkenyl" as used herein include reference to a straight or branched chain alkyl moiety having 2, 3, 4, 5, 6, 7, 8, 9, or 10 carbon atoms and having, in addition, at least one double bond, of either E or Z stereochemistry where applicable. This term includes reference to groups, such as ethenyl, 2-propenyl, 1-butenyl, 2-butenyl, 3-butenyl, 1-pentenyl, 2-pentenyl, 3-pentenyl, 1-hexenyl, 2-hexenyl, 3-hexenyl, and the like.

Alkynyl

The terms "alkynyl" and "$C_{2-6}$ alkynyl" as used herein include reference to a straight or branched chain alkyl moiety having 2, 3, 4, 5 or 6 carbon atoms and having, in addition, at least one triple bond. This term includes reference to groups, such as ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl, 3-hexynyl, and the like.

Alkoxy

The terms "alkoxy" and "$C_{1-6}$ alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups, such as methoxy, ethoxy, propoxy, isopropoxy, butoxy, tert-butoxy, pentoxy, hexoxy and the like.

Cycloalkyl

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups, such as cyclopropyl, cyclobutyl, cyclopentyl, cyclohexyl, norbornyl, bicyclo[2.2.2]octyl, and the like.

Aryl

The term "aryl" as used herein includes reference to an aromatic ring system comprising 6, 7, 8, 9, 10, 11, 12, 13, 14, 15 or 16 ring carbon atoms. Aryl is often phenyl but may be a polycyclic ring system, having two or more rings, at least one of which is aromatic. This term includes reference to groups, such as phenyl, naphthyl, fluorenyl, azulenyl, indenyl, anthryl, and the like.

Cyclic Group

"Cyclic group" means a ring or ring system, which may be unsaturated or partially unsaturated but is usually saturated, typically containing 3 to 13 ring-forming atoms, for example a 3-, 4-, 5- or 6-membered ring. The ring system may be a bridged or polycyclic ring system. The ring or ring system may be substituted with one or more hydrocarbyl groups. Cyclic groups includes carbocyclyl and heterocyclyl moieties.

Carbocyclyl

The term "carbocyclyl" as used herein includes reference to a saturated (e.g., cycloalkyl) or unsaturated (e.g., aryl) ring moiety having 3, 4, 5, 6, 7, 8, 9, 10, 11, 12, 13, 14, 15 or 16 carbon ring atoms. In particular, carbocyclyl includes a 3- to 10-membered ring or ring system and, in particular, 5- or 6-membered rings, which may be saturated or unsaturated. The ring or ring system may be substituted with one or more hydrocarbyl groups. A carbocyclic moiety is, for example, selected from cyclopropyl, cyclobutyl, cyclopentyl, cyclohexyl, norbornyl, bicyclo[2.2.2]octyl, phenyl, naphthyl, fluorenyl, azulenyl, indenyl, anthryl, and the like.

Heterocyclyl

The term "heterocyclyl" as used herein includes reference to a non-aromatic (e.g., heterocycloalkyl) or an aromatic (e.g., heteroaryl) heterocyclic ring moiety having from 3, 4, 5, 6, 7, 8, 9, 10, 11, 12, 13, 14, 15 or 16 ring atoms, at least one of which is selected from nitrogen, oxygen, phosphorus, silicon and sulfur. In particular, heterocyclyl includes a 3- to 10-membered ring or ring system and more particularly a 5- or 6-membered ring, which may be saturated or unsaturated. The ring or ring system may be substituted with one or more hydrocarbyl groups.

A heterocyclic moiety is, for example, selected from oxiranyl, azirinyl, 1, 2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, pyrrolizidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4/V-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazoiyl, β-carbolinyl, phenanthridinyl, acridinyl, perimidinyl, phenanthrolinyl, furazanyl, phenazinyl, phenothiazinyl, phenoxazinyl, chromenyl, isochromanyl, chromanyl, and the like.

Heterocycloalkyl

The term "heterocycloalkyl" as used herein includes reference to a heterocyclic moiety having 3, 4, 5, 6 or 7 ring carbon atoms and 1, 2, 3, 4, or 5 ring heteroatoms selected from nitrogen, oxygen, phosphorus and sulfur. Heterocycloalkyl can have one or more carbon-carbon double bonds or carbon-heteroatoms double bonds as long as the ring is not aromatic. The group may be a polycyclic ring system but more often is monocyclic. This term includes reference to groups, such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl, and the like. The ring or ring system may be substituted with one or more hydrocarbyl groups.

Heteroaryl

The term "heteroaryl" as used herein includes reference to an aromatic heterocyclic ring system having 5, 6, 7, 8, 9, 10, 11, 12, 13, 14, 15 or 16 ring atoms, at least one of which is selected from nitrogen, oxygen and sulfur. The group may be a polycyclic ring system, having two or more rings, at least one of which is aromatic, but is more often monocyclic. The ring or ring system may be substituted with one or more hydrocarbyl groups. This term includes reference to groups, such as pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl, and the like.

Halogen

The term "halogen" as used herein includes reference to F, Cl, Br, or I.

Halogen Containing Moiety

The expression "halogen containing moiety" as used herein includes reference to a moiety comprising 1 to 30 plural valence atoms selected from carbon, nitrogen, oxygen and sulfur which moiety includes at least one halogen. The moiety may be hydrocarbyl for example $C_{1-6}$ alkyl or $C_{1-6}$ alkoxy, or carbocyclyl for example aryl.

Substituted

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or un-substituted. It will, of course, be understood that substituents are only at positions where they are chemically possible, the person skilled in the art being able to decide (either experimentally or theoretically) without inappropriate effort whether a particular substitution is possible.

Enantiomer

The term "enantiomer" as used herein means one of two stereoisomers that are non-superimposable mirror images of one another.

Racemate

The term "racemate" as used herein means a mixture of equal amounts of enantiomers of a chiral molecule.

Diastereomer

The term "diastereomer" as used herein means one of a class of stereoisomers that are not enantiomers, but that have different configurations at one or more of the equivalent chiral centers. Example of diasteromers are epimers that differ in configuration of only one chiral center.

Stereoisomer

The term "stereoisomer" as used herein means one of a class of isomeric molecules that have the same molecular formula and sequence of bonded atoms, but different three-dimensional orientations of their atoms in space.

Tautomers

The term "tautomer" means isomeric molecules that readily interconvert by a chemical reaction. The reaction commonly results in the migration of a hydrogen atom, which results in a switch of a single bond and adjacent double bond.

Prodrug

A prodrug is a medication that is administered as an inactive (or less than fully active) chemical derivative that is subsequently converted to an active pharmacological agent in the body, often through normal metabolic processes.

Independently

Where two or more moieties are described as being "each independently" selected from a list of atoms or groups, this means that the moieties may be the same or different. The identity of each moiety is therefore independent of the identities of the one or more other moieties.

Embodiments of the present invention are described below. Preferred features of each aspect of the present invention are as for each of the other aspects mutatis mutandis. Moreover, it will be appreciated that the features specified in each embodiment may be combined with other specified features, to provide further embodiments.

The term "treat" or "treatment" as used herein refers to any type of treatment that imparts a benefit to a patient afflicted with a disease, including improvement in the condition of the patient (e.g., in one or more symptoms), delay in the progression of the condition, etc. In certain embodiments, the treatment of an HIV or influenza infection results in at least an inhibition/reduction in the number of infected cells.

The term "inhibit" in the context of inhibiting a viral infection may refer to the reduction in the incidence of or the symptoms of the viral infection being treated or the presence or extent of the viral infection being treated.

As used herein, the term "prevent" refers to the prophylactic treatment of a subject who is at risk of developing a condition resulting in a decrease (e.g., at least a significant decrease) in the probability that the subject will develop the condition. In certain embodiments, the treatment of an HIV or influenza infection results in a decrease in the probability that the subject will develop or contrast an HIV or an influenza infection.

Compounds of the Present Disclosure

In an exemplary embodiment, the present disclosure relates to compounds of formula (I) or (II) useful for treating viral infections:

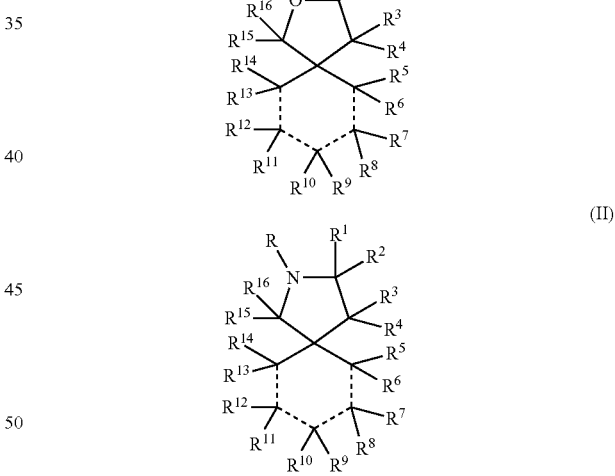

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are each independently selected from hydrogen, halogen or a moiety comprising 1 to 30 plural valence atoms selected from carbon, nitrogen, oxygen and sulfur; or these groups may be taken together with the carbon atoms to which they are attached to form one or more cyclic groups which is optionally substituted with halogen or a moiety comprising 1 to 30 plural valence atoms selected from carbon, nitrogen, oxygen and sulfur; $R^1$ and $R^2$, $R^3$ and $R^4$, $R^5$ and $R^6$, $R^7$ and $R^8$, $R^9$ and $R^{10}$, $R^{11}$ and $R^{12}$, $R^{13}$ and $R^{14}$ or $R^{15}$ and $R^{16}$ may be taken together with the carbon atoms to which they are attached to form one or more carboxyl groups (C=O); or while one of $R^1$ and $R^2$, $R^3$ and $R^4$, $R^5$ and $R^6$, $R^7$ and $R^8$, $R^9$ and $R^{10}$, $R^{11}$ and $R^{12}$, $R^{13}$ and $R^{14}$ or $R^{15}$ and $R^{16}$ is hydrogen, halogen, hydrocarbyl or alkoxy, the other one of $R^1$ and $R^2$, $R^3$ and $R^4$, $R^5$ and $R^6$, $R^7$ and $R^8$, $R^9$ and $R^{10}$, $R^{11}$ and $R^{12}$, $R^{13}$ and $R^{14}$ or $R^{15}$ and $R^{16}$ is selected from $R^{17}$, —C(O)$R^{17}$ and —C(O)O$R^{17}$; $R^{17}$ is independently selected from hydrogen, halogen, trifluoromethyl, cyano, nitro, hydrocarbyl optionally substituted with 1, 2, 3, 4 or 5 $R^{18}$, heterocyclyl optionally substituted with 1, 2, 3, 4 or 5 $R^{18}$, —(CH$_2$)$_k$-heterocyclyl optionally substituted with 1, 2, 3, 4 or 5 $R^{18}$, —O$R^{19}$, —C(O)$R^{20}$, —C(O)N($R^{19}$)$R^{20}$, —C(O)O$R^{19}$, —OC(O)$R^{19}$, —S(O)$_2$$R^{19}$, —S(O)$_2$N($R^{19}$)$R^{20}$, —N($R^{19}$)$R^{20}$, —N($R^{19}$)N($R^{19}$)$R^{20}$, —N($R^{19}$)C(O)$R^{20}$ and —N($R^{19}$)S(O)$_2$$R^{20}$; wherein k is an integer between 1 and 6 (e.g., 1, 2 or 3); $R^{18}$ is independently selected from halogen, trifluoromethyl, cyano, nitro, oxo, =N$R^{19}$, —O$R^{19}$, —C(O)$R^{20}$, —C(O)N($R^{19}$)$R^{20}$, —C(O)O$R^{19}$, —OC(O)$R^{20}$, —S(O)$_2$$R^{19}$, —S(O)$_2$N($R^{19}$)$R^{20}$, —N($R^{19}$)$R^{20}$, —N($R^{19}$)$R^{20}$, —N($R^{19}$)C(O)$R^{20}$ and —N($R^{19}$)S(O)$_2$$R^{20}$; $R^{19}$ and $R^{20}$ are each independently hydrogen or selected from hydrocarbyl, heterocyclyl or —(CH$_2$)$_k$-heterocyclyl, which is optionally substituted with 1, 2, 3, 4 or 5 substituents independently selected from halogen, cyano, amino, hydroxy, C$_{1-6}$ alkyl and C$_{1-6}$ alkoxy; wherein k is an integer between 1 and 6 (e.g., 1, 2 or 3); X is oxygen or sulfur; R is hydrogen or selected from hydrocarbyl, heterocyclyl or —(CH$_2$)$_k$-heterocyclyl, which is optionally substituted with 1, 2, 3, 4 or 5 substituents independently selected from halogen, cyano, amino, hydroxy, C$_{1-6}$ alkyl and C$_{1-6}$ alkoxy; wherein k is an integer between 1 and 6 (e.g., 1, 2 or 3); dashed line "- - - -" denotes a single or double bond; or a pharmaceutically acceptable salt or prodrug thereof.

In certain embodiments, the present disclosure relates to compounds of Formula (I) or Formula (II) that exhibit anti-viral activity as described herein, wherein said compound of Formula (I) and said compound of Formula (II) can represented by:

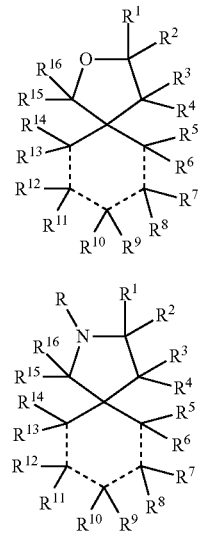

or a pharmaceutically acceptable salt or prodrug thereof, wherein a
dashed line represents a single or double bond;
$R^1$ and $R^2$ are hydrogen; or taken together with the carbon atoms to which they are attached to form a carboxyl group (C=O);

each of $R^3$ and $R^4$ are independently selected from the group consisting of hydrogen, halogen, and hydroxy; or $R^3$ and $R^4$ taken together with the carbon atoms to which they are attached to form a carboxyl group (C=O);

each of $R^5$ and $R^6$ are independently selected from the group consisting of hydrogen, halogen, and —O$R^{19}$; or $R^5$ and $R^6$ taken together with the carbon atoms to which they are attached to form a carboxyl group (C=O);

each pair of the substituted groups $R^7$ and $R^8$, $R^9$ and $R^{10}$, or $R^{11}$ and $R^{12}$ is independently taken together with the carbon atoms to which they are attached to form one or more carboxyl groups (C=O); or while one substituent of $R^7$ and $R^8$, one substituent of $R^9$ and $R^{10}$, or one substituent of $R^{11}$ and $R^{12}$ is hydrogen or halogen whereas the other substituent of $R^7$ and $R^8$, the other substituent of $R^9$ and $R^{10}$, or the other substituent of $R^{11}$ and $R^{12}$ is selected from —N($R^{17}$)$R^{18}$ or —N($R^{17}$)C(=O)$R^{18}$; or while one substituent of $R^7$ and $R^8$, one substituent of $R^9$ and $R^{10}$, or one substituent of $R^{11}$ and $R^{12}$ is hydrogen or halogen whereas the other substituent of $R^7$ and $R^8$, the other substituent of $R^9$ and $R^{10}$, or the other substituent of $R^{11}$ and $R^{12}$ is selected from hydrogen and —O$R^{19}$;

$R^{13}$ and $R^{14}$ are independently selected from the group consisting of hydrogen and —O$R^{19}$; or $R^{13}$ and $R^{14}$ taken together with the carbon atoms to which they are attached to form a carboxyl group (C=O);

$R^{15}$ and $R^{16}$ are independently selected from the group consisting of hydrogen and hydrocarbyl, wherein said hydrocarbyl has at least five carbons, and may be optionally substituted with one, two, or three substituents independently selected from hydroxy, halogen, aldehyde group (H—C=O), C(=O)OH, C$_{1-6}$ alkyl and C$_{1-6}$ alkoxy;

each instance of $R^{17}$ and $R^{18}$ are independently selected from hydrogen, hydrocarbyl optionally substituted with one, two, three, four or five $R^{20}$, heterocyclyl optionally substituted with one, two, three, four or five $R^{20}$ and —(CH$_2$)$_k$-heterocyclyl optionally substituted with one, two, three, four or five $R^{20}$;

$R^{19}$ is selected from $R^{21}$ and —C(=O)$R^{21}$;

each instance of $R^{20}$ is independently selected from the group consisting of halogen, cyno, nitro, —$R^{22}$, —O$R^{22}$, —C(=O)$R^{23}$, —C(=O)N($R^{22}$)$R^{23}$, —C(=O)O$R^{22}$, —OC(=O)$R^{23}$, —N($R^{22}$)$R^{23}$, —N($R^{22}$)C(=O)$R^{23}$, —N($R^{22}$)($R^{23}$)$R^{24}$, —S$R^{22}$, —S(=O)$R^{23}$, —S(O)$_2$$R^{23}$, —S(O)$_2$N($R^{22}$)$R^{23}$, and —N($R^{22}$)S(O)$_2$$R^{23}$;

$R^{21}$ is selected from hydrogen, heterocyclyl optionally substituted with one, two, three, four or five $R^{20}$, hydrocarbyl optionally substituted with one, two, three, four or five $R^{20}$, heteroaryl optionally substituted with one, two, three, four or five $R^{20}$, and —(CH$_2$)$_k$-heterocyclyl optionally substituted with one, two, three, four or five $R^{20}$;

each instance of k is independently selected from an integer selected between 1 and 6;

$R^{22}$, $R^{23}$ and $R^{24}$ are each independently selected from hydrogen, or hydrocarbyl and heterocyclyl, either of which is optionally substituted with one, two, three, four or five substituents independently selected from halogen, cyano, amino, hydroxy, C$_{1-6}$ alkyl and C$_{1-6}$ alkoxy; and R is selected from hydrogen and hydrocarbyl.

In certain embodiments, the compound of Formula (I) has Formula (IA):

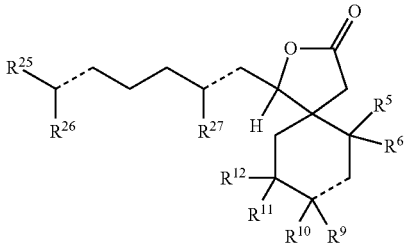

IA or a pharmaceutically acceptable salt or prodrug thereof, wherein a dashed line represents a single or double bond;

$R^5$ and $R^6$ are each independently selected from the group consisting of hydrogen and —$OR^{19}$; or $R^5$ and $R^6$ taken together with the carbon to which they are attached form a carboxyl group (C=O);

while one substituent of $R^9$ and $R^{10}$, or one substituent of $R^{11}$ and $R^{12}$ is hydrogen or halogen whereas the other substituent of $R^9$ and $R^{10}$, or the other substituent of $R^{11}$ and $R^{12}$ is selected from —$N(R^{17})R^{18}$ or —$N(R^{17})C(=O)R^{18}$; or while one substituent of $R^9$ and $R^{10}$, or one substituent of $R^{11}$ and $R^{12}$ is hydrogen or halogen whereas the other substituent of $R^9$ and $R^{10}$, or the other substituent of $R^{11}$ and $R^{12}$ is selected from hydrogen and —$OR^{19}$;

each of $R^{17}$ and $R^{18}$ is independently selected from hydrogen, heterocyclyl optionally substituted with one to five $R^{20}$, and hydrocarbyl optionally substituted with one to five $R^{20}$;

$R^{19}$ is selected from $R^{21}$ and —$C(=O)R^{21}$;

$R^{20}$ is independently selected from the group consisting of halogen, nitro, —$R^{22}$, —$OR^{22}$, —$C(=O)R^{23}$, —$C(=O)N(R^{22})R^{23}$, —$OC(=O)R^{23}$, —$N(R^{22}(R^{23}$, —$N(R^{22})C(=O)R^{23}$, and —$N(R^{22})(R^{23})(R^{24})$;

$R^{21}$ is selected from hydrogen, heterocyclyl optionally substituted with one to five $R^{20}$, and hydrocarbyl optionally substituted with one to five $R^{20}$;

$R^{22}$, $R^{23}$ and $R^{24}$ are each independently selected from hydrogen, hydrocarbyl and heterocyclyl; and each of $R^{25}$, $R^{26}$, and $R^{27}$ is independently selected from the group consisting of methyl, —$CH_2OH$, C(=O)H, and C(=O)OH.

In certain embodiments, the compound of Formula (I) has Formula (IB):

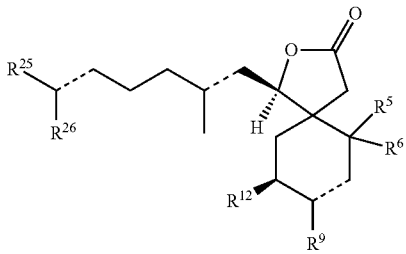

IB or a pharmaceutically acceptable salt or prodrug thereof, wherein a dashed line represents a single or double bond;

$R^5$ and $R^6$ are each independently selected from the group consisting of hydrogen and —$OR^{19}$; or $R^5$ and $R^6$ taken together with the carbon to which they are attached form a carboxyl group (C=O);

$R^9$ is hydrogen, —$N(R^{17})R^{18}$, —$N(R^{17})C(=O)R^{18}$, or —$OR^{19}$;

$R^{12}$ is hydrogen or —$OR^{19}$;

each of $R^{17}$ and $R^{18}$ is independently selected from hydrogen, heterocyclyl optionally substituted with one to five $R^{20}$, and hydrocarbyl optionally substituted with one to five $R^{20}$;

$R^{19}$ is selected from $R^{21}$ and —$C(=O)R^{21}$;

$R^{20}$ is independently selected from the group consisting of halogen, nitro, —$R^{22}$, —$OR^{22}$, —$C(=O)R^{23}$, —$C(=O)N(R^{22})R^{23}$, —$OC(=O)R^{23}$, —$N(R^{22})R^{23}$, —$N(R^{22})C(=O)R^{23}$, and —$N(R^{22})(R^{23})R^{24}$;

$R^{21}$ is selected from hydrogen, heterocyclyl optionally substituted with one to five $R^{20}$, and hydrocarbyl optionally substituted with one to five $R^{20}$;

$R^{22}$, $R^{23}$ and $R^{24}$ are each independently selected from hydrogen, hydrocarbyl and heterocyclyl; and each of $R^{25}$ and $R^{26}$ is independently selected from the group consisting of methyl, —$CH_2OH$, C(=O)H, and C(=O)OH.

In certain embodiments, the compound of Formula (I) can be represented by Formula (IB):

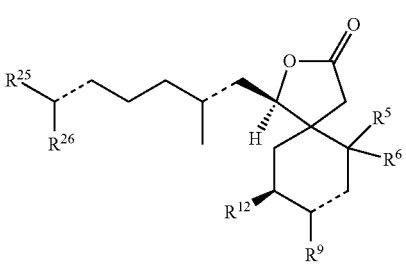

IB or a pharmaceutically acceptable salt or prodrug thereof, wherein a dashed line represents a single or double bond;

$R^5$ and $R^6$ are each independently selected from the group consisting of hydrogen, hydrocarbyl, hydroxyl, and —$OC(=O)R^{21}$; or $R^5$ and $R^6$ taken together with the carbon to which they are attached form a carboxyl group (C=O);

$R^9$ is hydrogen, —$N(R^{17})R^{18}$, —$N(R^{17})C(=O)R^{18}$, or —$OR^{19}$;

$R^{12}$ is hydroxyl, —O-hydrocarbyl, or —$OC(=O)R^{21}$;

each of $R^{17}$ and $R^{18}$ is independently selected from hydrogen, aryl optionally substituted with one or two $R^{20}$;

$R^{19}$ is selected from $R^{21}$ and —$C(=O)R^{21}$;

$R^{20}$ is independently selected from the group consisting of halogen, nitro, —$R^{22}$, —$OR^{22}$, —$C(=O)R^{23}$, —$C(=O)N(R^{22})R^{23}$, —$OC(=O)R^{23}$, —$N(R^{22})C(=O)R^{23}$, and —$N(R^{22})(R^{23})R^{24}$;

$R^{21}$ is hydrocarbyl, wherein the hydrocarbyl is substituted with one or two $R^{20}$; and each of $R^{25}$ and $R^{26}$ is independently selected from the group consisting of methyl, —$CH_2OH$, and C(=O)H.

In certain embodiments, the compound of Formula (I) can be represented by Formula (IB), wherein $R^5$ is hydrogen and $R^6$ is hydroxyl or —$OC(=O)$alkyl; or $R^5$ and $R^6$ taken together with the carbon to which they are attached form a carboxyl group (C=O);

$R^9$ is hydrogen, —N($R^{17}$)$R^{18}$, —N($R^{17}$)C(=O)$R^{18}$, or —O-alkyl;

$R^{12}$ is hydroxyl or —C(=O)$R^{21}$;

each of $R^{17}$ and $R^{18}$ is independently selected from hydrogen, aryl optionally substituted with one $R^{20}$; and $R^{21}$ is alkyl or aryl optionally substituted with one $R^{20}$.

In certain embodiments, the compound of Formula (I) can be represented by Formula (IB), wherein $R^5$ is hydrogen and $R^6$ is hydroxyl or —OC(=O)alkyl; or $R^5$ and $R^6$ taken together with the carbon to which they are attached form a carboxyl group (C=O);

$R^9$ is hydrogen, —N($R^{17}$)$R^{18}$, —N($R^{17}$)C(=O)$R^{18}$, or —O$R^{19}$;

$R^{12}$ is hydrogen or —O$R^{19}$;

each of $R^{17}$ and $R^{18}$ is independently selected from hydrogen and hydrocarbyl optionally substituted with one to five $R^{20}$;

$R^{19}$ is selected from $R^{21}$ and —C(=O)$R^{21}$;

$R^{20}$ is independently selected from the group consisting of halogen, nitro, —$R^{22}$, —O$R^{22}$, —N($R^{22}$)$R^{23}$, —N($R^{22}$)($R^{23}$)$R^{24}$;

$R^{21}$ is selected from hydrogen and hydrocarbyl optionally substituted with one to five $R^{20}$;

$R^{22}$, $R^{23}$ and $R^{24}$ are each independently selected from hydrogen and alkyl; and each of $R^{25}$ and $R^{26}$ is independently selected from the group consisting of methyl, —CH$_2$OH, C(=O)H, and C(=O)OH.

In certain embodiments, the compound of Formula (II) has Formula (IIA):

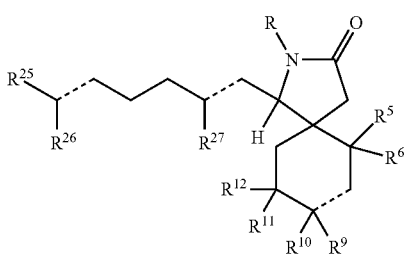

IIA or a pharmaceutically acceptable salt or prodrug thereof, wherein a dashed line represents a single or double bond;

R is hydrogen, alkyl, aryl, or $C_{1-6}$ alkyl substituted by aryl.

$R^5$ and $R^6$ are each independently selected from the group consisting of hydrogen and —O$R^{19}$; or $R^5$ and $R^6$ taken together with the carbon to which they are attached form a carboxyl group (C=O);

while one substituent of $R^9$ and $R^{10}$, or one substituent of $R^{11}$ and $R^{12}$ is hydrogen or halogen whereas the other substituent of $R^9$ and $R^{10}$, or the other substituent of $R^{11}$ and $R^{12}$ is selected from —N($R^{17}$)$R^{18}$ or —N($R^{17}$)C(=O)$R^{18}$; or while one substituent of $R^9$ and $R^{10}$, or one substituent of $R^{11}$ and $R^{12}$ is hydrogen or halogen whereas the other substituent of $R^9$ and $R^{10}$, or the other substituent of $R^{11}$ and $R^{12}$ is selected from hydrogen and —O$R^{19}$;

each of $R^{17}$ and $R^{18}$ is independently selected from hydrogen, heterocyclyl optionally substituted with one to five $R^{20}$, and hydrocarbyl optionally substituted with one to five $R^{20}$;

$R^{19}$ is selected from $R^{21}$ and —C(=O)$R^{21}$;

$R^{20}$ is independently selected from the group consisting of halogen, nitro, —$R^{22}$, —O$R^{22}$, —C(=O)$R^{23}$, —C(=O)N($R^{22}$)$R^{23}$, —OC(=O)$R^{23}$, —N($R^{22}$)$R^{23}$, —N($R^{22}$)C(=O)$R^{23}$, and —N($R^{22}$)($R^{23}$)($R^{24}$);

$R^{21}$ is selected from hydrogen, heterocyclyl optionally substituted with one to five $R^{20}$, and hydrocarbyl optionally substituted with one to five $R^{20}$;

$R^{22}$, $R^{23}$ and $R^{24}$ are each independently selected from hydrogen, hydrocarbyl and heterocyclyl;

each of $R^{25}$, $R^{26}$, and $R^{27}$ is independently selected from the group consisting of methyl, C(=O)H, and C(=O)OH.

In certain embodiments, the compound of Formula (II) has Formula (IIB):

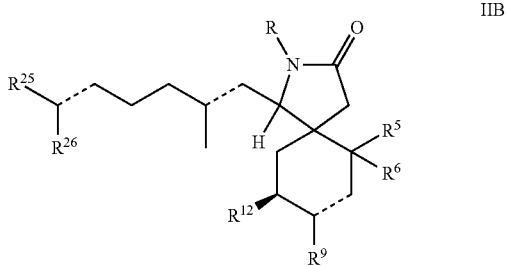

IIB or a pharmaceutically acceptable salt or prodrug thereof, wherein a dashed line represents a single or double bond;

R is hydrogen, alkyl, aryl, or $C_{1-6}$ alkyl substituted by aryl;

$R^5$ and $R^6$ are each independently selected from the group consisting of hydrogen and —O$R^{19}$; or $R^5$ and $R^6$ taken together with the carbon to which they are attached form a carboxyl group (C=O);

$R^9$ is hydrogen, —N($R^{17}$)$R^{18}$, —N($R^{17}$)C(=O)$R^{18}$, or —O$R^{19}$;

$R^{12}$ is hydrogen or —O$R^{19}$;

each of $R^{17}$ and $R^{18}$ is independently selected from hydrogen, heterocyclyl optionally substituted with one to five $R^{20}$, and hydrocarbyl optionally substituted with one to five $R^{20}$;

$R^{19}$ is selected from $R^{21}$ and —C(=O)$R^{21}$;

$R^{20}$ is independently selected from the group consisting of halogen, nitro, —$R^{22}$, —O$R^{22}$, —C(=O)$R^{23}$, —C(=O)N($R^{22}$)$R^{23}$, —OC(=O)$R^{23}$, —N($R^{22}$)$R^{23}$, —N($R^{22}$)C(=O)$R^{23}$, and —N($R^{22}$)($R^{23}$)$R^{24}$;

$R^{21}$ is hydrogen, heterocyclyl optionally substituted with one to five $R^{20}$, and hydrocarbyl optionally substituted with one to five $R^{20}$;

$R^{22}$, $R^{23}$ and $R^{24}$ are each independently selected from hydrogen, hydrocarbyl and heterocyclyl; and each of $R^{25}$ and $R^{26}$ is independently selected from the group consisting of methyl, —CH$_2$OH, C(=O)H, and C(=O)OH.

In certain embodiments, the compound of Formula (II) has Formula (IIB):

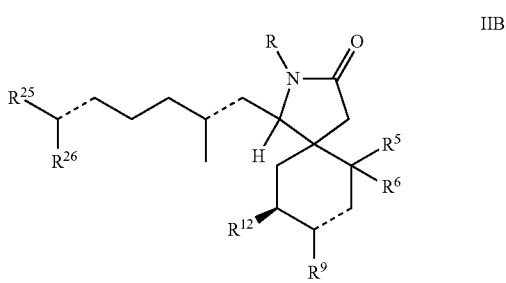

IIB or a pharmaceutically acceptable salt or prodrug thereof, wherein a dashed line represents a single or double bond;

R is hydrogen, alkyl, aryl, or $C_{1-6}$ alkyl substituted by aryl.

$R^5$ and $R^6$ are each independently selected from the group consisting of hydrogen, hydrocarbyl, hydroxyl, and —OC(=O)$R^{21}$; or $R^5$ and $R^6$ taken together with the carbon to which they are attached form a carboxyl group (C=O);

$R^9$ is hydrogen, —N($R^{17}$)$R^{18}$, —N($R^{17}$)C(=O)$R^{18}$, or —O$R^{19}$;

$R^{12}$ is hydroxyl, —O-hydrocarbyl, or —OC(=O)$R^{21}$;

each of $R^{17}$ and $R^{18}$ is independently selected from hydrogen, aryl optionally substituted with one or two $R^{20}$;

$R^{19}$ is selected from $R^{21}$ and —C(=O)$R^{21}$;

$R^{20}$ is independently selected from the group consisting of halogen, nitro, —$R^{22}$, —O$R^{22}$, —C(=O)$R^{23}$, —C(=O)N($R^{22}$)$R^{23}$, —OC(=O)$R^{23}$, —N($R^{22}$)$R^{23}$, —N($R^{22}$)C(=O)$R^{23}$, and —N($R^{22}$)($R^{23}$)$R^{24}$;

$R^{21}$ is hydrogen or hydrocarbyl, wherein the hydrocarbyl is substituted with one or two $R^{24}$; and each of $R^{25}$ and $R^{26}$ is independently selected from the group consisting of methyl, —CH$_2$OH, and C(=O)H.

In certain embodiments, the compound of Formula (II) has Formula (IIC):

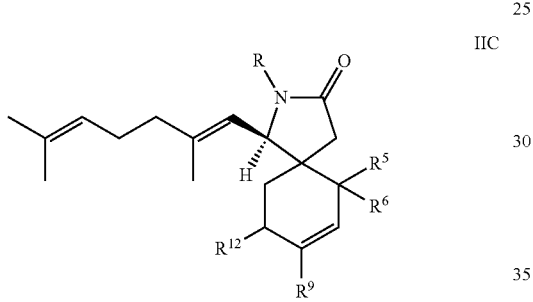

IIC or a pharmaceutically acceptable salt or prodrug thereof, wherein

R is alkyl or aryl;

$R^5$ and $R^6$ taken together with the carbon to which they are attached form a carboxyl group (C=O);

$R^9$ is hydrogen;

$R^{12}$ is hydroxyl, —OC(=O)alkyl, —OC(=O)aryl, or —OC(=O)heteroaryl, wherein —OC(=O)aryl and —OC(=O)heteroaryl are each independently optionally substituted with one to five substituents selected from the group consisting of halogen, hydroxyl, nitro, alkyl, —N($R^{22}$)$R^{23}$, and —N($R^{22}$)($R^{23}$)($R^{24}$); and $R^{22}$, $R^{23}$ and $R^{24}$ are each independently selected from hydrogen and alkyl.

In certain embodiments, the compound of Formula (II) has Formula (IIC):

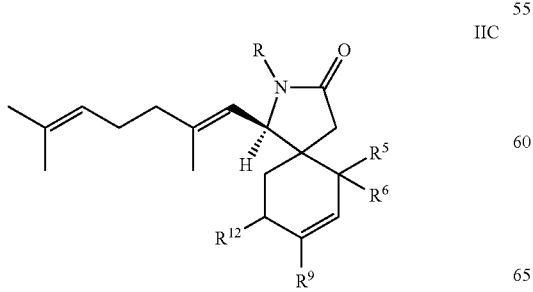

IIC or a pharmaceutically acceptable salt or prodrug thereof, wherein

R is alkyl or aryl; $R^5$ and $R^6$ taken together with the carbon to which they are attached form a carboxyl group (C=O); $R^9$ is hydrogen; and $R^{12}$ is hydroxyl or —OC(=O)alkyl.

In certain embodiments, the compound of formula (I) or said compound of formula (II) is selected from the group consisting of miliusane I, 4β-(N-phenyl)miliusate, 4α-(N-phenyl)miliusate, 4β-(N-benzoyl-N-phenyl)miliusate, 4α-(N-benzoyl-N-phenyl)miliusate, hexahydro-miliusate, 3,4-dihydro-miliusate, 2', 3', 6', 7'-tetrahydro-miliusate, 2-hydroxy-3, 4-dihydro-miliusate, 2-acetoxy-3, 4-dihydro-miliusate, 8'-oxo-miliusate, 8'-hydroxy-miliusate, 10'-hydroxy-8'-oxo-miliusate, 8', 10'-dihydroxy-miliusate, 5β-(p-trimethylammonio-benzoyl)miliusol iodide, 5β-(p-dimethyl-allyl-ammonio-benzoyl)miliusol bromide, N-(n-butyl)-miliusol lactam and N-phenyl-miliusol lactam represented by the following formula:

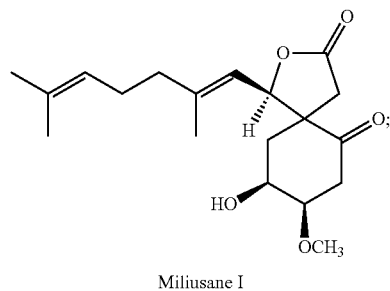

Miliusane I

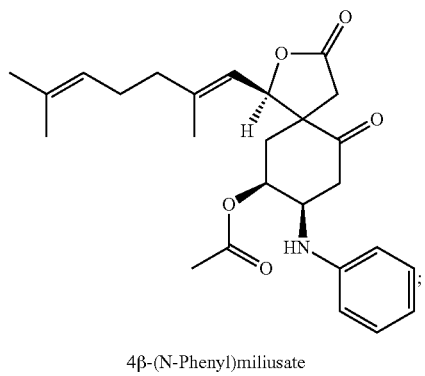

4β-(N-Phenyl)miliusate

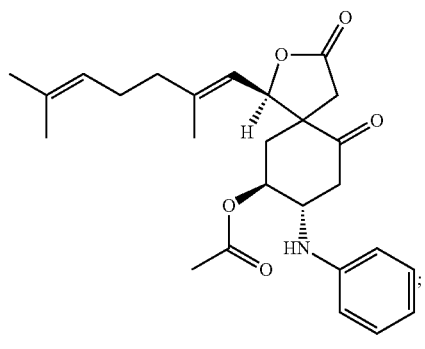

4α-(N-Phenyl)miliusate

-continued
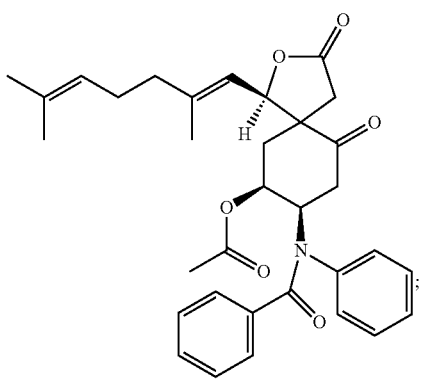
4β-(N-Benzoyl-N-phenyl)miliusate
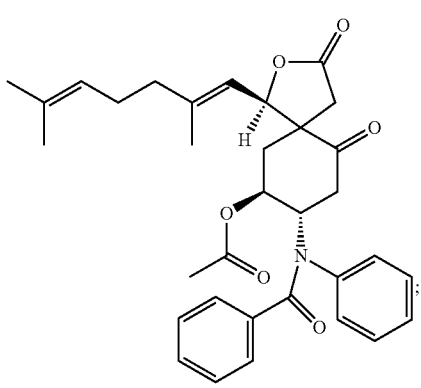
4α-(N-Benzoyl-N-phenyl)miliusate
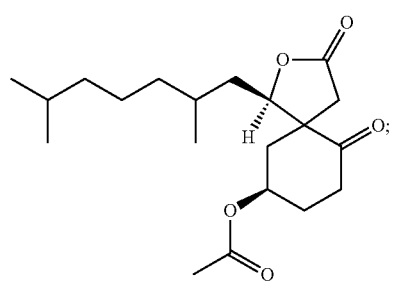
Hexahydro-miliusate
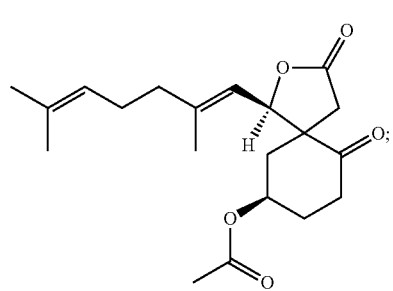
3,4-Dihydro-miliusate
-continued
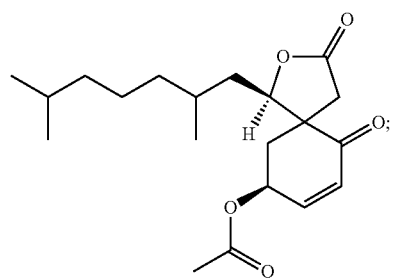
2′,3′,6′,7′-Tetrahydro-miliusate
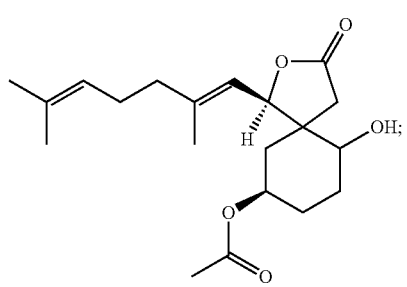
2-Hydroxy-3,4-dihydro-miliusate
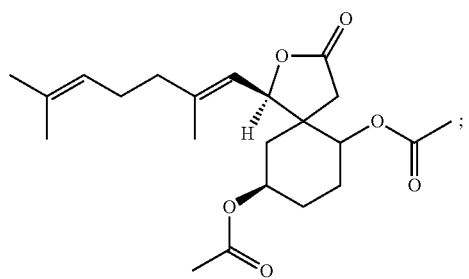
2-Acetoxy-3,4-dihydro-miliusate
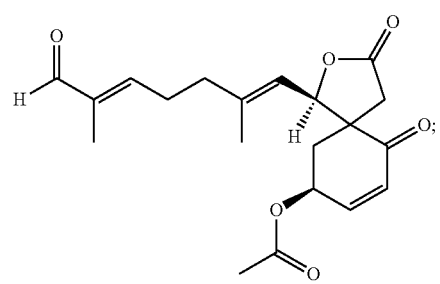
8′-Oxo-miliusate
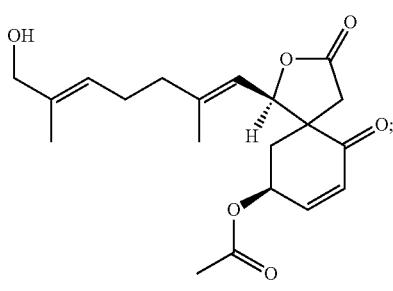
8′-Hydroxy-miliusate

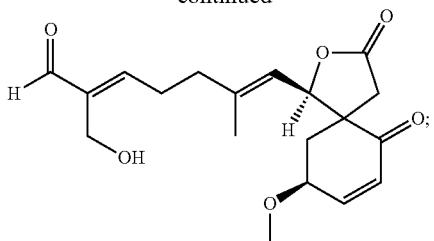

10'-Hydroxy-8'-oxo-miliusate

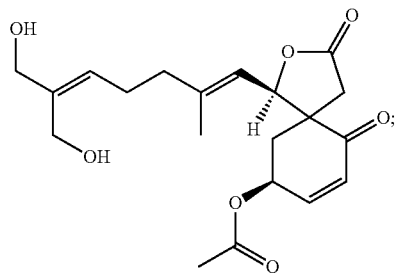

8',10'-Dihydroxy-miliusate

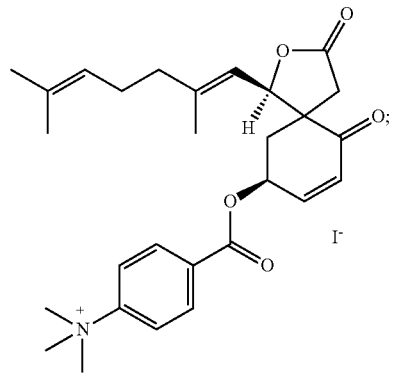

5β-(p-Trimethylammonio-benzyol)miliusol iodide

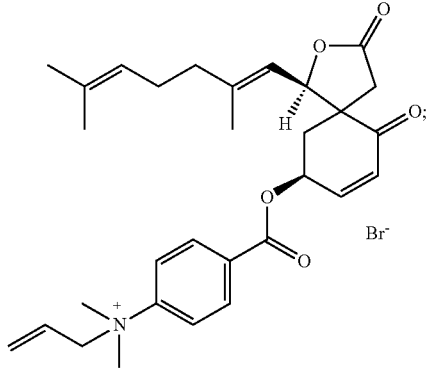

5β-(p-Dimethyl-allyl-ammonio-benzoyl)miliusol bromide

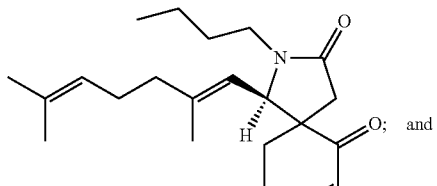

N-(n-Butyl)-miliusol lactam

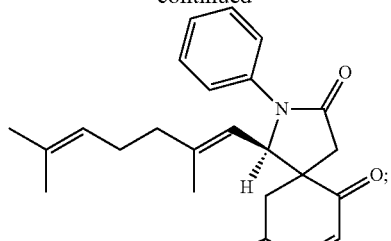

N-Phenyl-miliusol lactam or a pharmaceutically acceptable salt or prodrug thereof.

In certain embodiments, the compound of Formula (I) has Formula (IC):

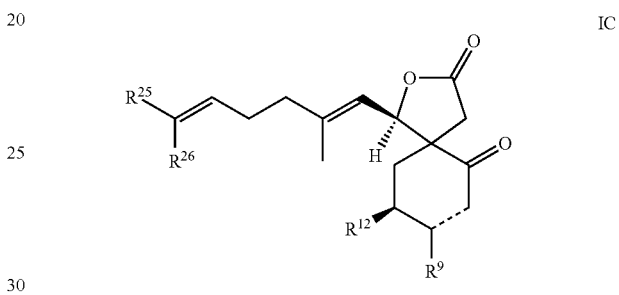

IC or a pharmaceutically acceptable salt or prodrug thereof, wherein a dashed line represents a single or double bond;
$R^9$ is hydrogen or —N($R^{17}$)$R^{18}$;
$R^{12}$ is hydroxyl, —O(C=O)alkyl;
$R^{17}$ is hydrogen;
$R^{18}$ is aryl optionally substituted with one or two $R^{20}$;
$R^{20}$ is independently selected from the group consisting of halogen, nitro, hydroxyl and alkyl; and
each of $R^{25}$ and $R^{26}$ is independently selected from the group consisting of methyl, —CH$_2$OH, and C(=O)H. The present disclosure also provides pharmaceutical composition comprising the compounds described herein and a pharmaceutical acceptable carrier thereof.

Examples of the compounds of the present disclosure include those described herein. It will of course be appreciated that, where appropriate, each compound may be in the form of the free compound, an enantiomer, an acid or base addition salt, or a prodrug.

The present disclosure provides miliusane compounds with anti-HIV and anti-influenza virus activity and synthesis thereof. The compounds of the present disclosure are natural compounds or synthesized and they are evaluated for their anti-HIV and anti-influenza virus activity. The natural miliusane compounds are exemplified by miliusane I, and the synthetic or semi-synthetic analogues of miliusanes are exemplified by 4β-(N-phenyl)miliusate, 4α-(N-phenyl)miliusate, 4β-(N-benzoyl-N-phenyl)miliusate, 4α-(N-benzoyl-N-phenyl)miliusate, hexahydro-miliusate, 3, 4-dihydro-miliusate, 2', 3', 6', 7'-tetrahydro-miliusate, 2-hydroxy-3, 4-dihydro-miliusate, 2-acetoxy-3, 4-dihydro-miliusate, 8'-oxo-miliusate, 8'-hydroxy-miliusate, 10'-hydroxy-8'-oxo-miliusate, 8', 10'-dihydroxy-miliusate, 5β-(p-trimethylammonio-benzoyl)miliusol iodide, 5β-(p-dimethyl-allyl-ammonio-benzoyl)miliusol bromide, N-(n-butyl)-miliusol lactam and N-phenyl-miliusol lactam. The chemical formulae of the compound of the present invention are as follows:
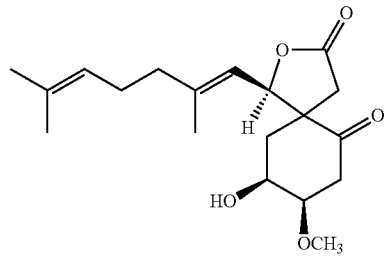
Miliusane I
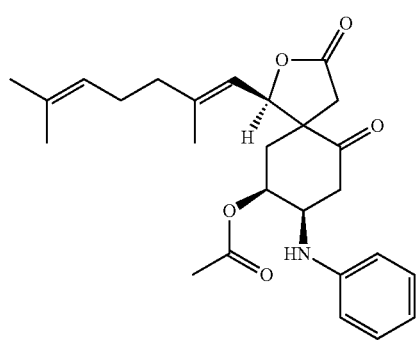
4β-(N-Phenyl)miliusate
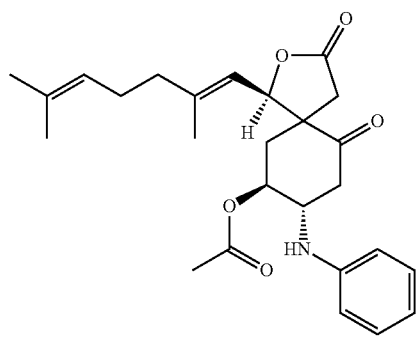
4α-(N-Phenyl)miliusate
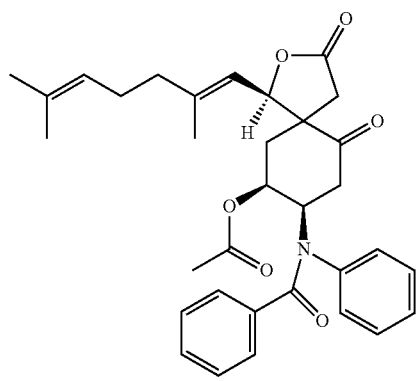
4β-(N-Benzoyl-N-phenyl)miliusate
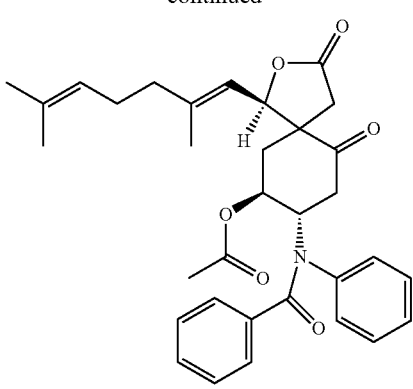
4α-(N-Benzoyl-N-phenyl)miliusate
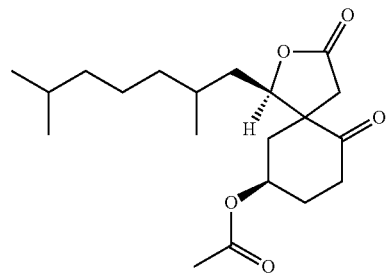
Hexahydro-miliusate
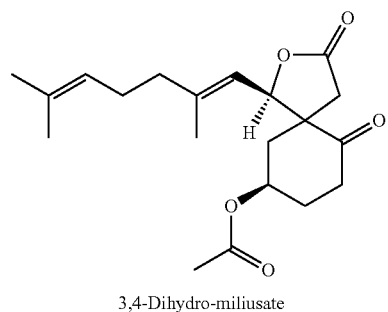
3,4-Dihydro-miliusate
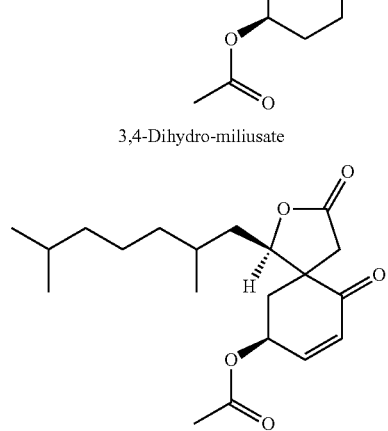
2′,3′,6′,7′-Tetrahydro-miliusate
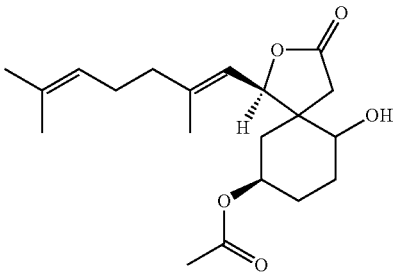
2-Hydroxy-3,4-dihydro-miliusate

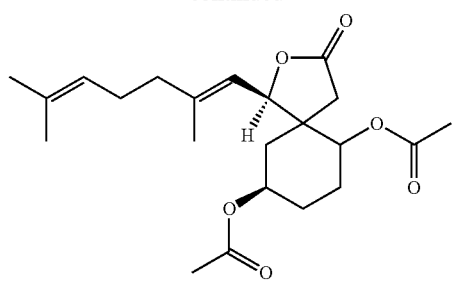

2-Acetoxy-3,4-dihydro-miliusate

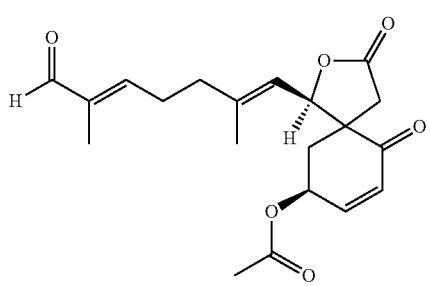

8′-Oxo-miliusate

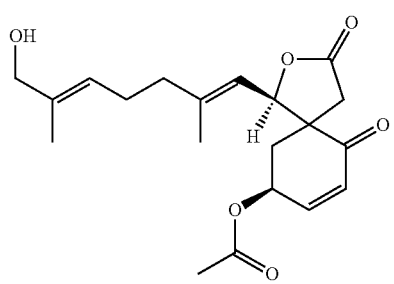

8′-Hydroxy-miliusate

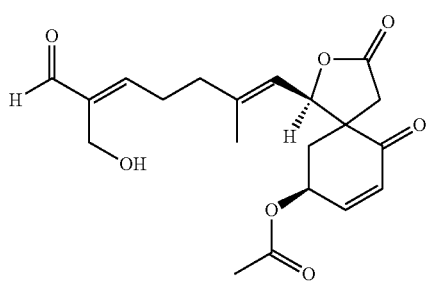

10′-Hydroxy-8′-oxo-miliusate

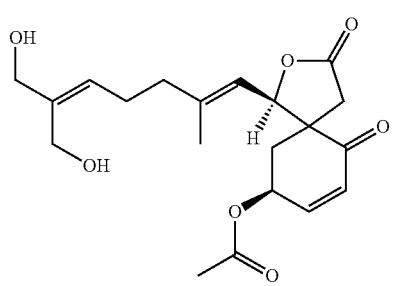

8′,10′-Dihydroxy-miliusate

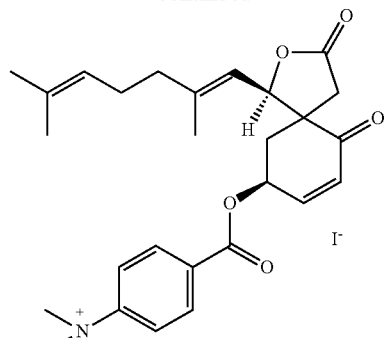

5β-(p-Trimethylammonio-benzyol)miliusol iodide

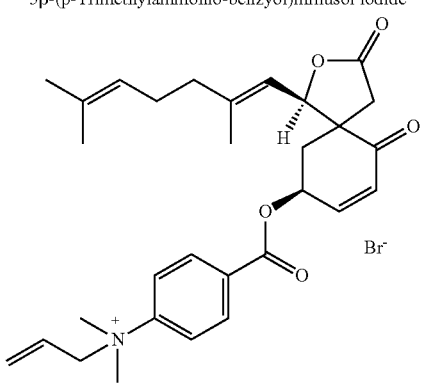

5β-(p-Dimethyl-allyl-ammonio-benzyol)miliusol bromide

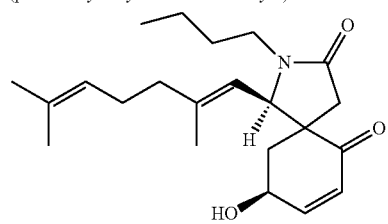

N-(n-Butyl)-miliusol lactam

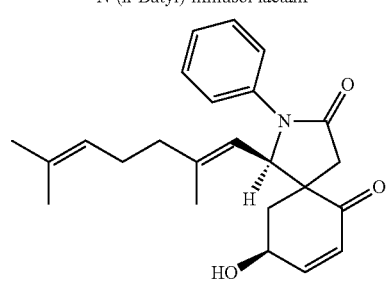

N-Phenyl-miliusol lactam

EXAMPLES

Synthesis of Novel Miliusane Derivatives.

The two natural miliusane compounds (miliusol and miliusate), isolated from *Miliusa balansae* Finet & Gagnep. (Annonaceae), were used as the starting compounds to prepare new miliusane derivatives. Miliusane I was isolated from the same plant. By using different synthetic methods, more than 17 new miliusane analogues are synthesized.

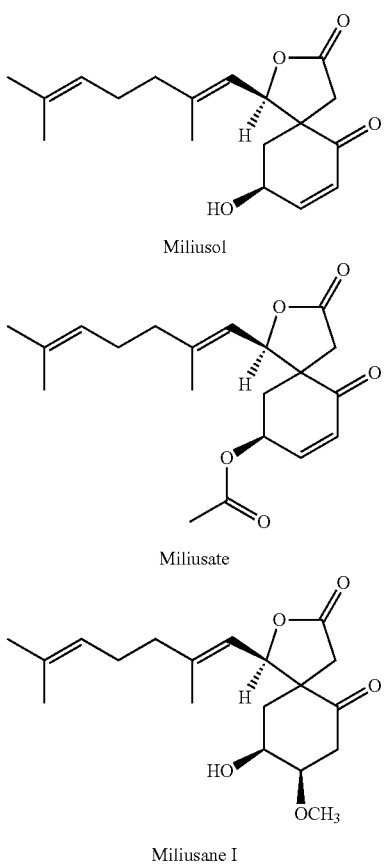

Miliusol

Miliusate

Miliusane I

These new miliusane compounds have been evaluated for their anti-HIV-1 and anti-influenza viral activities. 3,4-Dihydro-miliusate showed anti-HIV activity with an $EC_{50}$ value of 66.97 μM (SI=1). 4α-(N-Phenyl)miliusate showed anti-HIV activity with an $EC_{50}$ value of 2.70 μM (SI> 24). 10'-Hydroxy-8'-oxo-miliusate showed anti-HIV activity with an $EC_{50}$ value of 4.97 μM (SI=12.1). 8',10'-Dihydroxy-miliusate showed anti-HIV activity with an $EC_{50}$ value of 14.4 μM (SI=9.5). Miliusane I demonstrated anti-influenza A (anti-H5N1) activity with an $EC_{50}$ value of 0.71 μM (SI=9.5).

Since 4α-(N-phenyl)miliusate shows better anti-HIV activity comparing with its peers, the compound is further evaluated for its toxicity in mice. In the animal experiment, all mice remained healthy and no weight loss was observed for all mice when the mice were treated with two doses at 20 and 40 mg/kg for 21 days (10 mice/group, once other day treatment), suggesting low toxicity of 4α-(N-phenyl)miliusate, which deems the compound for potential anti-HIV lead compound for further development.

General Method for Preparation of 4-Amino Substituted Miliusane Derivatives.

Bismuth nitrate [$Bi(NO_3)_3$] (70 mg, 0.5 eq) is added to a mixture of an amine such as aniline (1.35 g, 50 eq) and a miliusane such as miliusate (100 mg, 0.29 mmol) in dichloromethane ($CH_2Cl_2$, 2 mL). The reaction mixture is stirred at room temperature for 48 hours. $CH_2Cl_2$ (30 mL) is added to the reaction mixture, and the $CH_2Cl_2$ solution is filtered through filter paper to remove $Bi(NO_3)_3$. The filtrate is washed with saturated $NaHCO_3$ (2×10 mL) and brine (1×10 mL), and dried over $Na_2SO_4$. The $CH_2Cl_2$ solution is concentrated, and is further purified using chromatography on a silica gel column eluting with a mixture of solvent such as petroleum ether:EtOAc (ethyl acetate) 4:1 to afford 4-amino substituted miliusane derivative(s). Unreacted, partially reacted or unwanted compounds as disclosed herein can be removed from the reaction product.

SCHEME 1

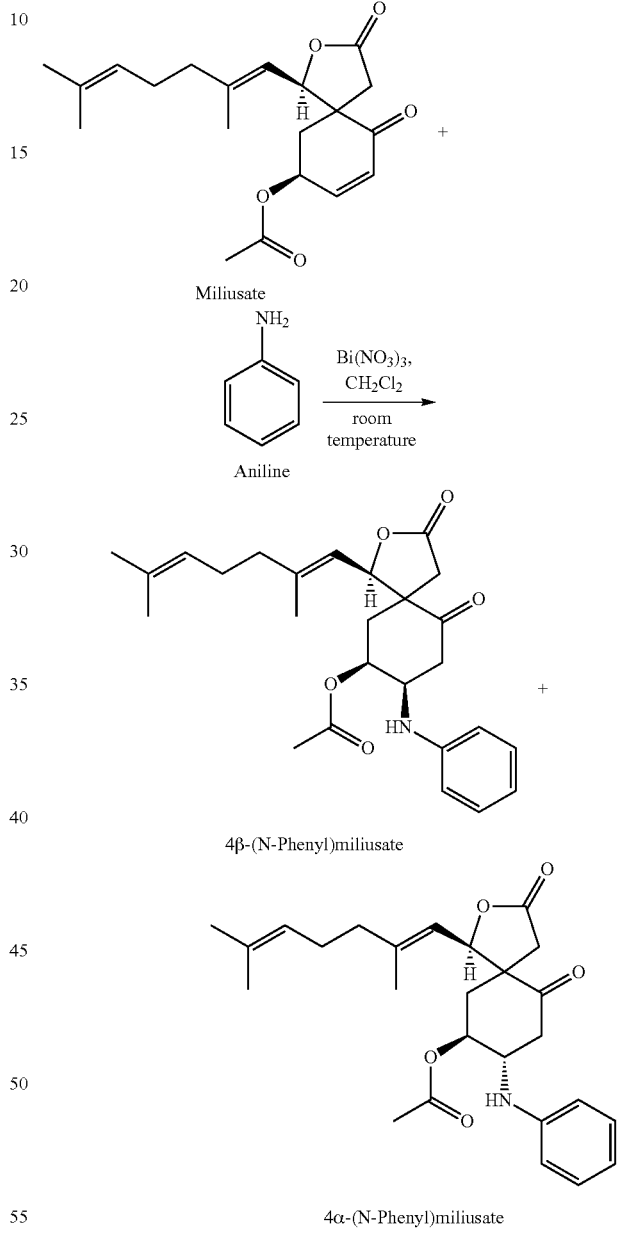

The new molecules 4β-(N-phenyl)miliusate and 4α-(N-phenyl)miliusate are thus synthesized (see Scheme 1).

General Method for Preparation of Amino Substituted Miliusane Amide Derivatives.

To a solution of an amino substituted miliusane derivative such as 4α-(N-benzyl)miliusate and 4β-(N-benzyl)miliusate (30 mg, 0.068 mmol) in anhydrous pyridine (5 mL) is added benzoyl chloride (BzCl) (19 mg, 2 eq) and a catalytic amount of 4-dimethylaminopyridine (DMAP). The reaction is stirred overnight at room temperature, and quenched with H₂O (30 mL). The reaction mixture is then extracted with ethyl acetate (3×20 mL). The combined ethyl acetate solution is washed with H₂O (20 mL) and brine (20 mL), and dried over Na₂SO₄. The solution is then concentrated in vacuo, and chromatographed on a silica gel column, eluted with a solvent system such as petroleum ether:EtOAc 2:1 to afford amino substituted miliusane amide derivative. Unreacted, partially reacted or unwanted compounds as disclosed herein can be removed from the reaction product.

SCHEME 2

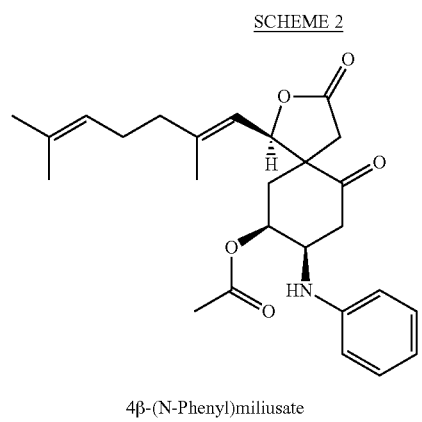

4β-(N-Phenyl)miliusate

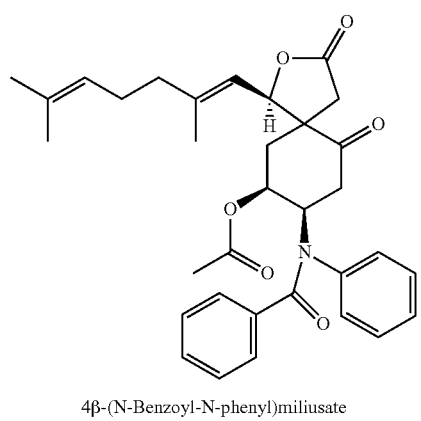

4β-(N-Benzoyl-N-phenyl)miliusate

SCHEME 3

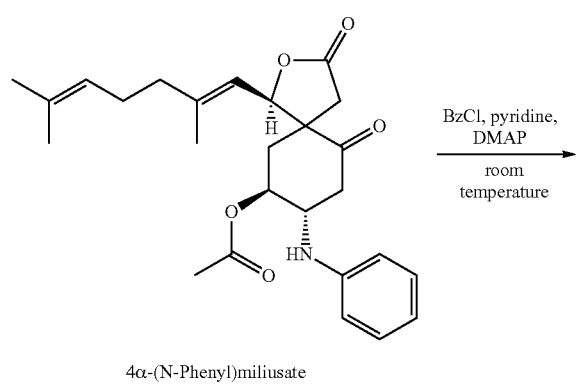

4α-(N-Phenyl)miliusate

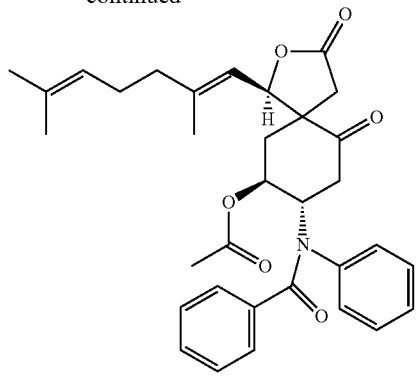

4α-(N-Benzoyl-N-phenyl)miliusate

The new molecules 4β-(N-benzoyl-N-phenyl)miliusate, and 4α-(N-benzoyl-N-phenyl)miliusate are thus synthesized (see Schemes 2 and 3).

General Method for Preparation of Hexahydro-Miliusane Derivatives.

A solution of a miliusane such as miliusate (20 mg, 0.058 mmol) in EtOAc (5 mL) is treated with 10% of the catalyst palladium on activate charcoal (Pd/C) (5 mg). The resulting black suspension is stirred under hydrogen (H₂) (1 atmosphere) at room temperature for 3 hours. The catalyst is removed by filtration through Celite and washed with EtOAc (20 mL). The filtrate is evaporated in vacuo and the residue is subjected to chromatography separation on silica gel, eluted with a solvent system such as petroleum ether: EtOAc 4:1 to afford hexahydro-miliusane derivative. Unreacted, partially reacted or unwanted compounds as disclosed herein can be removed from the reaction product.

SCHEME 4

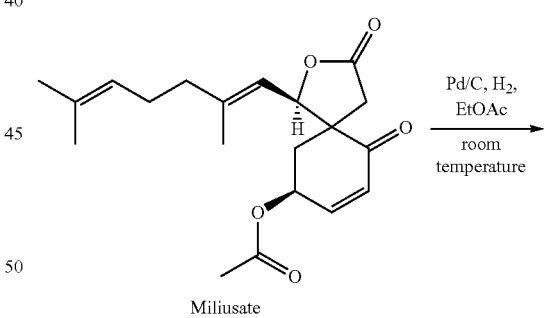

Miliusate

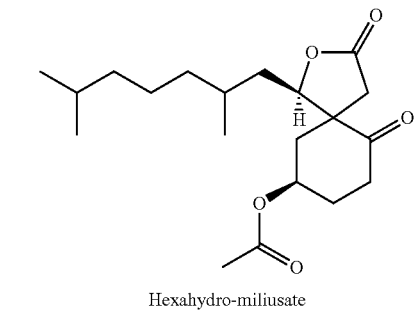

Hexahydro-miliusate

The new molecule hexahydro-miliusate is thus synthesized (see Scheme 4).

General Method for Preparation of 3, 4-Dihydro-Miliusane Derivatives.

A solution of a miliusane such as miliusate (10 mg, 0.029 mmol) in EtOAc (3 mL) is treated with 10% Pd/C (5 mg). The resulting black suspension is stirred under $H_2$ (1 atmosphere) at −78° C. for 48 hours. The catalyst is removed by filtration through Celite and washed with EtOAc (20 mL). The filtrate is evaporated in vacuo and the residue is subjected to chromatography separation on silica gel, eluted with a solvent system such as petroleum ether:EtOAc 4:1 to afford the 3,4-dihydro-miliusane derivative. Unreacted, partially reacted or unwanted compounds as disclosed herein can be removed from the reaction product.

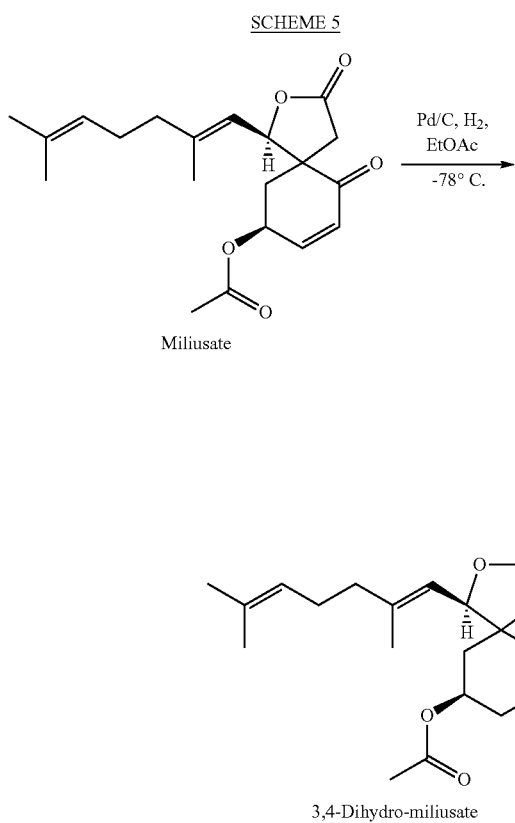

SCHEME 5

Miliusate 3,4-Dihydro-miliusate

The new molecule 3, 4-dihydro-miliusate is thus synthesized (see Scheme 5).

General Method for Preparation of 2', 3', 6', 7'-Tetrahydro-Miliusane Derivatives.

To a solution of a miliusane such as hexahydro-miliusate (20 mg, 0.056 mmol) in toluene: DMSO (2:1, 0.1 M) is added 2-iodoxybenzoic acid (IBX) (20.7 mg, 1.3 eq). The resulting solution is heated to 100° C. for stirring 3 hours. The reaction mixture is then diluted with $CH_2Cl_2$ (30 mL), and washed sequentially with 5% $NaHCO_3$ (1×10 mL), $H_2O$ (1×10 mL), and brine (1×10 mL), followed by removal of solvent in vacuo, leading to crude products, which can be purified using silica gel column chromatography to afford the 2',3',6',7'-tetrahydro-miliusane derivative. Unreacted, partially reacted or unwanted compounds as disclosed herein can be removed from the reaction product.

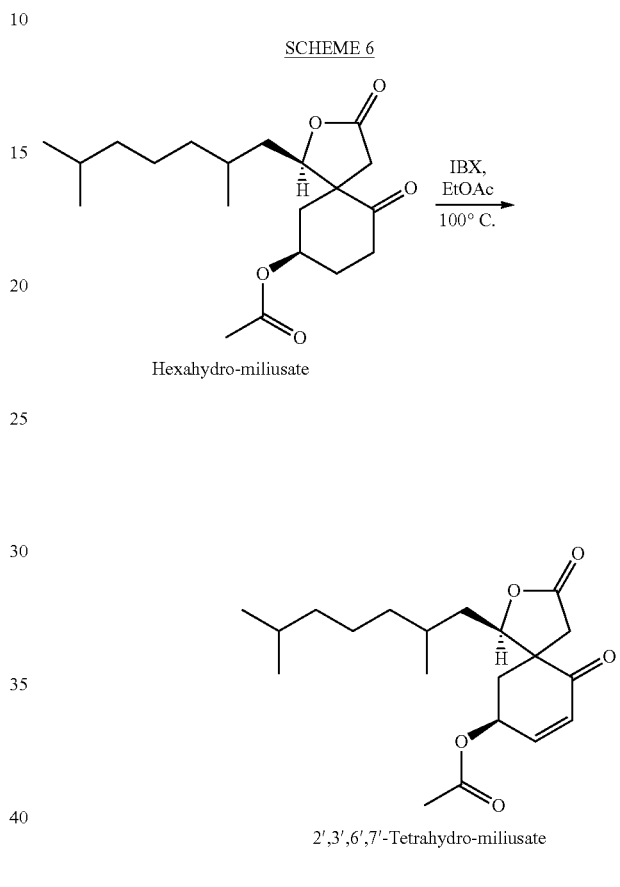

SCHEME 6

Hexahydro-miliusate

2',3',6',7'-Tetrahydro-miliusate

The new molecules 2',3',6',7'-tetrahydro-miliusate is thus synthesized (see Scheme 6).

General Method for Preparation of 2-Hydroxy-Miliusane Derivatives.

To a stirred solution of a miliusane such as miliusate (20 mg, 0.058 mmol) in MeOH (5 mL) is added sodium borohydride ($NaBH_4$) (2.2 mg, 1 eq) at 0° C. The reaction mixture is stirred at 0° C. for 1 hour, quenched with saturated ammonium chloride ($NH_4Cl$) (10 mL), and then extracted with EtOAc (3×20 mL). The combined EtOAc solution is washed sequentially with $H_2O$ (10 mL) and brine (10 mL), dried over $Na_2SO_4$, and concentrated in vacuo. The reaction mixture is subjected to chromatography separation on a silica gel column, eluted with a solvent system such as petroleum ether:EtOAc 2:1 to afford the 2-hydroxy-miliusane derivative. Unreacted, partially reacted or unwanted compounds as disclosed herein can be removed from the reaction product.

SCHEME 7

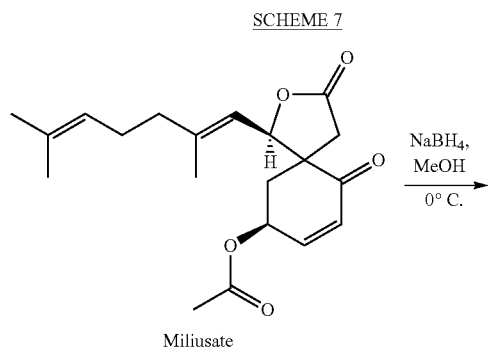

Miliusate

SCHEME 8

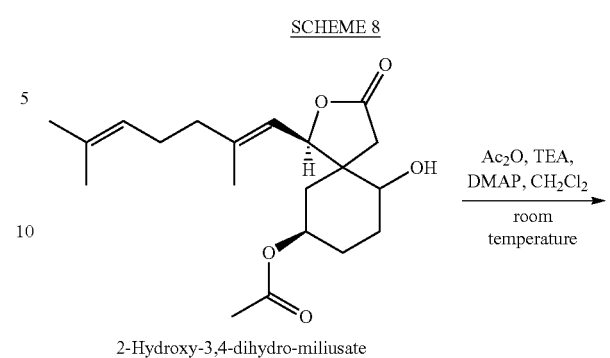

2-Hydroxy-3,4-dihydro-miliusate

2–Hydroxy-3,4-dihydro-miliusate

2–Acetoxy-3,4-dihydro-miliusate

The new molecule 2-hydroxy-3, 4-dihydro-miliusate is thus synthesized (see Scheme 7).

General Method for Preparation of Ester Derivatives of 2-Hydroxy-Miliusanes.

A solution of a 2-hydroxy-miliusane such as 2-hydroxy-3, 4-dihydro-miliusate (8 mg, 0.023 mmol) in CH$_2$Cl$_2$ (5 mL) is treated with triethylamine (TEA) (16.0 µL, 5 eq), anhydrous acetic acid (Ac$_2$O) (6.5 µL, 3 eq) and a catalytic amount of DMAP. The reaction mixture is stirred at room temperature for 3 hours, quenched with saturated NaHCO$_3$ (20 mL), and then extracted with EtOAc (3×10 mL). The combined EtOAc solution is washed with H$_2$O (10 mL) and brine (10 mL), dried over Na$_2$SO$_4$, and concentrated in vacuo. The mixture is chromatographed on a silica gel column, eluting with petroleum ether:EtOAc 4:1 to afford the ester derivative of 2-hydroxy-miliusane. Unreacted, partially reacted or unwanted compounds as disclosed herein can be removed from the reaction product.

The new molecule 2-acetoxy-3, 4-dihydro-miliusate is thus synthesized (see Scheme 8).

General Method for Preparation of Aldehyde and Hydroxy Derivatives on the Side Chain of Miliusanes.

To a 25-mL flask is introduced 16 mg (0.5 eq) of selenium dioxide (SeO$_2$), 10 mL of CH$_2$Cl$_2$ and 80 µL (2 eq) of 70% tert-butyl hydroperoxide (TBHP). After the mixture is stirred for 0.5 hours at 25° C. (water bath), a miliusane such as miliusate (100 mg, 0.29 mmol) is added in several minutes. The mixture is stirred at 25° C. for 48 hours. The solvent is then removed in vacuo, and the residue is subjected to silica gel column chromatography separation to give side chain aldehyde and hydroxy derivatives of miliusanes. Unreacted, partially reacted or unwanted compounds as disclosed herein can be removed from the reaction product.

SCHEME 9

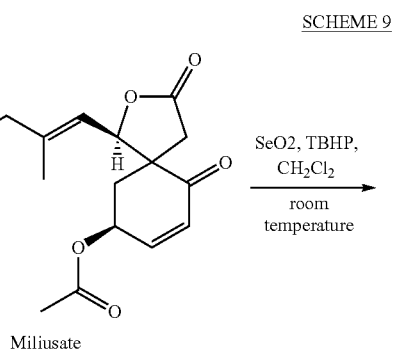

Miliusate

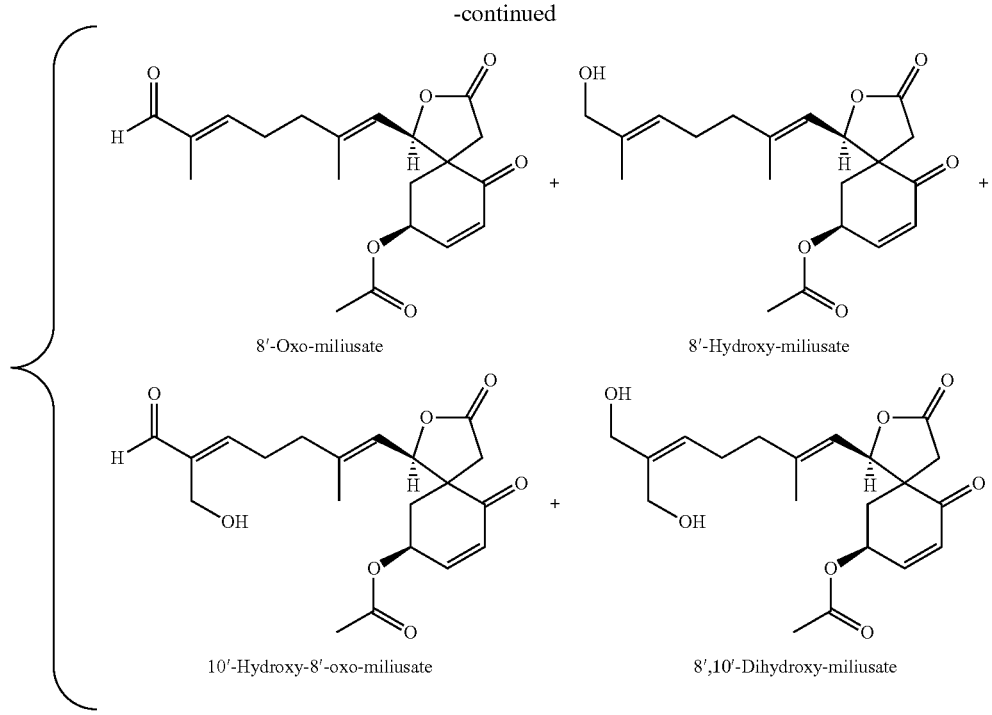

8'-Oxo-miliusate

8'-Hydroxy-miliusate

10'-Hydroxy-8'-oxo-miliusate

8',10'-Dihydroxy-miliusate

The new molecules 8'-oxo-miliusate, 8'-hydroxy-miliusate, 10'-hydroxy-8'-oxo-miliusate, and 8', 10'-dihydroxy-miliusate are thus synthesized (see Scheme 9).

General Method for Preparation of Miliusol Ester Derivatives.

The solution of 5.0 mg of miliusane such as miliusol (0.016 mmol) in 1.0 mL of dry pyridine is pipetted into a solution of selected acyl chloride reagent such as p-dimethyl-benzyol chloride (0.2 mmol) in 1.0 mL of dry pyridine at 0° C. The reaction is allowed to proceed at 0° C. for 2 hours, and additional 20 hours at room temperature. The reaction product is evaporated in vacuo to dryness to afford a mixture, which is subjected to a silica gel column chromatography to afford the acyl-miliusane ester. Unreacted, partially reacted or unwanted compounds as disclosed herein can be removed from the reaction product. The molecule 5β-(p-dimethylamino-benzoyl)miliusol is thus synthesized (see Scheme 10).

SCHEME 10

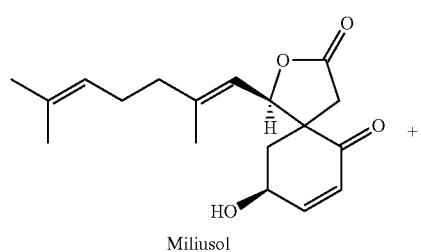

Miliusol

+

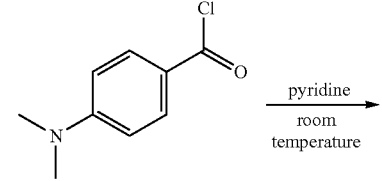

p-Dimethyl-benzoyl chloride $\xrightarrow{\text{pyridine}}_{\text{room temperature}}$

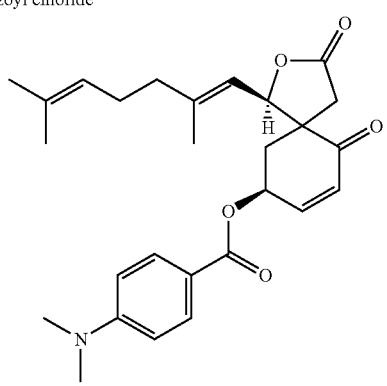

5β-(p-Dimethylamino-benzoyl)miliusol

General Method for Preparation of Miliusane Ammonium Salts.

A chloroform (CHCl₃) solution of an amino group containing miliusane derivative such as 5β-(p-dimethylamino-benzoyl)miliusol (10 mg, 0.022 mmol) and an alkyl halide such as methyl iodide or allyl bromide (10 mL) is refluxed under N₂ atmosphere for 72 hours. Products can be detected by TLC, HPLC and LC-MS. The reaction product is evaporated in vacuo to dryness to afford a mixture, which is subjected to a Si gel column separation to afford miliusane ammonium salt product. Unreacted, partially reacted or unwanted compounds as disclosed herein can be removed from the reaction product.

SCHEME 11

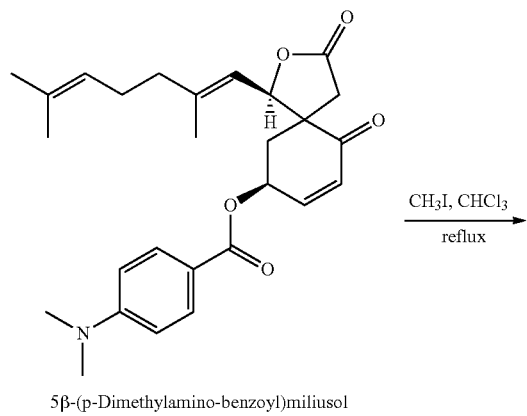

5β-(p-Dimethylamino-benzoyl)miliusol

SCHEME 12

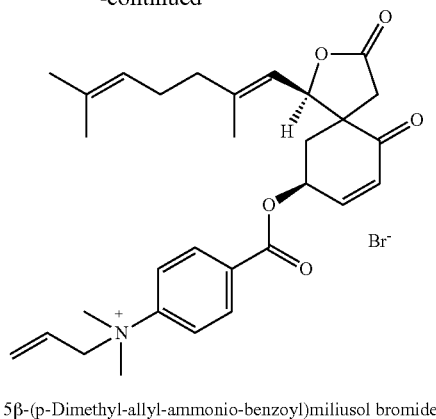

5β-(p-Dimethyl-allyl-ammonio-benzoyl)miliusol bromide

The new molecules 5β-(p-trimethylammonio-benzoyl) miliusol iodide and 5β-(p-dimethyl-allyl-ammonio-benzoyl) miliusol bromide are thus synthesized (see Schemes 11 and 12).

General Method for Preparation of Miliusane Lactam.

A mixture of a miliusane such as miliusol (6.1 mg, 0.02 mmol), a primary amine such as n-butylamine (5.9 µL, 0.06 mmol) or aniline (5.5 µL, 0.06 mmol) and 1-butyl-3-methylimidazolium tetrafluoroborate ([bmim]BF$_4$, 3.7 µL, 0.02 mmol) is vortexed in a sealed vessel for 30 seconds prior to microwave irradiation at 220° C. for 35 minutes. The cooled reaction mixture is then diluted with 5 mL of EtOAc and washed with saturated aqueous NH$_4$Cl. The collected EtOAc solution is concentrated in vacuo, and purified over a silica gel column to afford miliusane lactam product. Unreacted, partially reacted or unwanted compounds as disclosed herein can be removed from the reaction product.

SCHEME 13

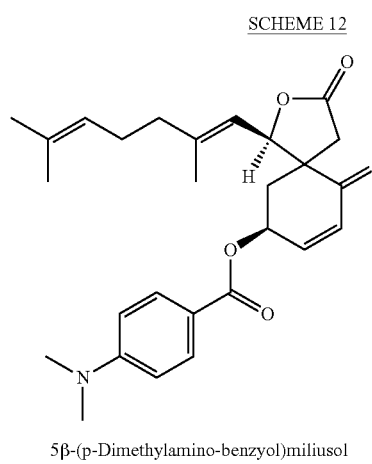

SCHEME 14

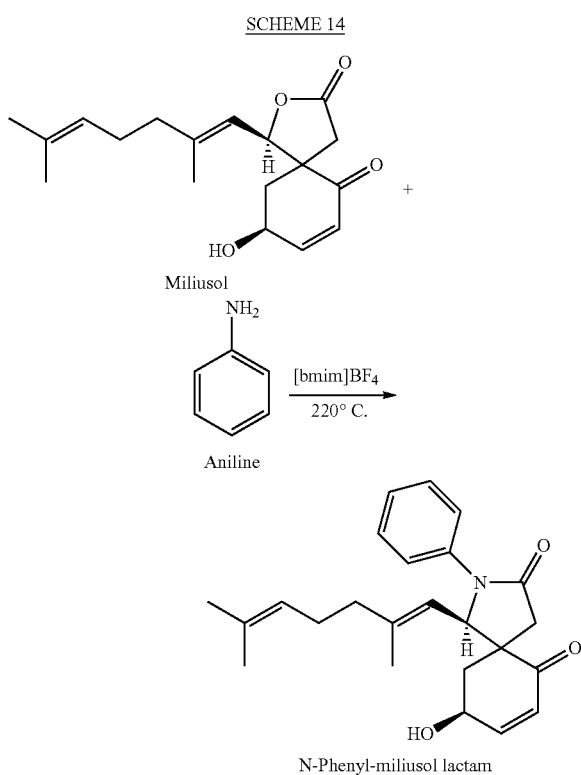

The new molecules N-(n-butyl)-miliusol lactam and N-phenyl-miliusol lactam are thus synthesized (see Schemes 13 and 14).

4β-(N-Phenyl)miliusate is obtained as a white powder with a molecular formula of $C_{26}H_{33}NO_5$ determined by positive HRESIMS and NMR studies. $^1$H NMR (400 MHz, CDCl$_3$, J in Hz) δ (in ppm with reference to the signal of CDCl$_3$ at δ 7.24 ppm) phenyl protons [7.18 (2H, brt, J=7.5), 6.79 (1H, brt, J=6.7), 6.60 (2H, brs)], 5.58 (1H, d, J=10.6, H-1'), 5.48 (1H, brs, H-5), 4.96 (1H, brd, J=10.8, H-2'), 4.94 (1H, m, H-6'), 3.81 (1H, brdt, J=13.1, 3.5, H-4), 3.57 (1H, d, J=18.1, H-7β), 2.76 (1H, brdd, J=13.1, 3.1, H-3α), 2.66 (1H, dd, J=15.7, 2.7, H-6β), 2.48 (1H, brt, J=13.1, H-3β), 2.24 [3H, s, OC(=O)CH$_3$], 2.00 (1H, d, J=18.0, H-7α), 2.02 (4H, m, H$_2$-4' and H$_2$-5'), 1.84 (3H, d, J=1.3 Hz, CH$_3$-9'), 1.75 (1H, dd, J=15.6, 3.3, H-6α), 1.63 (3H, s, CH$_3$-8'), 1.55 (3H, s, CH$_3$-10'). HRTOF positive ESIMS m/z calcd for $C_{26}H_{33}NO_5$: 440.2432 [M+1]$^+$, found: 440.2425 [M+1]$^+$.

4α-(N-Phenyl)miliusate is obtained as a white powder with a molecular formula of $C_{26}H_{33}NO_5$ determined by positive HRESIMS and NMR studies. $^1$H NMR (400 MHz, CDCl$_3$, J in Hz) δ (in ppm with reference to the signal of CDCl$_3$ at δ 7.24 ppm) phenyl protons [7.21 (2H, brt, J=7.8), 6.79 (3H, m)], 5.81 (1H, d, J=10.6, H-1'), 5.38 (1H, brq, J=2.9, H-5), 5.01 (1H, brd, J=10.7, H-2'), 4.95 (1H, m, H-6'), 4.04 (1H, m, H-4), 3.57 (1H, d, J=18.1, H-7β), 2.81 (1H, dd, J=14.0, 4.6, H-3β), 2.40 (1H, brd, J=15.3, H-6β), 2.39 (1H, brd, J=13.2, H-3α), 2.23 [3H, s, OC(=O)CH$_3$], 2.16 (1H, dd, J=15.4, 3.8, H-6α), 2.08 (1H, d, J=18.3, H-7α), 2.04 (4H, m, H$_2$-4' and H$_2$-5'), 1.86 (3H, d, J=1.3 Hz, CH$_3$-9'), 1.66 (3H, s, CH$_3$-8'), 1.57 (3H, s, CH$_3$-10'). HRTOF positive ESIMS m/z calcd for $C_{26}H_{33}NO_5$: 440.2432 [M+1]$^+$, found: 440.2436 [M+1]$^+$.

4β-(N-Benzoyl-N-phenyl)miliusate is obtained as a white powder with a molecular formula of $C_{33}H_{37}NO_6$ determined by positive HRESIMS and NMR studies. $^1$H NMR (400 MHz, CDCl$_3$, J in Hz) δ (in ppm with reference to the signal of CDCl$_3$ at δ 7.24 ppm) aromatic protons [7.06-7.25 (8H, m), 6.93-7.00 (2H, m)], 5.66 (1H, brtd, J=8.3, 4.9, H-5), 5.22 (1H, brd, J=10.0, H-2'), 5.10 (1H, d, J=10.0, H-1'), 4.99 (1H, m, H-6'), 4.60 (1H, brtd, J=8.0, 5.9, H-4), 3.33 (1H, d, J=17.4, H-7β), 2.87 (1H, dd, J=16.6, 5.8, H-3α), 2.74 (1H, dd, J=16.6, 8.4, H-3β), 2.42 (1H, d, J=17.5, H-7α), 2.19 (1H, dd, J=13.9, 4.9, H-6β), 2.11 (1H, dd, J=14.0, 8.9, H-6a), 2.09 [3H, s, OC(=O)CH$_3$], 2.05 (4H, m, H$_2$-4' and H$_2$-5'), 1.76 (3H, d, J=1.3 Hz, CH$_3$-9'), 1.64 (3H, s, CH$_3$-8'), 1.57 (3H, s, CH$_3$-10'). HRTOF positive ESIMS m/z calcd for $C_{33}H_{37}NO_6$: 544.2694 [M+1]$^+$, found: 544.2690 [M+1]$^+$.

4α-(N-Benzoyl-N-phenyl)miliusate is obtained as a white powder with a molecular formula of $C_{33}H_{37}NO_6$ determined by positive HRESIMS and NMR studies. $^1$H NMR (400 MHz, CDCl$_3$, J in Hz) δ (in ppm with reference to the signal of CDCl$_3$ at δ 7.24 ppm) aromatic protons [7.06-7.22 (8H, m), 6.97-7.01 (2H, m)], 5.94 (1H, brq, J=2.2, H-5), 5.58 (1H, d, J=10.6, H-1'), 5.00 (1H, brddd, J=14.8, 3.9, 2.7, H-4), 4.92 (1H, brdd, J=10.6, 1.0, H-2'), 4.88 (1H, m, H-6'), 3.57 (1H, d, J=18.0, H-7β), 2.79 (1H, dd, J=14.9, 13.1, H-3β), 2.55 (1H, brdd, J=15.6, 2.9, H-6β), 2.48 (1H, brdd, J=13.0, 3.9, 1.2, H-3α), 2.05 [3H, s, OC(=O)CH$_3$], 1.96 (4H, m, H$_2$-4' and H$_2$-5'), 1.88 (1H, dd, J=15.6, 3.4, H-6α), 1.98 (1H, d, J=18.2, H-7α), 1.67 (3H, d, J=1.3 Hz, CH$_3$-9'), 1.62 (3H, s, CH$_3$-8'), 1.52 (3H, s, CH$_3$-10'). HRTOF positive ESIMS m/z calcd for $C_{33}H_{37}NO_6$: 544.2694 [M+1]$^+$, found: 544.2699 [M+1]$^+$.

Hexadehydro-miliusate is obtained as a white powder with a molecular formula of $C_{20}H_{32}O_5$ determined by positive HRESIMS and NMR studies. $^1$H NMR (400 MHz, CDCl$_3$, J in Hz) δ (in ppm with reference to the signal of CDCl$_3$ at δ 7.24 ppm) 5.29 (1H, brquintet, J=3.2, H-5), 5.01 (1H, brdd, J=11.6, 2.1, H-1'), 3.43 (1H, d, J=17.9, H-7β), 2.41-2.64 (3H, m), 2.28 (1H, m), 2.13 [3H, s, OC(=O)CH$_3$], 2.04 (1H, m), 2.01 (1H, d, J=17.9, H-7α), 1.83 (1H, dd, J=15.2, 3.7, H-6α), 1.68 (1H, m), 1.27-1.56 (4H, m), 0.94-1.28 (5H, m), 0.88 (3H, d, J=6.7 Hz), 0.84 (3H, d, J=6.6 Hz), 0.83 (3H, d, J=6.6 Hz). HRTOF positive ESIMS m/z calcd for $C_{20}H_{32}O_5$: 353.2323 [M+1]$^+$, found: 353.2318 [M+1]$^+$.

3,4-Didehydro-miliusate is obtained as a white powder with a molecular formula of $C_{20}H_{28}O_5$ determined by positive HRESIMS and NMR studies. $^1$H NMR (400 MHz, CDCl$_3$, J in Hz) δ (in ppm with reference to the signal of CDCl$_3$ at δ 7.24 ppm) 5.74 (1H, d, J=10.6, H-1'), 5.27 (1H, brquintet, J=3.0, H-5), 4.98 (1H, brdd, J=10.6, 1.0, H-2'), 4.94 (1H, m, H-6'), 3.54 (1H, d, J=18.0, H-7β), 2.55 (1H, brdt, J=15.3, 3.0), 2.42 (1H, brtd, J=14.6, 6.1), 2.30 (1H, brdd, J=13.4, 5.8, 2.9), 2.25 (1H, m), 2.15 [3H, s, OC(=O)CH$_3$], 2.01 (4H, m, H$_2$-4' and H$_2$-5'), 2.00 (1H, d, J=18.0, H-7α), 1.96 (2H, m), 1.82 (3H, d, J=1.3 Hz, CH$_3$-9'), 1.64 (3H, s, CH$_3$-8'), 1.55 (3H, s, CH$_3$-10'). HRTOF positive ESIMS m/z calcd for $C_{20}H_{28}O_5$: 349.2010 [M+1]$^+$, found: 349.2005 [M+1]$^+$.

2',3',6',7'-Tetradehydro-miliusate is obtained as a white powder with a molecular formula of $C_{26}H_{33}NO_5$ determined by positive HRESIMS and NMR studies. $^1$H NMR (400 MHz, CDCl$_3$, J in Hz) δ (in ppm with reference to the signal of CDCl$_3$ at δ 7.24 ppm) 6.87 (1H, brddd, J=10.2, 4.2, 1.8, H-4), 6.16 (1H, brdd, J=10.2, 1.1, H-3), 5.52 (1H, brqd, J=4.0, 1.1, H-5), 4.72 (1H, brdd, J=10.8, 2.6, H-1'), 3.20 (1H, d, J=17.5, H-7β), 2.37 (1H, brdtd, J=14.9, 3.9, 0.9), 2.26 (1H, brdt, J=14.7, 4.2), 2.25 (1H, d, J=17.6, H-7α), 2.11 [3H, s, OC(=O)CH$_3$], 1.83 (1H, dd, J=15.2, 3.7, H-6α), 1.40-1.60 (2H, m), 0.93-1.40 (7H, m), 0.88 (3H, d, J=6.7

Hz), 0.83 (6H, d, J=6.5 Hz). HRTOF positive ESIMS m/z calcd for $C_{20}H_{30}O_5$: 351.2166 [M+1]$^+$, found: 351.2156 [M+1]$^+$.

2-Hydroxy-3,4-didehydro-miliusate is obtained as a white powder with a molecular formula of $C_{20}H_{30}O_5$ determined by positive HRESIMS and NMR studies. $^1$H NMR (400 MHz, CDCl$_3$, J in Hz) δ (in ppm with reference to the signal of CDCl$_3$ at δ 7.24 ppm) 5.24 (1H, brd, J=10.4, H-2'), 4.99 (1H, m, H-6'), 4.82 (1H, d, J=10.5, H-1'), 4.76 (1H, brseptet, J=4.7, H-5), 3.70 (1H, brs, H-2), 2.47 (1H, d, J=17.3, H-7β), 2.33 (1H, brdd, J=17.3, 1.4, H-7α), 2.07-2.24 (5H, m), 2.02 [3H, s, OC(=O)CH$_3$], 1.98 (1H, brt, J=11.4), 1.77-1.92 (4H, m), 1.74 (3H, d, J=1.3 Hz, CH$_3$-9'), 1.67 (3H, s, CH$_3$-8'), 1.60 (3H, s, CH$_3$-10'). HRTOF positive ESIMS m/z calcd for $C_{20}H_{30}O_5$: 351.2166 [M+1]$^+$, found: 351.2160 [M+1]$^+$.

2-Acetoxy-3,4-didehydro-miliusate is obtained as a white powder with a molecular formula of $C_{22}H_{32}O_6$ determined by positive HRESIMS. HRTOF positive ESIMS m/z calcd for $C_{22}H_{32}O_6$: 393.2272 [M+1]$^+$, found: 393.2266 [M+1]$^+$.

8'-Oxo-miliusate is obtained as a white powder with a molecular formula of $C_{20}H_{24}O_6$ determined by positive HRESIMS and NMR studies. $^1$H NMR (400 MHz, CDCl$_3$, J in Hz) δ (in ppm with reference to the signal of CDCl$_3$ at δ 7.24 ppm) 9.37 (1H, s, H-8'), 6.81 (1H, brddd, J=10.2, 4.0, 0.8, H-4), 6.33 (1H, brtq, J=7.1, 1.3, H-6'), 6.00 (1H, brdd, J=10.2, 1.2, H-3), 5.55 (1H, brq, J=4.2, H-5), 5.45 (1H, d, J=9.9, H-1'), 5.19 (1H, brdq, J=9.9, 1.3, H-2'), 3.31 (1H, d, J=17.6, H-7β), 2.43 (1H, brt, J=7.5, H-5'α), 2.41 (1H, brt, J=7.3, H-5'b), 2.36 (1H, brddd, J=14.6, 4.3, 0.9, H-6β), 2.27 (1H, d, J=17.6, H-7α), 2.24 (1H, dd, J=14.7, 5.5, H-6α), 2.19 (2H, brt, J=7.3, H2-4'), 2.13 [3H, s, OC(=O)CH$_3$], 1.70 (3H, brd, J=1.1 Hz, CH$_3$-10'), 1.69 (3H, d, J=1.3 Hz, CH$_3$-9'). HRTOF positive ESIMS m/z calcd for $C_{20}H_{24}O_6$: 361.1646 [M+1]$^+$, found: 361.1640 [M+1]$^+$.

8'-Hydroxy-miliusate is obtained as a white powder with a molecular formula of $C_{20}H_{26}O_6$ determined by positive HRESIMS and NMR studies. $^1$H NMR (400 MHz, CDCl$_3$, J in Hz) δ (in ppm with reference to the signal of CDCl$_3$ at δ 7.24 ppm) 6.83 (1H, brddd, J=10.3, 4.3, 1.3, H-4), 6.08 (1H, brdd, J=10.2, 1.2, H-3), 5.57 (1H, d, J=10.1, H-1'), 5.56 (1H, m, H-5), 5.17 (1H, m, H-6'), 5.05 (1H, brdq, J=10.1, 1.0, H-2'), 4.01 (1H, ABbrd, J=13.5, H-8'a), 3.95 (1H, ABbrd, J=13.4, H-8'b), 3.43 (1H, d, J=17.7, H-7β), 2.44 (1H, brddd, J=15.0, 3.2, 1.4, H-6β), 2.23 (1H, dd, J=15.1, 5.5, H-6α), 2.18 (1H, d, J=17.7, H-7α), 2.14 [3H, s, OC(=O)CH$_3$], 2.12 (2H, m, H$_2$-5'), 2.07 (2H, m, H$_2$-4'), 1.65 (3H, d, J=1.3 Hz, CH$_3$-9'), 1.61 (3H, s, CH$_3$-10'). HRTOF positive ESIMS m/z calcd for $C_{20}H_{26}O_6$: 363.1802 [M+1]$^+$, found: 363.1808 [M+1]$^+$.

10'-Hydroxy-8'-oxo-miliusate is obtained as a white powder with a molecular formula of $C_{20}H_{24}O_7$ determined by positive HRESIMS and NMR studies. $^1$H NMR (400 MHz, CDCl$_3$, J in Hz) δ (in ppm with reference to the signal of CDCl$_3$ at δ 7.24 ppm) 9.42 (1H, s, H-8'), 6.82 (1H, brddd, J=10.2, 3.9, 0.8, H-4), 6.45 (1H, brt, J=7.4, H-6'), 6.02 (1H, brdd, J=10.2, 1.2, H-3), 5.56 (1H, brq, J=4.2, H-5), 5.45 (1H, d, J=9.9, H-1'), 5.21 (1H, brdq, J=9.9, 1.2, H-2'), 4.35 (1H, ABd, J=12.8, H-10'a), 4.30 (1H, ABd, J=12.7, H-10'b), 3.32 (1H, d, J=17.6, H-7β), 2.53 (1H, brtd, J=7.6, 2.3, H-5'a), 2.51 (1H, brt, J=7.4, H-5'b), 2.39 (1H, brddd, J=14.6, 4.3, 0.7, H-6β), 2.26 (1H, d, J=17.7, H-7α), 2.23 (2H, brt, J=7.1, H$_2$-4'), 2.23 (1H, overlap, H-6α), 2.14 [3H, s, OC(=O)CH$_3$], 1.70 (3H, d, J=1.3 Hz, CH$_3$-9'). HRTOF positive ESIMS m/z calcd for $C_{20}H_{24}O_7$: 377.1595 [M+1]$^+$, found: 377.1600 [M+1]$^+$.

8', 10'-Dihydroxy-miliusate is obtained as a white powder with a molecular formula of $C_{20}H_{26}O_7$ determined by positive HRESIMS and NMR studies. $^1$H NMR (400 MHz, CDCl$_3$, J in Hz) δ (in ppm with reference to the signal of CDCl$_3$ at δ 7.24 ppm) 9.42 (1H, s, H-8'), 6.83 (1H, brddd, J=10.2, 4.1, 1.1, H-4), 6.10 (1H, brdd, J=10.2, 1.1, H-3), 5.56 (1H, brq, J=4.1, H-5), 5.50 (1H, d, J=10.0, H-1'), 5.31 (1H, brt, J=7.1, H-6'), 5.08 (1H, brdq, J=10.0, 1.2, H-2'), 4.25 (1H, ABd, J=12.8, H-10'a), 4.21 (1H, ABd, J=12.8, H-10'b), 4.19 (1H, ABd, J=13.0, H-8'a), 4.15 (1H, ABd, J=13.0, H-8'b), 3.36 (1H, d, J=17.7, H-7β), 1.63 (2H, brs, 2×OH), 2.40 (1H, brddd, J=14.9, 3.7, 1.1, H-6β), 2.23 (1H, dd, J=14.9, 5.5, H-6α), 2.22 (1H, d, J=17.9, H-7α), 2.17 (1H, brt, J=6.7, H-5'a), 2.16 (1H, brt, J=7.2, H-5'b), 2.13 [3H, s, OC(=O)CH$_3$], 2.07 (2H, brt J=6.7, H$_2$-4'), 1.65 (3H, d, J=1.3 Hz, CH$_3$-9'). HRTOF positive ESIMS m/z calcd for $C_{20}H_{26}O_7$: 379.1751 [M+1]$^+$, found: 379.1750 [M+1]$^+$.

5β-(p-Trimethylammonio-benzoyl)miliusol iodide is obtained as a white powder with a molecular formula of $C_{28}H_{36}NO_5I$ determined by positive HRESIMS. HRTOF positive ESIMS m/z calcd for $C_{28}H_{36}NO_5$: 466.2588 [M]$^+$, found: 466.2579 [M]$^+$.

5β-(p-Dimethyl-allyl-ammonio-benzoyl)miliusol bromide is obtained as a white powder with a molecular formula of $C_{30}H_{38}NO_5Br$ determined by positive HRESIMS. HRTOF positive ESIMS m/z calcd for $C_{30}H_{38}NO_5$: 492.2745 [M]$^+$, found: 492.2735 [M]$^+$.

N-(n-Butyl)-miliusol lactam is obtained as a white powder with a molecular formula of $C_{22}H_{33}NO_3$ determined by positive HRESIMS. HRTOF positive ESIMS m/z calcd for $C_{22}H_{34}NO_3$: 360.2539 [M+1]$^+$, found: 360.2530 [M+1]$^+$.

N-Phenyl-miliusol lactam is obtained as a white powder with a molecular formula of $C_{24}H_{29}NO_3$ determined by positive HRESIMS. HRTOF positive ESIMS m/z calcd for $C_{24}H_{34}NO_3$: 380.2226 [M+1]$^+$, found: 380.2235 [M+1]$^+$.

Methods of the Present Disclosure

The compound described herein exhibit broad anti-viral properties. According to methods of the present disclosure, compounds of Formulas I and II are administered to a patient to inhibit replication of or reduce cytopathic effects of viruses. For example, the HIV virus or influenza. Other viruses inhibited with compounds of Formulas I and II include but are not limited to cytomegalovirus (CMV), HSV-1 (herpes simplex virus type 1), HSV-2 (herpes simplex virus type 2), HBV hepatitis B virus), HCV (hepatitis C virus), HPV (human papilloma virus), influenza A, Influenza B, RSV (respiratory syncitial virus), RV (rhinovirus), AV (adenovirus), PIV, Epstein-Barr virus (EBV) and varicella zoster virus (VZV).

The compounds, pharmaceutical compositions, and therapeutic methods described herein are useful for preventing, treating, or ameliorating HIV infections.

The compounds, pharmaceutical compositions, and therapeutic methods described herein are useful for preventing, treating, or ameliorating infections caused by influenza viruses, including but not limited to: any of the subtypes of influenza A, influenza B, or influenza C.

In certain embodiments, the compounds, pharmaceutical compositions, and therapeutic methods disclosed herein are useful for preventing, treating, or ameliorating infections caused by influenza A viruses, including but not limited to, any of the strains of H1N1, H1N2, H1N3, H1N4, H1N5, H1N6, H1N7, H1N8, H1N9, H2N1, H2N2, H2N3, H2N4, H2N5, H2N6, H2N7, H2N8, H2N9, H3N1, H3N2, H3N3, H3N4, H3N5, H3N6, H3N7, H3N8, H3N9, H4N1, H5N2, H5N3, H5N4, H5N5, H5N6, H5N7, H5N8, H5N9, H6N1, H6N2, H6N3, H6N4, H6N5, H6N6, H6N7, H6N8, H6N9, H7N1, H7N2, H7N3, H7N4, H7N5, H7N6, H7N7, H7N8, H7N9, H8N1, H8N2, H8N3, H8N4, H8N5, H8N6, H8N7, H8N8, H8N9, H9N1, H9N2, H9N3, H9N4, H9N5. H9N6, H9N7, H9N8, H9N9, H10N1, H10N2, H10N3, H10N4, H10N5, H10N6, H10N7, H10N8, H10N9, H11N1, H11N2, H11N3, H11N4, H11N5, H11N6, H11N7, H11N8, H11N9, H12N1, H12N2, H12N3, H12N4, H12N5, H12N6, H12N7, H12N8, H12N9, H13N1, H13N2, H13N3, H13N4, H13N5, H13N6, H13N7, H13N8, H13N9, H14N1, H14N2, H14N3, H14N4, H14N5, H14N6, H14N7, H14N8, H14N9, H15N1, H15N2, H15N3, H15N4, H15N5, H15N6, H1N7, H15N8, and H15N9.

In certain embodiments, the compounds, pharmaceutical compositions, and therapeutic methods disclosed herein are useful for preventing, treating, or ameliorating infections caused by influenza A virus strains having a type 5 hemagglutinin protein. In certain embodiments, the influenza A virus strain has a type 5 hemagglutinin protein and neuraminidase protein selected from types 1 to 11. In certain embodiments, the influenza A virus is selected from the group consisting of H5N1 and H5N2.

In certain embodiments, the compounds, pharmaceutical compositions, and therapeutic methods disclosed herein are useful for preventing, treating, or ameliorating infections caused by H5N1.

The term "HIV", as used herein, refers to the human immunodeficiency virus and includes HIV-1, HIV-2 and SIV. In certain embodiments, HIV refers to HIV-1 and/or HIV-2. "HIV-1" means the human immunodeficiency virus type-1. HIV-1 can include but is not limited to extracellular virus particles and the forms of HIV-1 associated with HIV-1 infected cells. The HIV-1 virus can include any of the known major subtypes (Classes A, B, C, D E, F, G and H) or outlying subtype (Group O) including laboratory strains and primary isolates. "HIV-2" means the human immunodeficiency virus type-2. HIV-2 can include but is not limited to extracellular virus particles and the forms of HIV-2 associated with HIV-2 infected cells. The term "SIV" refers to simian immunodeficiency virus, which is an HIV-like virus that infects monkeys, chimpanzees, and other nonhuman primates. SIV can include but is not limited to extracellular virus particles and the forms of SIV associated with SIV infected cells.

In certain embodiments, the compounds, pharmaceutical compositions, and therapeutic methods disclosed herein are useful for preventing, treating, or ameliorating infections caused by HIV-1 and/or HIV-2. In certain embodiments, the compounds, pharmaceutical compositions, and therapeutic methods disclosed herein are useful for preventing, treating, or ameliorating infections caused by HIV-1 subtype B.

In certain embodiments, the compounds, pharmaceutical compositions, and therapeutic methods disclosed herein are useful for preventing, treating, or ameliorating infections caused by SIV.

Production of HIV Pseudovirions. HIV/VSV-G or HIV/HA virions were produced, respectively, by co-transfecting with either 0.5 µg VSV-G envelope expression plasmid or 0.5 µg hemagglutinin (HA) envelope expression plasmid with 0.5 µg neuraminidase (NA) expression plasmid and 2 µg replication-defective HIV vector (pNL4-3-Luc-RE) into human embryonic kidney 293T cells (90% confluent) in six-well plates via PEI (Invitrogen), as previously described with a modified procedure. The HIV vector pNL4-3.Luc. R.E. was obtained through the AIDS Research and Reference Reagent Program (Division of AIDS, NIAID, NIH). Sixteen hours post-transfection, all media were replaced with fresh, complete DMEM. Eight hours post-transfection, all media were replaced with fresh, complete DMEM. Forty-eight hours post-transfection, the supernatants were collected and filtered through a 0.45-µm-pore size filter (Millipore) and the pseudovirions were directly used for infection.

Anti-HIV and anti-H5N1 Influenza Virus Evaluation Assay. This protocol is designed to identify potential inhibitors for HIV replication (post-entry steps). In this system, the HIV vector pNL4-3.Luc. R.E. was co-transfected with the VSV-G to generate HIV/VSV-G virions, and the same HIV vector was co-transfected with the H5N1 HA and NA constructs to generate HIV virions with bird flu HA on the viral surface (HIV/HA). This pNL4-3 was derived from an infectious molecular clone of a SI, T-tropic virus, which is replication deficient since the HIV is Env⁻ and Vpr⁻. In addition, the luciferase gene (luc) carried by this recombinant HIV vector served as the reporter for HIV replication (reverse transcription, integration and HIV gene expression). The infection level was measured as relative light units (RLUs) in the infected cells. The luciferase activities of the 293T cells infected with the HIV vector pNL4-3.Luc. R.E. reached the range of $10^5$-$10^6$ RLUs, approximately 100-fold higher than the background levels when measured using the HIV virions without VSV-G. The evaluation principle is that the level of the luciferase activity in the cells should be proportional to the level of viral entry and replication. If a compound (or fraction) can interfere with HIV replication/or HA-mediated viral entry, the level of the luciferase activity in the infected cells will be reduced. Thus, using this protocol, we were able to identify fractions or compounds capable of inhibiting HIV replication. The test fractions or compounds were evaluated as follows. Target A549 human lung cells were seeded at $0.5 \times 10^5$ cells per well (24-well plate) in complete DMEM. The lung cell line was used since it is susceptible to HA-mediated viral entry. The stock HIV/VSV-G or HIV/HA virions (approximately $2 \times 10^6$ relative light units, or RLUs, on the target cells) were mixed with the individual sample first, and the mixture was incubated with the A549 target cells for 24 hours. Ten microliter of each sample in varying concentrations and 190 µl of the pseudovirus were incubated with target cells. Twenty-four (24) hours post-infection, all media containing sample and virus was removed from target cells and replaced with fresh and complete DMEM. Forty-eight (48) hours post-infection, the target cells were lysed and the luciferase activity was determined. Two different outcomes may occur: 1) It is likely that some samples will "inhibit replication" of both HIV/VSVG and HIV/HA virions (Lower Luc for HA and VSVG), since some of these samples can block post-entry steps during viral entry, or some of them are just toxic to the target cells. These samples are classified as anti-HIV. 2) The samples which can specifically inhibit the HIV/HA viral entry (Lower Luc for HIV/HA, but not for HIV/VSVG) will be classified as anti-HA inhibitors. Data collected from the anti-HIV and anti-H5N1 Influenza virus evaluation assay are shown in the tables below.

| Compound | Anti-HIV Activity ($EC_{50}$) | Selective Index* |
|---|---|---|
| 3,4-Dihydro-miliusate | 66.97 µM | 1 |
| 4α-(N-Phenyl)miliusate | 2.70 µM | >24 |
| 10'-Hydroxy-8'-oxo-miliusate | 4.97 µM | 12.1 |
| 8',10'-Dihydrox-miliusate | 14.4 µM | 9.5 |

*Selective Index = $CC_{50}/IC_{50}$ ($CC_{50}$ is cytotoxic effect of the test compound, and $IC_{50}$ is measurement of antiviral activity of test compound).

| Compound | Anti-H5N1 Activity (EC$_{50}$) | Selective Index* |
|---|---|---|
| Miliusane I | 0.71 μM | 10 |

*Selective Index = CC$_{50}$/IC$_{50}$ (CC$_{50}$ is cytotoxic effect of the test compound, and IC$_{50}$ is measurement of antiviral activity of test compound).

4α-(N-Phenyl)miliusate exhibited no toxicity in mice at doses of 40 mg/kg demonstrating the low toxicity of this compound. The conversion calculation from the tested animal doses to human clinical doses is based on the Guidance for Industry Estimating the Maximum Safe Starting Dose in Initial Clinical Trials for Therapeutics in Adult Healthy Volunteers, which was published by U.S. Department of Health and Human Services, Food and Drug Administration, Center for Drug Evaluation and Research, July 2005; Page 7: Table 1, 40 mg/kg per mouse body weight corresponds to 3.2 mg/kg per patient body weight in humans (to convert the mouse dose to a human dose, the dose is multiplied by 0.08 to obtain the calculated human dose).

Thus, in certain embodiments, the human dosage for patients weighing between 20-120 kg can range from about 64 mg to about 384 mg of the compound of formula (I) or formula (II). In certain embodiments, the compound of formula (I) or formula (II) is 3,4-Dihydro-miliusate, 4α-(N-Phenyl)miliusate, 10'-Hydroxy-8'-oxo-miliusate, 8',10'-Dihydrox-miliusate, or Miliusane I.

Cytotoxicity Assay. Approximately 5000 cells seeded in a 96-well tissue culture plate in DMEM supplemented with FBS and penicillin/streptomycin. DMSO alone or compounds in 100% DMSO were added on the following day at appropriate concentrations and incubated with cells at 37° C. in 5% $CO_2$ for 24 h. After 24 h, all media were removed and replaced with 100 μL fresh complete DMEM. After 48 h post initial addition of DMSO or compound, 20 μL of CellTiter 96 Aqueous One Solution was added per well. After gentle mixing, plates were incubated at 37° C. in 5% $CO_2$ for 4 h. Twenty-five μL of a 10% SDS solution was added per well and plates were stored at room temperature for approximately 12 h. Absorbance was measured at 450 nm using a plate reader.

4α-(N-Phenyl)miliusate shows good anti-HIV activity in our in vitro evaluation system. In order to determine its future development potential, animal study is used to evaluate the toxicity of 4α-(N-phenyl)miliusate in mice. All animal studies are approved and performed according to Animal Care and Use Guidelines of the Animal Ethics Committee at Hong Kong Baptist University and performed following Animal Care and Use guidelines set by NIH (National Institute of Health, USA). BALB/c nude mice, SPF class, male or female, 7-8 weeks old (average body weight 22 g), are purchased from Charles River Laboratories. Before the experiment, the mice are kept for one week of acclimatization to SPF class laboratory conditions. The mice are then divided into three groups: one low dose (20 mg/kg: 10 mice) group of 4α-(N-phenyl)miliusate, one high dose (40 mg/kg: 10 mice) group of 4α-(N-phenyl)miliusate, and one dose of vehicle (negative control: 10 mice). Every other day injections at i.p. sites are scheduled for 21 days. Weights of mice are measured twice a week until the end of the experiment.

Having now fully described the present invention in some detail by way of illustration and examples for purposes of clarity of understanding, it will be obvious to one of ordinary skill in the art that the same can be performed by modifying or changing the present invention within a wide and equivalent range of conditions, formulations and other parameters without affecting the scope of the present invention or any specific embodiment thereof, and that such modifications or changes are intended to be encompassed within the scope of the appended claims. The terms and expressions which have been employed are used as terms of description and not of limitation, and there is no intention that in the use of such terms and expressions of excluding any equivalents of the features shown and described or portions thereof, but it is recognized that various modifications are possible within the scope of the present invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of the present invention.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

When a group of materials, compositions, components or compounds is disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the present invention, unless otherwise stated. Whenever a range is given in the specification, for example, a temperature range, a time range, or a composition range, all intermediate ranges and subranges, as well as all individual values included in the ranges given are intended to be included in the disclosure. In the disclosure and the claims, "and/or" means additionally or alternatively. Moreover, any use of a term in the singular also encompasses plural forms.

All references cited herein are hereby incorporated by reference in their entirety to the extent that there is no inconsistency with the disclosure of this specification. Some references provided herein are incorporated by reference to provide details concerning sources of starting materials, additional starting materials, additional reagents, additional methods of synthesis, additional methods of analysis, additional biological materials, additional cells, and additional uses of the present invention. All headings used herein are for convenience only. All patents and publications mentioned in the specification are indicative of the levels of skill of those skilled in the art to which the present invention pertains, and are herein incorporated by reference to the same extent as if each individual publication, patent or patent application was specifically and individually indicated to be incorporated by reference. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extent. All publications recited herein are hereby incorporated by reference in their entirety.

INDUSTRIAL APPLICABILITY

The present disclosure relates to miliusane and analogs thereof that are useful as anti-viral agents, such as anti-HIV and anti-influenza. The present disclosure provides methods for treating viral infections, such as AIDS, HIV, and influenza infections.

I claim:

1. A method of treating a viral infection in a subject in need thereof, comprising administering a therapeutically effective amount of a compound of Formula (I) or Formula (II) to said subject, wherein said compound of Formula (I) and said compound of Formula (II) are represented by:

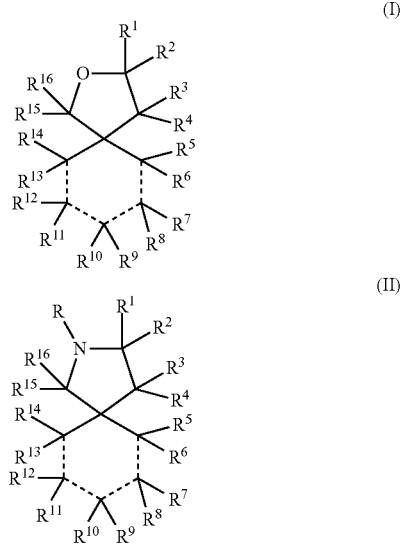

or a pharmaceutically acceptable salt or prodrug thereof, wherein a dashed line represents a single or double bond;

$R^1$ and $R^2$ are hydrogen; or taken together with the carbon atoms to which they are attached to form a carboxyl group (C=O);

each of $R^3$ and $R^4$ are independently selected from the group consisting of hydrogen, halogen, and hydroxy; or $R^3$ and $R^4$ taken together with the carbon atoms to which they are attached to form a carboxyl group (C=O);

each of $R^5$ and $R^6$ are independently selected from the group consisting of hydrogen, halogen, and —$OR^{19}$; or $R^5$ and $R^6$ taken together with the carbon atoms to which they are attached to form a carboxyl group (C=O);

each pair of the substituted groups $R^7$ and $R^8$, $R^9$ and $R^{10}$, or $R^{11}$ and $R^{12}$ is independently taken together with the carbon atoms to which they are attached to form one or more carboxyl groups (C=O); or while one substituent of $R^7$ and $R^8$, one substituent of $R^9$ and $R^{10}$, or one substituent of $R^{11}$ and $R^{12}$ is hydrogen or halogen whereas the other substituent of $R^7$ and $R^8$, the other substituent of $R^9$ and $R^{10}$, or the other substituent of $R^{11}$ and $R^{12}$ is selected from —$N(R^{17})R^{18}$ or —$N(R^{17})C(=O)R^{18}$; or while one substituent of $R^7$ and $R^8$, one substituent of $R^9$ and $R^{10}$, or one substituent of $R^{11}$ and $R^{12}$ is hydrogen or halogen whereas the other substituent of $R^7$ and $R^8$, the other substituent of $R^9$ and $R^{10}$, or the other substituent of $R^{11}$ and $R^{12}$ is selected from hydrogen and —$OR^{19}$;

$R^{13}$ and $R^{14}$ are independently selected from the group consisting of hydrogen and —$OR^{19}$;

or $R^{13}$ and $R^{14}$ taken together with the carbon atoms to which they are attached to form a carboxyl group (C=O);

$R^{15}$ is hydrocarbyl, wherein said hydrocarbyl has at least five carbons, and may be optionally substituted with one, two, or three substituents independently selected from hydroxy, halogen, aldehyde group (H—C=O), C(=O)OH, $C_{1-6}$ alkyl and $C_{1-6}$ alkoxy;

$R^{16}$ is selected from the group consisting of hydrogen and hydrocarbyl, wherein said hydrocarbyl has at least five carbons, and may be optionally substituted with one, two, or three substituents independently selected from hydroxy, halogen, aldehyde group (H—C=O), C(=O)OH, $C_{1-6}$ alkyl and $C_{1-6}$ alkoxy;

each instance of $R^{17}$ and $R^{18}$ are independently selected from hydrogen, hydrocarbyl optionally substituted with one, two, three, four or five $R^{20}$, heterocyclyl optionally substituted with one, two, three, four or five $R^{20}$ and —$(CH_2)_k$-heterocyclyl optionally substituted with one, two, three, four or five $R^{20}$;

$R^{19}$ is selected from $R^{21}$ and —$C(=O)R^{21}$;

each instance of $R^{20}$ is independently selected from the group consisting of halogen, cyno, nitro, —$R^{22}$, —$OR^{22}$, —$C(=O)R^{23}$, —$C(=O)N(R^{22})R^{23}$, —$C(=O)OR^{22}$, —$OC(=O)R^{23}$, —$N(R^{22})R^{23}$, —$N(R^{22})C(=O)R^{23}$, —$N(R^{22})(R^{23})R^{24}$, —$SR^{22}$, —$S(=O)R^{23}$, —$S(O)_2R^{23}$, —$S(O)_2N(R^{22})R^{23}$, and —$N(R^{22})S(O)_2R^{23}$;

$R^{21}$ is selected from hydrogen, heterocyclyl optionally substituted with one, two, three, four or five $R^{20}$, hydrocarbyl optionally substituted with one, two, three, four or five $R^{20}$, heteroaryl optionally substituted with one, two, three, four or five $R^{20}$, and —$(CH_2)_k$-heterocyclyl optionally substituted with one, two, three, four or five $R^{20}$;

each instance of k is independently selected from an integer selected between 1 and 6;

$R^{22}$, $R^{23}$ and $R^{24}$ are each independently selected from hydrogen or hydrocarbyl and heterocyclyl, either of which is optionally substituted with one, two, three, four or five substituents independently selected from halogen, cyano, amino, hydroxy, $C_{1-6}$ alkyl and $C_{1-6}$ alkoxy; and R is selected from hydrogen and hydrocarbyl.

2. The method according to claim 1, wherein said compound of Formula (I) has Formula (IA):

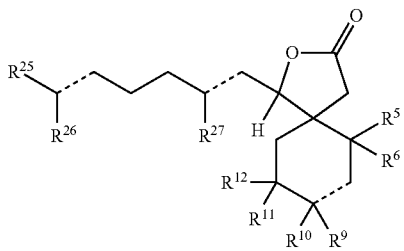

IA or a pharmaceutically acceptable salt or prodrug thereof, wherein a dashed line represents a single or double bond;

$R^5$ and $R^6$ are each independently selected from the group consisting of hydrogen and —$OR^{19}$; or $R^5$ and $R^6$ taken together with the carbon to which they are attached form a carboxyl group (C=O);

while one substituent of $R^9$ and $R^{10}$, or one substituent of $R^{11}$ and $R^{12}$ is hydrogen or halogen whereas the other substituent of $R^9$ and $R^{10}$, or the other substituent of $R^{11}$ and $R^{12}$ is selected from —$N(R^{17})R^{18}$ or —$N(R^{17})C(=O)R^{18}$; or while one substituent of $R^9$ and $R^{10}$, or one substituent of $R^{11}$ and $R^{12}$ is hydrogen or halogen whereas the other substituent of $R^9$ and $R^{10}$, or the other substituent of $R^{11}$ and $R^{12}$ is selected from hydrogen and —$OR^{19}$;

each of $R^{17}$ and $R^{18}$ is independently selected from hydrogen, heterocyclyl optionally substituted with one to five $R^{20}$, and hydrocarbyl optionally substituted with one to five $R^{20}$;

$R^{19}$ is selected from $R^{21}$ and —$C(=O)R^{21}$;

$R^{20}$ is independently selected from the group consisting of halogen, nitro, —$R^{22}$, —$OR^{22}$, —$C(=O)R^{23}$, —$C(=O)N(R^{22})R^{23}$, —$OC(=O)R^{23}$, —$N(R^{22})R^{23}$, —$N(R^{22})C(=O)R^{23}$, and —$N(R^{22})(R^{23})(R^{24})$;

$R^{21}$ is selected from hydrogen, heterocyclyl optionally substituted with one to five $R^{20}$, and hydrocarbyl optionally substituted with one to five $R^{20}$;

$R^{22}$, $R^{23}$ and $R^{24}$ are each independently selected from hydrogen, hydrocarbyl and heterocyclyl; and each of $R^{25}$, $R^{26}$, and $R^{27}$ is independently selected from the group consisting of methyl, —$CH_2OH$, C(=O)H, and C(=O)OH.

3. The method according to claim 1, wherein said compound of Formula (I) has Formula (IB):

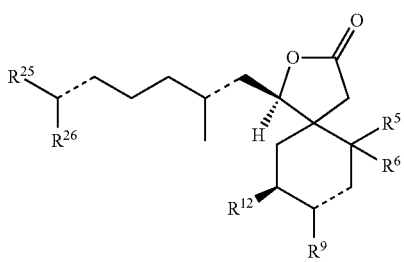

IB or a pharmaceutically acceptable salt or prodrug thereof, wherein a dashed line represents a single or double bond;

$R^5$ and $R^6$ are each independently selected from the group consisting of hydrogen and —$OR^{19}$; or $R^5$ and $R^6$ taken together with the carbon to which they are attached form a carboxyl group (C=O);

$R^9$ is hydrogen, —$N(R^{17})R^{18}$, —$N(R^{17})C(=O)R^{18}$, or —$OR^{19}$;

$R^{12}$ is hydrogen or —$OR^{19}$;

each of $R^{17}$ and $R^{18}$ is independently selected from hydrogen, heterocyclyl optionally substituted with one to five $R^{20}$, and hydrocarbyl optionally substituted with one to five $R^{20}$;

$R^{19}$ is selected from $R^{21}$ and —$C(=O)R^{21}$;

$R^{20}$ is independently selected from the group consisting of halogen, nitro, —$R^{22}$, —$OR^{22}$, —$C(=O)R^{23}$, —$C(=O)N(R^{22})R^{23}$, —$OC(=O)R^{23}$, —$N(R^{22})R^{23}$, —$N(R^{22})C(=O)R^{23}$, and —$N(R^{22})(R^{23})R^{24}$;

$R^{21}$ is selected from hydrogen, heterocyclyl optionally substituted with one to five $R^{20}$, and hydrocarbyl optionally substituted with one to five $R^{20}$;

$R^{22}$, $R^{23}$ and $R^{24}$ are each independently selected from hydrogen, hydrocarbyl and heterocyclyl; and each of $R^{25}$ and $R^{26}$ is independently selected from the group consisting of methyl, —$CH_2OH$, C(=O)H, and C(=O)OH.

4. The method according to claim 3, wherein $R^5$ is hydrogen and $R^6$ is hydroxyl or —$OC(=O)$alkyl; or $R^5$ and $R^6$ taken together with the carbon to which they are attached form a carboxyl group (C=O);

$R^9$ is hydrogen, —$N(R^{17})R^{18}$, —$N(R^{17})C(=O)R^{18}$, or —$OR^{19}$;

$R^{12}$ is hydrogen or —$OR^{19}$;

each of $R^{17}$ and $R^{18}$ is independently selected from hydrogen and hydrocarbyl optionally substituted with one to five $R^{20}$;

$R^{19}$ is selected from $R^{21}$ and —$C(=O)R^{21}$;

$R^{20}$ is independently selected from the group consisting of halogen, nitro, —$R^{22}$, —$OR^{22}$, —$N(R^{22})R^{23}$, —$N(R^{22})(R^{23})R^{24}$;

$R^{21}$ is selected from hydrogen and hydrocarbyl optionally substituted with one to five $R^{20}$;

$R^{22}$, $R^{23}$ and $R^{24}$ are each independently selected from hydrogen and alkyl; and each of $R^{25}$ and $R^{26}$ is independently selected from the group consisting of methyl, —$CH_2OH$, C(=O)H, and C(=O)OH.

5. The method according to claim 1, wherein said compound of Formula (II) has Formula (IIA):

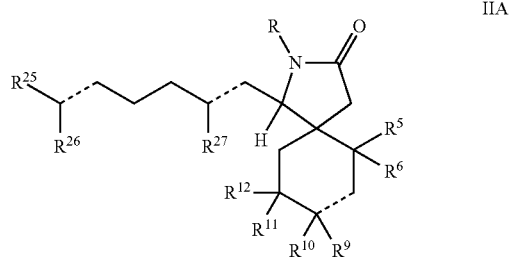

IIA or a pharmaceutically acceptable salt or prodrug thereof, wherein a dashed line represents a single or double bond;

R is hydrogen, alkyl, aryl, or $C_{1-6}$ alkyl substituted by aryl;

$R^5$ and $R^6$ are each independently selected from the group consisting of hydrogen and —$OR^{19}$; or $R^5$ and $R^6$ taken together with the carbon to which they are attached form a carboxyl group (C=O);

while one substituent of $R^9$ and $R^{10}$, or one substituent of $R^{11}$ and $R^{12}$ is hydrogen or halogen whereas the other substituent of $R^9$ and $R^{10}$, or the other substituent of $R^{11}$ and $R^{12}$ is selected from —$N(R^{17})R^{18}$ or —$N(R^{17})C(=O)R^{18}$; or while one substituent of $R^9$ and $R^{10}$, or one substituent of $R^{11}$ and $R^{12}$ is hydrogen or halogen whereas the other substituent of $R^9$ and $R^{10}$, or the other substituent of $R^{11}$ and $R^{12}$ is selected from hydrogen and —$OR^{19}$;

each of $R^{17}$ and $R^{18}$ is independently selected from hydrogen, heterocyclyl optionally substituted with one to five $R^{20}$, and hydrocarbyl optionally substituted with one to five $R^{20}$;

$R^{19}$ is selected from $R^{21}$ and —$C(=O)R^{21}$;

$R^{20}$ is independently selected from the group consisting of halogen, nitro, —$R^{22}$, —$OR^{22}$, —$C(=O)R^{23}$, —$C(=O)N(R^{22})R^{23}$, —$OC(=O)R^{23}$, —$N(R^{22})R^{23}$, —$N(R^{22})C(=O)R^{23}$, and —$N(R^{22})(R^{23})(R^{24})$;

$R^{21}$ is selected from hydrogen, heterocyclyl optionally substituted with one to five $R^{20}$, and hydrocarbyl optionally substituted with one to five $R^{20}$;

$R^{22}$, $R^{23}$ and $R^{24}$ are each independently selected from hydrogen, hydrocarbyl and heterocyclyl;

each of $R^{25}$, $R^{26}$, and $R^{27}$ is independently selected from the group consisting of methyl, C(=O)H, and C(=O)OH.

6. The method according to claim 1, wherein said compound of Formula (II) has Formula (IIB):

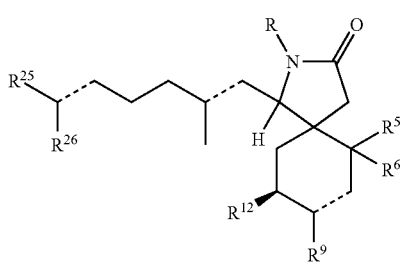

IIB or a pharmaceutically acceptable salt or prodrug thereof, wherein a dashed line represents a single or double bond;

R is hydrogen, alkyl, aryl, or $C_{1-6}$ alkyl substituted by aryl;

$R^5$ and $R^6$ are each independently selected from the group consisting of hydrogen and —$OR^{19}$; or $R^5$ and $R^6$ taken together with the carbon to which they are attached form a carboxyl group (C=O);

$R^9$ is hydrogen, —$N(R^{17})R^{18}$, —$N(R^{17})C(=O)R^8$, or —$OR^{19}$;

$R^{12}$ is hydrogen or —$OR^{19}$;

each of $R^{17}$ and $R^{18}$ is independently selected from hydrogen, heterocyclyl optionally substituted with one to five $R^{20}$, and hydrocarbyl optionally substituted with one to five $R^{20}$;

$R^{19}$ is selected from $R^{21}$ and —$C(=O)R^{21}$;

$R^{20}$ is independently selected from the group consisting of halogen, nitro, —$R^{22}$, —$OR^{22}$, —$C(=O)R^{23}$, —$C(=O)N(R^{22})R^{23}$, —$OC(=O)R^{23}$, —$N(R^{22})R^{23}$, —$N(R^{22})C(=O)R^{23}$, and —$N(R^{22})(R^{23})R^{24}$;

$R^{21}$ is selected from hydrogen, heterocyclyl optionally substituted with one to five $R^{20}$, and hydrocarbyl optionally substituted with one to five $R^{20}$;

$R^{22}$, $R^{23}$ and $R^{24}$ are each independently selected from hydrogen, hydrocarbyl and heterocyclyl; and each of $R^{25}$ and $R^{26}$ is independently selected from the group consisting of methyl, —$CH_2OH$, C(=O)H, and C(=O)OH.

7. The method according to claim 1, wherein said compound of Formula (II) has Formula (IIC):

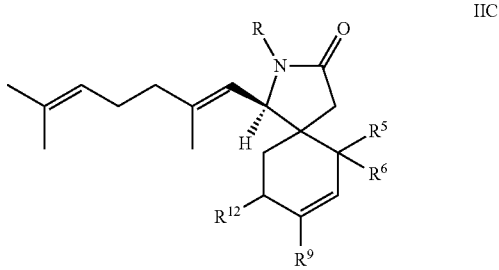

IIC or a pharmaceutically acceptable salt or prodrug thereof, wherein

R is alkyl or aryl;

$R^5$ and $R^6$ taken together with the carbon to which they are attached form a carboxyl group (C=O);

$R^9$ is hydrogen;

$R^{12}$ is hydroxyl, —OC(=O)alkyl, —OC(=O)aryl, or —OC(=O)heteroaryl, wherein —OC(=O)aryl and —OC(=O)heteroaryl are each independently optionally substituted with one to five substituents selected from the group consisting of halogen, hydroxyl, nitro, alkyl, —$N(R^{22})R^{23}$, and —$N(R^{22})(R^{23})(R^{24})$; and $R^{22}$, $R^{23}$ and $R^{24}$ are each independently selected from hydrogen and alkyl.

8. The method according to claim 1, wherein said compound of formula (I) or said compound of formula (II) is selected from the group consisting of miliusane I, 4β-(N-phenyl)miliusate, 4α-(N-phenyl)miliusate, 4β-(N-benzoyl-N-phenyl)miliusate, 4α-(N-benzoyl-N-phenyl)miliusate, hexahydro-miliusate, 3, 4-dihydro-miliusate, 2', 3', 6', 7'-tetrahydro-miliusate, 2-hydroxy-3, 4-dihydro-miliusate, 2-acetoxy-3, 4-dihydro-miliusate, 8'-oxo-miliusate, 8'-hydroxy-miliusate, 10'-hydroxy-8'-oxo-miliusate, 8', 10'-dihydroxy-miliusate, 5β-(p-trimethylammonio-benzoyl)miliusol iodide, 5β-(p-dimethyl-allyl-ammonio-benzoyl)miliusol bromide, N-(n-butyl)-miliusol lactam and N-phenyl-miliusol lactam represented by the following formula:

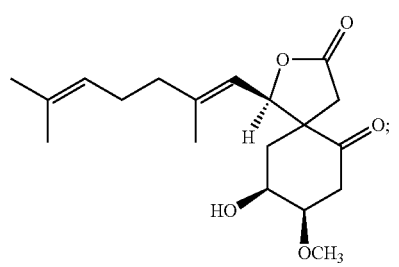
Miliusane I
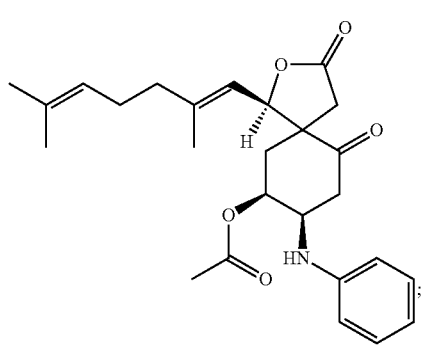
4β-(N-Phenyl)miliusate
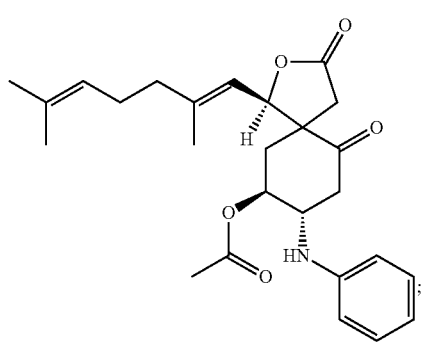
4α-(N-Phenyl)miliusate
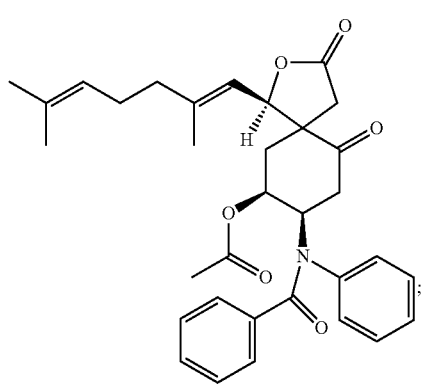
4β-(N-Benzoyl-N-phenyl)miliusate
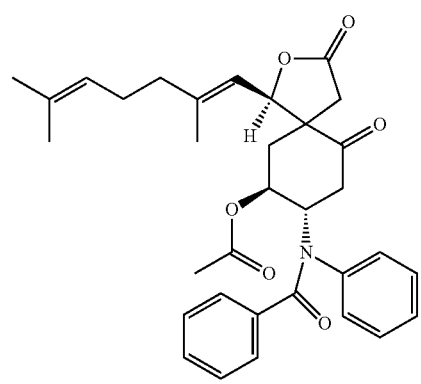
4α-(N-Benzoyl-N-phenyl)miliusate
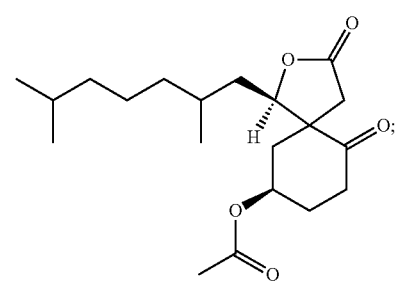
Hexahydro-miliusate
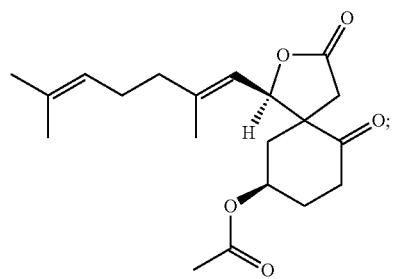
3,4-Dihydro-miliusate
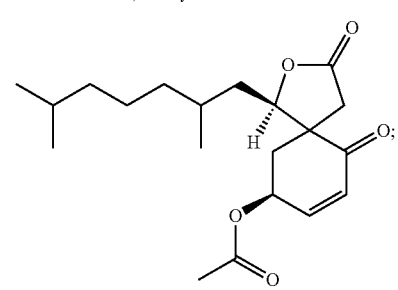
2′,3′,6′,7′-Tetrahydro-miliusate
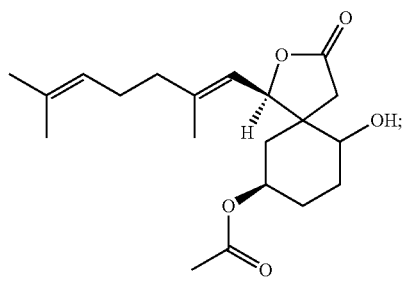
2-Hydroxy-3,4-dihydro-miliusate 2-Acetoxy-3,4-dihydro-miliusate 8'-Oxo-miliusate 8'-Hydroxy-miliusate 10'-Hydroxy-8'-oxo-miliusate 8',10'-Dihydroxy-miliusate 5β-(p-Trimethylammonio-benzyol)miliusol iodide 5β-(p-Dimethyl-allyl-ammonio-benzyol)miliusol bromide N-(n-Butyl)-miliusol lactam N-Phenyl-miliusol lactam or a pharmaceutically acceptable salt or prodrug thereof.

9. The method according to claim 1, wherein said viral infection is influenza or HIV.

10. The method of claim 9, wherein said influenza is influenza A.

11. The method of claim 10, wherein said influenza A is H5N1.

12. The method of claim 10, wherein said compound of Formula (I) inhibits the viral entry of influenza A to a host cell.

13. The method of claim 11, wherein said compound of Formula (I) is miliusane I.

14. The method of claim 9, wherein said compound of Formula (I) inhibits the viral replication of the HIV virus.

15. The method of claim 1, wherein said viral infection is HIV and said compound of Formula (I) has Formula (IC):

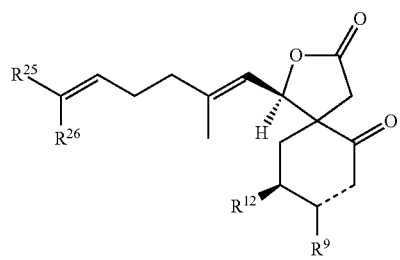

IC or a pharmaceutically acceptable salt or prodrug thereof, wherein a dashed line represents a single or double bond;

$R^9$ is hydrogen or $-N(R^{17})R^{18}$;

$R^{12}$ is hydroxyl, $-O(C=O)$alkyl;

$R^{17}$ is hydrogen;

$R^{18}$ is aryl optionally substituted with one or two $R^{20}$;

$R^{20}$ is independently selected from the group consisting of halogen, nitro, hydroxyl and alkyl; and each of $R^{25}$ and $R^{26}$ is independently selected from the group consisting of methyl, $-CH_2OH$, and $C(=O)H$.

16. The method of claim 15, wherein said compound of Formula (IC) is selected from the group consisting of:

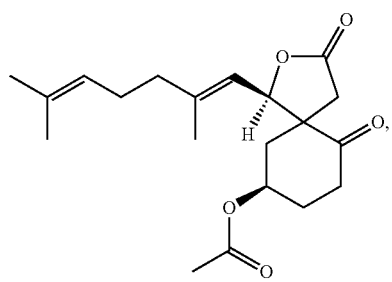

3,4-Dihydro-miliusate

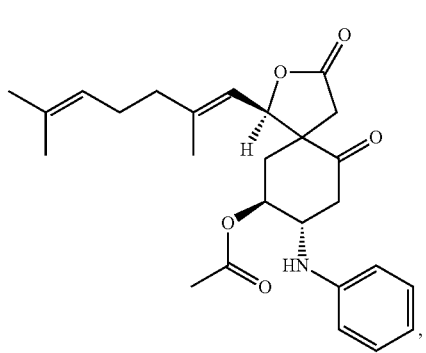

4α-(N-Phenyl)miliusate

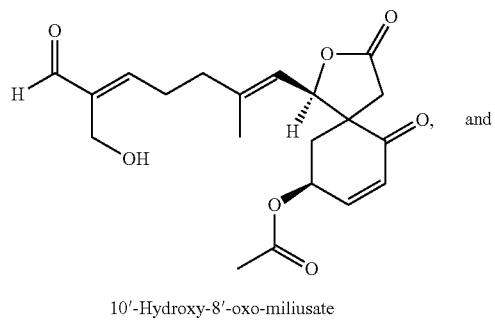

10'-Hydroxy-8'-oxo-miliusate

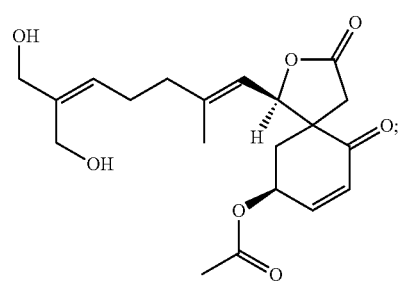

8',10'-Dihydroxy-miliusate pharmaceutically acceptable salt or prodrug thereof.

17. The method of claim 1, wherein said subject is human.

18. The method of claim 17, wherein said viral infection is HIV and said compound of Formula (I) is selected from the group consisting of:

3,4-Dihydro-miliusate

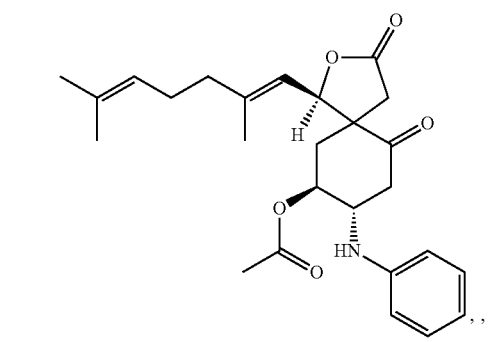

4α-(N-Phenyl)miliusate

-continued
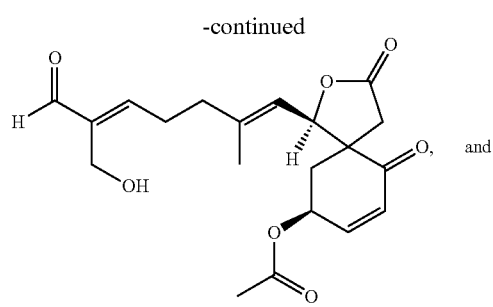
10'-Hydroxy-8'-oxo-miliusate
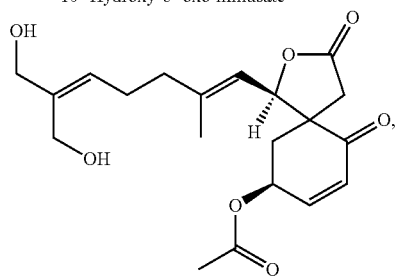
8',10'-Dihydroxy-miliusate
wherein said compound is administered at a dosage of 3.2 mg per kilogram of body weight of said human.
19. The method of claim 17, wherein said compound of Formula (I) is 4α-(N-phenyl)miliusate.
* * * * *